(12) United States Patent
Shelke et al.

(10) Patent No.: US 11,464,742 B2
(45) Date of Patent: *Oct. 11, 2022

(54) EXTENDED RELEASE COMPOSITIONS COMPRISING TRIHEXYPHENIDYL

(71) Applicant: AMNEAL COMPLEX PRODUCTS RESEARCH LLC, Bridgewater, NJ (US)

(72) Inventors: Namdev B. Shelke, Hillsborough, NJ (US); Siva Ram Kiran Vaka, Piscataway, NJ (US); Navnit H. Shah, Monmouth Junction, NJ (US); Dipen Desai, Whippany, NJ (US); Wantanee Phuapradit, Lewes, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/482,672

(22) Filed: Sep. 23, 2021

(65) Prior Publication Data

US 2022/0249377 A1    Aug. 11, 2022

Related U.S. Application Data

(63) Continuation of application No. 17/166,266, filed on Feb. 3, 2021, now Pat. No. 11,154,505.

(51) Int. Cl.
*A61K 9/16* (2006.01)
*A61K 31/4453* (2006.01)
*A61K 9/00* (2006.01)

(52) U.S. Cl.
CPC .......... *A61K 9/1652* (2013.01); *A61K 9/0002* (2013.01); *A61K 9/0053* (2013.01); *A61K 9/1617* (2013.01); *A61K 9/1635* (2013.01); *A61K 9/1682* (2013.01); *A61K 31/4453* (2013.01)

(58) Field of Classification Search
CPC ...... A61K 9/16; A61K 9/1605; A61K 9/1611; A61K 9/1617; A61K 9/1676; A61K 9/167
See application file for complete search history.

(56) References Cited

U.S. PATENT DOCUMENTS 10,869,839 B2 * 12/2020 Shelke ................. A61K 9/2886
11,040,014 B2 * 6/2021 Shelke ............... A61K 31/4453
11,045,420 B2 * 6/2021 Shelke ................. A61K 9/1652
2009/0196935 A1    8/2009 Ahmed et al.
2011/0135724 A1 * 6/2011 Venkatesh ................ A61P 1/08
424/465

FOREIGN PATENT DOCUMENTS

WO    WO 2010096820 A1    8/2010
WO    WO 2016087952 A1    6/2016
WO    WO-2016087952 A1 *  6/2016 ........... A61K 31/155

OTHER PUBLICATIONS

Cheung et al (Pharmacokinetic Evaluation of a Sustained-Release Formulation of trihexyphenidyl in Healthy Volunteers; Journal of Pharmaceutical Sciences, vol. 77, No. 9, Sep. 1988). (Year: 1988).*
K Vinay Kumar et al., Formulation and Evaluation of Extended Release Trihexyphenidyl Hydrochloride Hard Gelatin Capsules, International Journal of Pharmaceutical Sciences and Nanotechnology; vol. 4, Issue 1, Apr.-Jun. 2011.
Cheung, et al., Pharmacokinetic Evaluation of a Sustained-Release Formulation of Trihexyphenidyl in Healthy Volunteers; Journal of Pharmaceutical Sciences, American Pharmaceutical Association, vol. 77, No. 9, Sep. 1988, pp. 748-750.
Devissaguet, J.P., et al., Etude pharmacocinetique comparative de deux formes galeniques de trihexyphenidyle dosees a 5 mg comprimes (Artane TM) et gelules a liberation progressive (Parkinane retard TM), Therapie, vol. 3, No. 39, May 1, 1984, pp. 231-236.
Schwab, et al., Slow-release Trihexyphenidyl in Parkinson's Disease, JAMA, (19620000), vol. 180, No. 2, pp. 159-161.
Corbin, Trihexyphenidyl: Evaluation of New Agent in Treatment of Parkinsonism, JAMA, (19490000), vol. 141, No. 6, pp. 377-382.
International Search Report and Written Opinion dated Jan. 13, 2020 in PCT/US19/51928.

* cited by examiner

*Primary Examiner* — Micah Paul Young

(57) ABSTRACT

The present disclosure provides extended release trihexyphenidyl compositions suitable for once- or twice-daily administration. The compositions comprise a core comprising at least one organic acid; at least one drug layer comprising trihexyphenidyl or a pharmaceutically acceptable salt thereof over the core; and a functional coat over the drug-layered core. The compositions of the disclosure provide extended release with reduced $C_{max}$, a $C_{min}:C_{max}$ ratio of ≥0.4, Fluctuation Index of ≤1, while providing and maintaining at least a minimum therapeutically effective plasma concentration, of the trihexyphenidyl or the pharmaceutically acceptable salt thereof for at least about 10 hours. The compositions of the disclosure improve solubility of the trihexyphenidyl or the pharmaceutically acceptable salt thereof at a pH of greater than or equal to 5, to provide and maintain at least a minimum effective concentration of the drug at such pH.

22 Claims, 16 Drawing Sheets

EXTENDED RELEASE COMPOSITIONS COMPRISING TRIHEXYPHENIDYL

1. RELATED APPLICATIONS

Figure 1:
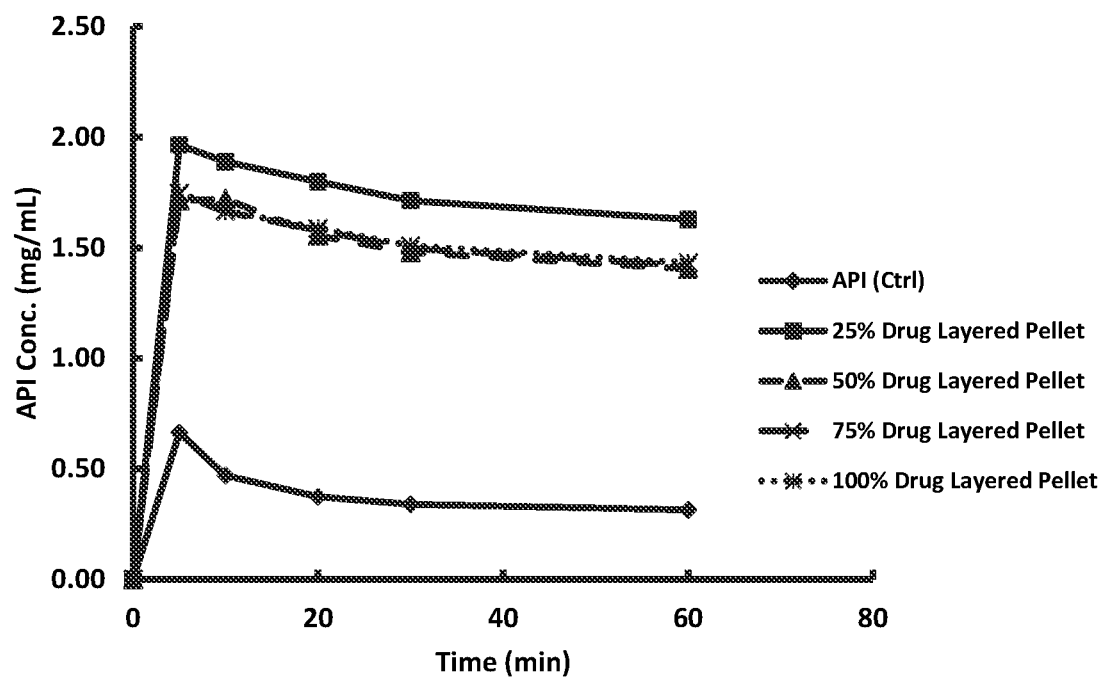

This application is a continuation of U.S. application Ser. No. 17/166,266, filed Feb. 3, 2021.

2. TECHNICAL FIELD

The present disclosure provides extended release (ER) trihexyphenidyl (THP) compositions suitable for once or twice daily administration. The compositions provide an acid microenvironment that improves the solubility of trihexyphenidyl (THP) at a pH greater than or equal to about 5 and helps to provide and maintain therapeutic plasma concentrations of THP for at least about 10 hours, under physiologically relevant conditions. The compositions of the disclosure provide extended release PK profile with reduced dose related peak-to-trough fluctuations, e.g., providing $C_{min}:C_{max}$ ratio of greater than or equal to 0.4 and Fluctuation Index (FI) of less than or equal to 1, for improved tolerability and reduced adverse effects associated with high plasma concentrations and high peak-to-trough fluctuations. The ER trihexyphenidyl compositions of the disclosure include pellets suitable for dosing in capsules, sachets, administration with feeding tube, and as sprinkles on food.

3. BACKGROUND

Dystonia is a central nervous system (CNS) disorder associated with overactivity of cholinergic interneurons (ChIs) that provide acetylcholine (Ach) to medium spiny neurons (MSNs). Overactivity of cholinergic interneurons produces more acetylcholine for uptake by medium spiny neurons leading to dystonia. Trihexyphenidyl, a phenyl propylamine (also known as benzhexol and trihex) is an anticholinergic agent that binds to medium spiny neurons and prevents uptake of acetylcholine by the medium spiny neurons. THP is a synthetic antispasmodic drug that is widely used in the treatment of patients with all forms of parkinsonism, including primary or idiopathic Parkinson's disease, secondary symptomatic parkinsonism (postencephalitic, arteriosclerotic, infection-induced, tumor-induced, trauma-induced, and drug-induced), and involuntary movements due to side effects of certain psychiatric drugs. Cheung et al. (1988) "Pharmacokinetic evaluation of a sustained release formulation of trihexyphenidyl in healthy volunteers" *J. Pharm. Sci.*, 77(9):748-50. It is approved by the FDA as an adjunct in the treatment of all forms of parkinsonism and for the control of extrapyramidal disorders caused by central nervous system drugs such as dibenzoxazepines, phenothiazines, thioxanthenes, and butyrophenones. THP is also used off-label for treating primary dystonia, dystonia associated with cerebral palsy (dyskinetic cerebral palsy), and/or sialorrhea.

THP, chemically known as α-cyclohexyl-α-phenyl-1-piperidinepropanol, has the following chemical structure:

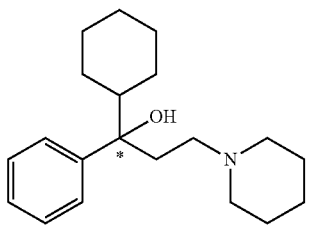 [SMILES: OC(CCN1CCCCC1)(c1ccccc1)C1CCCCC1]

Trihexyphenidyl hydrochloride (THP HCl) was introduced as a synthetic drug for treatment of Parkinson's disease in 1949. Dosahay and Schwab (1962) "Slow-release Trihexyphenidyl in Parkinson's Disease" *JAMA*, 180(2):159-61. It has proved to be one of the more useful drugs for the treatment of Parkinson's disease and has been available in 2 mg and 5 mg scored tablets for many years. Corbin (1949) "Trihexyphenidyl: Evaluation of New Agent in Treatment of Parkinsonism" *JAMA*, 141(6):377-82.

The two major problems associated with THP are its poor tolerability and the need for frequent administration. In addition, some patients with dystonia are on feeding tubes that require the treatment to be administered via feeding tubes (Dys-Society-2020). THP has the potential to cause clinically important and dose limiting anti-cholinergic adverse effects (AEs), such as drowsiness, confusion, dizziness, constipation, urinary retention, and blurred vision (NDA #006773, 2003). Due to poor tolerability, the treatment is initiated at a very low dose and titrated slowly over several weeks until the optimum dose is achieved. Also, to manage the side effects, THP is generally administered in divided doses, typically three-times-a day. If the side effects become intolerable, the dose is reduced, or the drug is stopped. Further, THP hydrochloride, due to its poor solubility at pH greater than or equal to about 5, exhibits highly variable plasma levels after oral administration as extended release dosage forms.

The approved and currently marketed IR THP hydrochloride products have side effects, e.g., drowsiness, dizziness or blurred vision, dry mouth, stomach upset, vomiting, diarrhea, constipation, and difficulty in urinating, associated with high peak serum concentrations ($C_{max}$) and high peak-to-trough fluctuations comprising trough-to-peak concentration ratios ($C_{min}:C_{max}$) of less than about 0.4 and FI of greater than 1. In elderly individuals, if the dosage strength is too high, the side effects are urinary difficulty and/or retention, confusion, agitation, and hallucinations, particularly during the night. Dosahay and Schwab, supra. Such adverse effects that can be reduced approximately by 50% with the use of controlled release formulations (Cheung, 1988).

Additionally, unlike other compounds employed in the treatment of Parkinson's disease, THP shows little tendency towards an increase in tolerance and can be used with consistent benefit for over ten years. Further, THP is an efficient drug that is safe and has a long period of clinical experience. The above-mentioned advantages of THP make it an ideal candidate for extended release formulations that can provide and maintain reasonably stable therapeutically effective plasma concentrations.

However, dosing at higher strengths as ER dosage forms results in various side effects associated with an initial drug release in an amount that is higher than the therapeutic range (e.g., a burst release of the drug) and highly variable blood plasma levels after oral administration due to poor solubility of THP at a pH greater than or equal to about 5, e.g., decrease in solubility of THP as the dosage form passes through the intestine. Thus, it is desirable to develop ER THP compositions that can reduce variations in plasma concentrations of the drug, associated with a reduction in solubility at a pH of greater than about 5 in the lower GI tract, e.g., intestine, and reduce side effects associated with presently approved IR compositions.

There is currently no extended release product in the market. There is a need for extended release THP formulation that can improve patient compliance and tolerability by reducing the $C_{max}$ and $C_{max}$-to-$C_{min}$ fluctuations (FI) and increasing the $C_{min}$:$C_{max}$ ratio to greater than or equal to 0.4, while providing therapeutic plasma concentrations throughout the day with once-daily dosing.

There is a need to develop once-a-day extended release THP compositions, which can provide at least a 10-hour, preferably from about 16-hour to abut 24-hour, release profile of trihexyphenidyl hydrochloride under physiologically relevant conditions, improve drug solubility at pH of greater than or equal to about 5, reduce side effects associated with unwanted initial burst in drug release, enable sprinkling on food or liquid, enable administration with feeding tube, and exhibit shelf life of 2 years at controlled room temperature conditions.

In certain embodiments, the present disclosure provides for a pharmaceutical pellet composition comprising a core comprising at least one organic acid; a first drug layer covering at least a portion of the core; and a functional coat covering at least a portion of the first drug layer. The first drug layer comprises trihexyphenidyl or a pharmaceutically acceptable salt thereof, and a nonionic water-soluble polymer. The functional coat comprises a nonionic water-insoluble polymer, and a pore former in a weight ratio of from about 50:50 to about 98:2. The functional coat has a coating weight gain of from about 5% w/w to about 40% w/w, based on the total weight of the composition without the functional coat. The trihexyphenidyl or the pharmaceutically acceptable salt thereof, and the organic acid are present in a weight ratio of from about 1:5 to about 1:100. The organic acid improves solubility of the trihexyphenidyl or the pharmaceutically acceptable salt thereof, in the portions of the GI tract with pH of greater than or equal to 5, to provide and maintain at least a minimum therapeutic plasma concentration of the trihexyphenidyl or the pharmaceutically acceptable salt thereof at such pH. The composition provides extended release of trihexyphenidyl, or the pharmaceutically acceptable salt thereof, with a Fluctuation Index (FI) of ≤1.

In certain embodiments, the core is a pellet, bead, seed, or a granule comprising at least one organic acid. In certain embodiments, the core is a pellet, bead, seed, or a granule coated with at least one coating comprising at least one organic acid. In certain embodiments, the core is an organic acid or a mixture of organic acids.

In certain embodiments, the first drug layer comprises trihexyphenidyl hydrochloride.

In certain embodiments, the organic acid is selected from the group consisting of tartaric acid, citric acid, fumaric acid, succinic acid, malic acid, and mixtures thereof.

In certain embodiments, the nonionic water-soluble polymer in the drug layer is selected from the group consisting of hydroxypropyl cellulose, methyl cellulose, hydroxypropyl methylcellulose, hydroxyethyl cellulose, polyethylene glycol, polyvinyl alcohol, poloxamer, polyvinyl pyrrolidone-vinyl acetate copolymer (e.g., copovidone), and mixtures thereof.

In certain embodiments, the nonionic water-insoluble polymer in the functional coat is selected from the group consisting of ethyl cellulose, cellulose acetate, cellulose diacetate, cellulose triacetate, cellulose propionate, a polyvinyl acetate dispersion, and mixtures thereof.

In certain embodiments, the pore former is an enteric polymer selected from the group consisting of cellulose acetate phthalate, cellulose acetate succinate, methylcellulose phthalate, hydroxyethyl cellulose phthalate, polyvinyl acetate phthalate, polyvinyl butyrate acetate, vinyl acetate-maleic anhydride copolymer, methacrylic acid copolymer, hydroxypropyl methylcellulose phthalate, polyvinyl acetate phthalate, cellulose acetyl phthalate, and mixtures thereof.

In certain other embodiments, the pore former is a nonionic, pH-independent water-soluble polymer selected from the group consisting of methyl cellulose, hydroxypropyl cellulose, hydroxypropyl methylcellulose, hydroxyethyl cellulose, polyethylene glycol, polyvinyl alcohol, poloxamer, polyvinyl pyrrolidone-vinyl acetate copolymer (e.g., copovidone), and mixtures thereof.

In certain embodiments, the first drug layer further comprises at least one organic acid selected from the group consisting of tartaric acid, citric acid, fumaric acid, succinic acid, malic acid, and mixtures thereof.

In certain embodiments, the composition further comprises a second drug layer, covering at least a portion of the functional coat, and comprising trihexyphenidyl or a pharmaceutically acceptable salt thereof.

In certain embodiments, the composition provides and maintains at least a minimum therapeutic plasma concentration of the trihexyphenidyl or the pharmaceutically acceptable salt thereof for at least about 10 hours.

In certain embodiments, the composition is suitable for once-a-day administration. In certain embodiments, the present disclosure provides for a pharmaceutical composition comprising a core comprising at least one organic acid; a first drug layer covering at least a portion of the core; and a functional coat covering at least a portion of the first drug layer. The first drug layer comprises trihexyphenidyl or a pharmaceutically acceptable salt thereof, and a nonionic water-soluble polymer. The functional coat comprises a nonionic water-insoluble polymer, and a pore former in a weight ratio of from about 50:50 to about 98:2. The functional coat has a coating weight gain of from about 5% w/w to about 40% w/w, based on the total weight of the composition without the functional coat. The trihexyphenidyl or the pharmaceutically acceptable salt thereof, and the organic acid are present in a weight ratio of from about 1:5 to about 1:100. The organic acid improves solubility of the trihexyphenidyl or the pharmaceutically acceptable salt thereof, in the portions of the GI tract with pH of greater than or equal to 5, to provide and maintain at least a minimum therapeutic plasma concentration of trihexyphenidyl or the pharmaceutically acceptable salt thereof at such pH. The composition provides extended release of the trihexyphenidyl or the pharmaceutically acceptable salt thereof, with a $C_{min}$:$C_{max}$ ratio of ≥0.4.

In certain embodiments, the core is a pellet, bead, seed, or a granule comprising at least one organic acid. In certain embodiments, the core is a pellet, bead, seed, or a granule coated with at least one coating comprising at least one organic acid. In certain embodiments, the core is an organic acid or a mixture of organic acids.

In certain embodiments, the disclosure provides a method for making a pharmaceutical pellet composition comprising trihexyphenidyl or a pharmaceutically acceptable salt thereof, the method comprising:

a) coating a core comprising at least one organic acid with a first drug layer comprising trihexyphenidyl or a pharmaceutically acceptable salt thereof, and a nonionic water-soluble polymer to obtain a drug layered core, and b) coating the drug layered core with a functional coat comprising a nonionic water-insoluble polymer, and a pore former.

The nonionic water-insoluble polymer and the pore former are present in a weight ratio of from about 50:50 to about 98:2; the trihexyphenidyl or the pharmaceutically acceptable salt thereof, and the organic acid are present in a weight ratio of from about 1:5 to about 1:100; and the functional coat has a coating weight gain of from about 5% to about 40% w/w, based on the total weight of the pellet without the functional coat. The organic acid improves solubility of the trihexyphenidyl or the pharmaceutically acceptable salt thereof, in the portions of the GI tract with pH of greater than or equal to 5, to provide and maintain at least a minimum therapeutic plasma concentration of trihexyphenidyl or the pharmaceutically acceptable salt thereof at such pH. The composition provides extended release of the trihexyphenidyl or the pharmaceutically acceptable salt thereof, with a $C_{min}:C_{max}$ ratio of ≥0.4.

In certain embodiments, the core is an organic acid or a mixture of organic acids; comprises at least one organic acid; or is a pellet, bead, seed, or a granule coated with at least one coating comprising at least one organic acid.

In certain embodiments, the disclosure provides a method for treating dystonia, sialorrhea, and/or dyskinesia. The method comprises orally administering to a subject in need thereof, a pharmaceutical composition comprising a core comprising at least one organic acid; a first drug layer covering at least a portion of the core; and a functional coat covering at least a portion of the first drug layer. The first drug layer comprises trihexyphenidyl or a pharmaceutically acceptable salt thereof, and a nonionic water-soluble polymer. The functional coat comprises a nonionic water-insoluble polymer and a pore former in a weight ratio of from about 50:50 to about 98:2. The functional coat has a coating weight gain of from about 5% w/w to about 40% w/w, based on the total weight of the composition without the functional coat. The trihexyphenidyl or the pharmaceutically acceptable salt thereof, and the organic acid are present in a weight ratio of from about 1:5 to about 1:100. The organic acid improves solubility of the trihexyphenidyl or the pharmaceutically acceptable salt thereof, in the portions of the GI tract with pH of greater than or equal to 5, to provide and maintain at least a minimum therapeutic plasma concentration of the trihexyphenidyl or the pharmaceutically acceptable salt thereof at such pH. The composition provides extended release of trihexyphenidyl or the pharmaceutically acceptable salt thereof, with a $C_{min}:C_{max}$ ratio of ≥0.4.

5. BRIEF DESCRIPTION OF THE DRAWINGS

FIG. 1 compares kinetic solubility of THP HCl (API control (Ctrl)) and THP HCl-tartaric acid pellets at different drug:tartaric acid weight ratios (as represented by 25%, 50%, 75%, and 100% of drug layering), performed using USP Apparatus I at 100 RPM and 37° C., in 900 ml of pH 6.8 phosphate buffer. FIG. 1 demonstrates that presence of tartaric acid-containing cores increased the amount of THP released at a pH of about 6.8. The figure further demonstrates that increasing the amount of drug layer reduced the amount of THP released at a pH of about 6.8.

Figure 2:
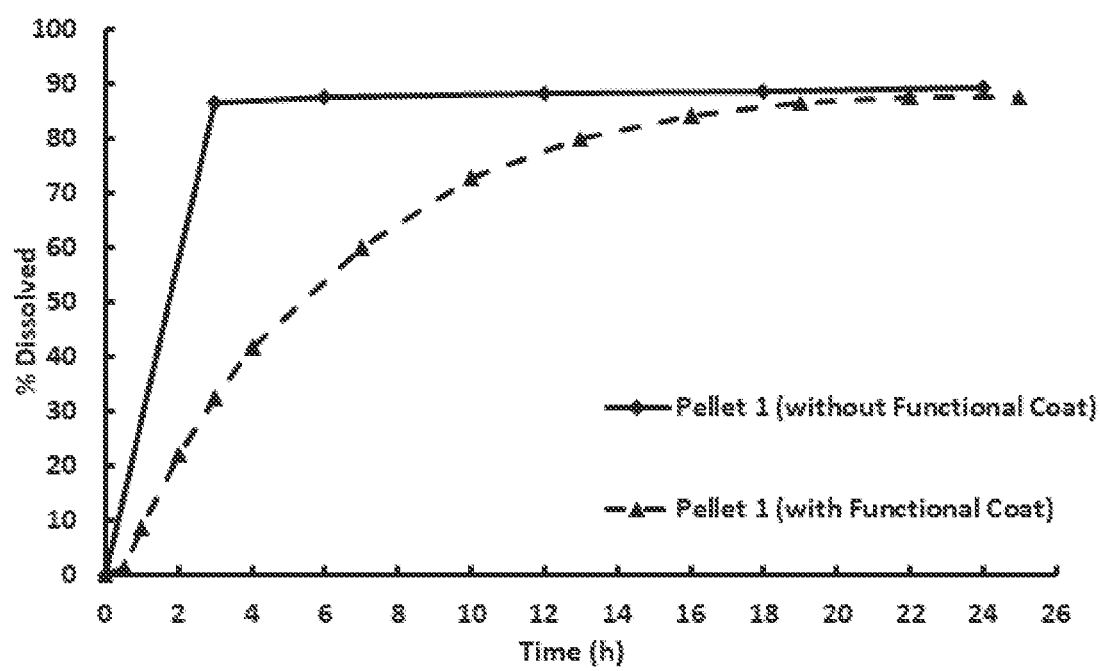

FIG. 2 compares two-stage dissolution profiles of THP HCl pellets with and without a functional coat, Pellet 1 coated with a functional coat; and Pellet 1 without a functional coat, performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. FIG. 2 demonstrates that Pellet 1 without a functional coat provided faster dissolution/higher dissolution rate compared to the Pellet 1 with a functional coat.

Figure 3:
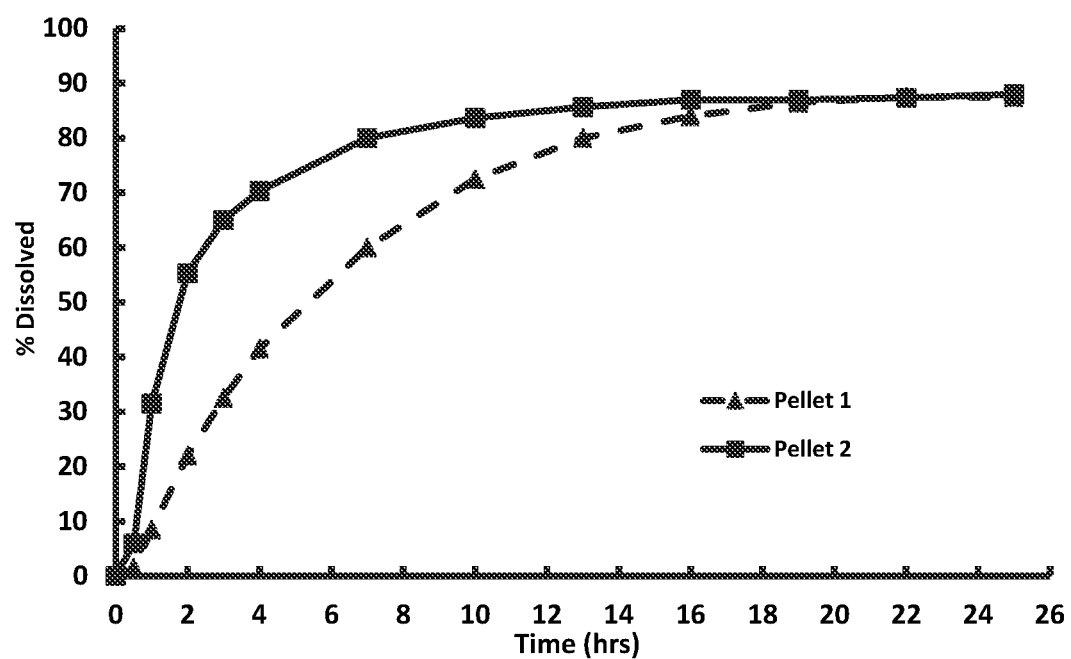

FIG. 3 compares two-stage dissolution profiles of Pellet 1 (containing tartaric acid:THP HCl weight ratio of about 10:1) and Pellet 2 (containing tartaric acid:THP HCl weight ratio of about 40:1), performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. FIG. 3 demonstrates that Pellet 2 containing tartaric acid:THP HCl weight ratio of 40:1, provided faster dissolution with an initial burst release of THP compared to Pellet 1 containing tartaric acid:THP HCl weight ratio of about 10:1.

Figure 4:
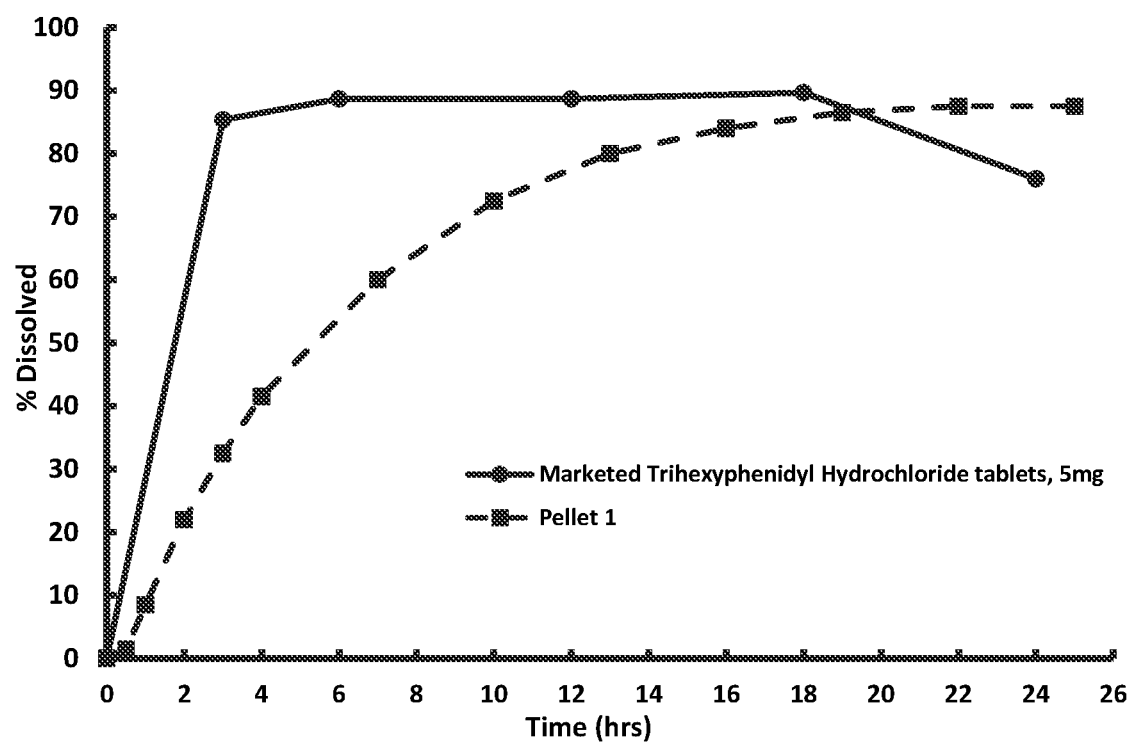

FIG. 4 compares dissolution profiles of Pellet 1 formulation and marketed IR THP HCl tablets (5 mg), performed using USP Apparatus I at 100 RPM and 37° C., in 900 ml of pH 6.8 phosphate buffer for 24 hours. FIG. 4 demonstrates that the marketed IR THP HCl tablets provided higher dissolution rate with an initial burst release of THP HCl compared to Pellet 1 formulation. FIG. 4 demonstrates that the IR marketed product provided rapid and uncontrolled initial burst release of THP compared to Pellet 1.

Figure 5:
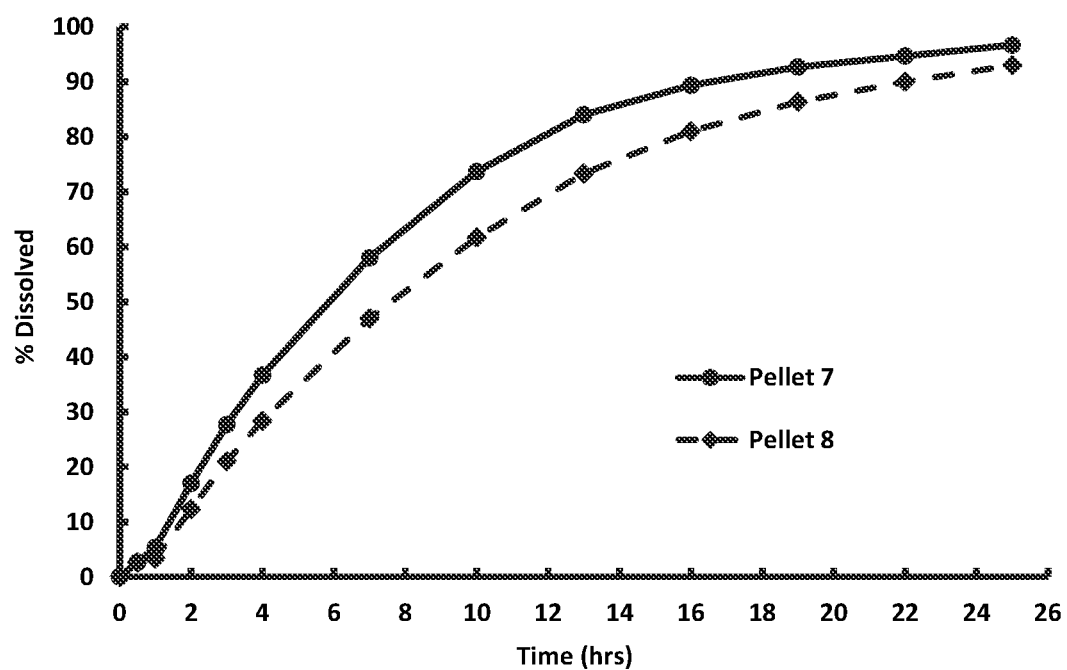

FIG. 5 compares two-stage dissolution profiles of THP HCl Pellet 7 with 20% functional coating weight gain, based on the total weight of Pellet 7 without the functional coat, and Pellet 8 with 25% functional coating weight gain, based on the total weight of Pellet 8 without the functional coat, performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. FIG. 5 demonstrates that release of THP HCl reduced with increase in functional coating weight gain.

Figure 6:
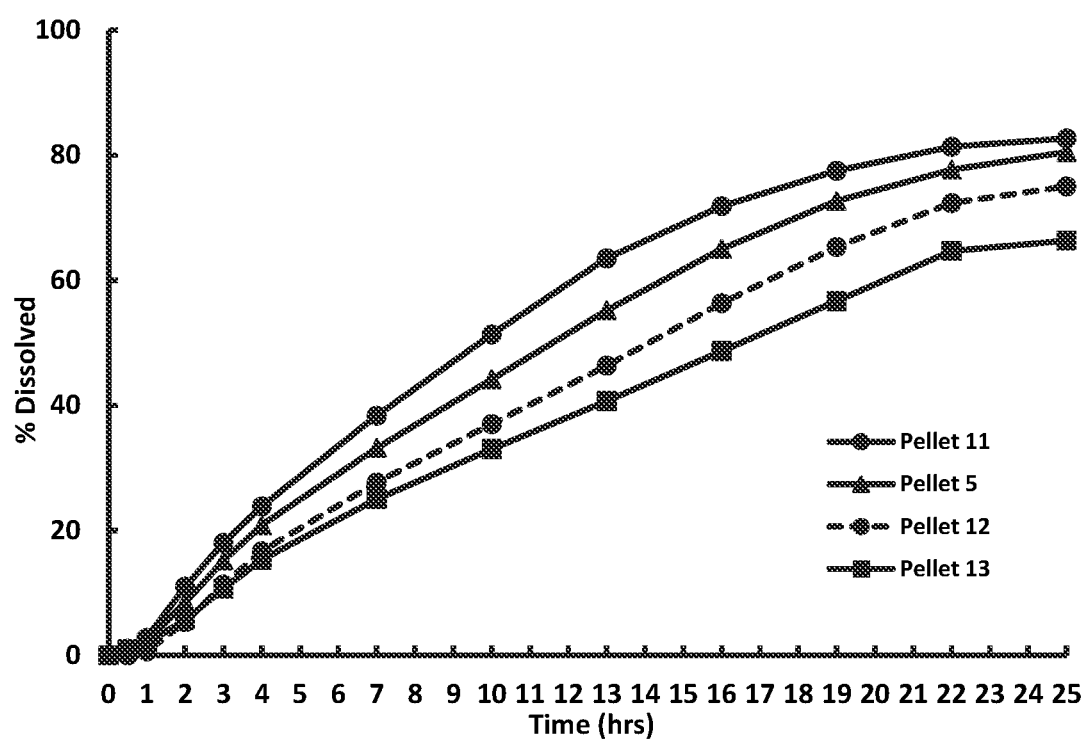

FIG. 6 compares two-stage dissolution profiles for trihexyphenidyl hydrochloride Pellets 5, 11, 12, and 13 containing 25%, 20%, 30%, and 35% coating weight gain in the functional coat, respectively, based on the total weight of the corresponding uncoated pellet, performed using USP Apparatus I at 100 RPM and 37° C., in 900 ml of pH 1.2 HCl for 1 hour followed by dissolution in 900 ml of pH 6.8 phosphate buffer for 24 hours, to simulate physiological conditions. FIG. 6 demonstrates that the release rate increased with decreasing functional coat weight gain. Pellets with 20% functional coat weight gain provided a maximum release rate and recovery of THP HCl, and pellets with 35% functional coat weight provided lowest release rate and recovery of THP HCl.

Figure 7:
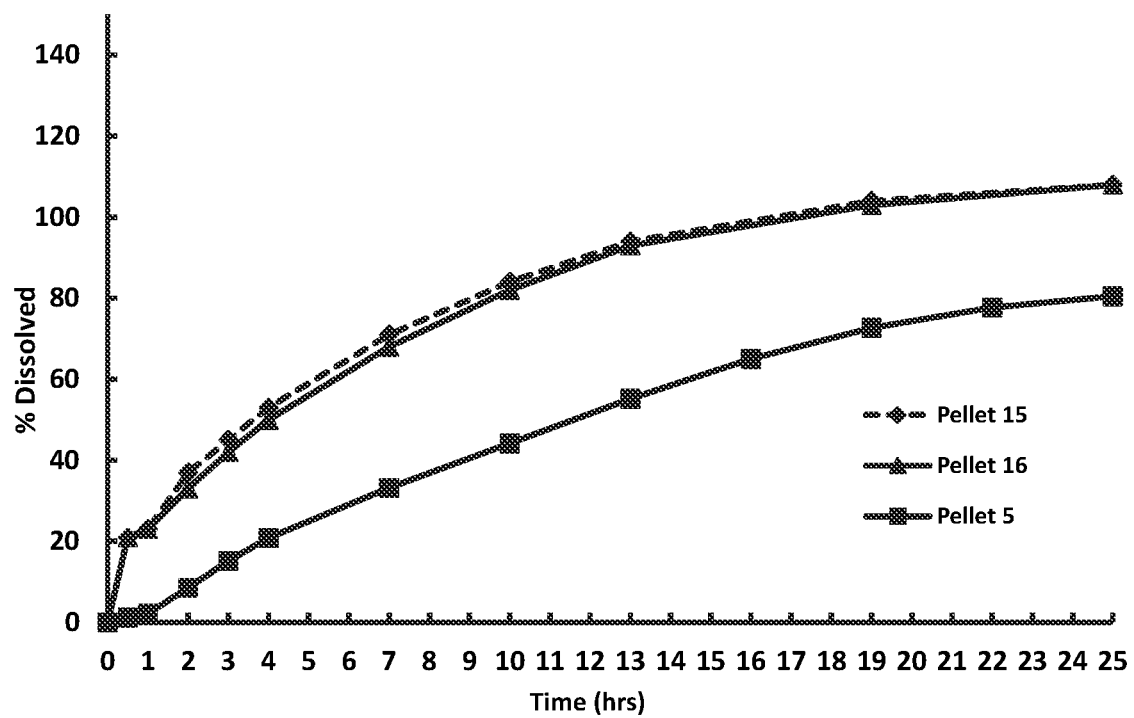

FIG. 7 compares two-stage dissolution profiles of trihexyphenidyl hydrochloride Pellets 5, 15, and 16, performed using USP Apparatus I at 100 RPM and 37° C., in 900 ml of pH 1.2 HCl for 1 hour followed by dissolution in 900 ml of pH 6.8 phosphate buffer for 24 hours, to simulate physiological conditions. FIG. 7 demonstrates that Pellet 5 (without IR drug layer-2) provided a lag time of about 2 hours, and Pellets 15 and 16 (containing IR drug layer-2) did not exhibit any lag time. FIG. 7 further demonstrates that Pellets 15 and 16 provided higher drug recovery compared to Pellet 5 (without an IR drug layer).

Figure 8:
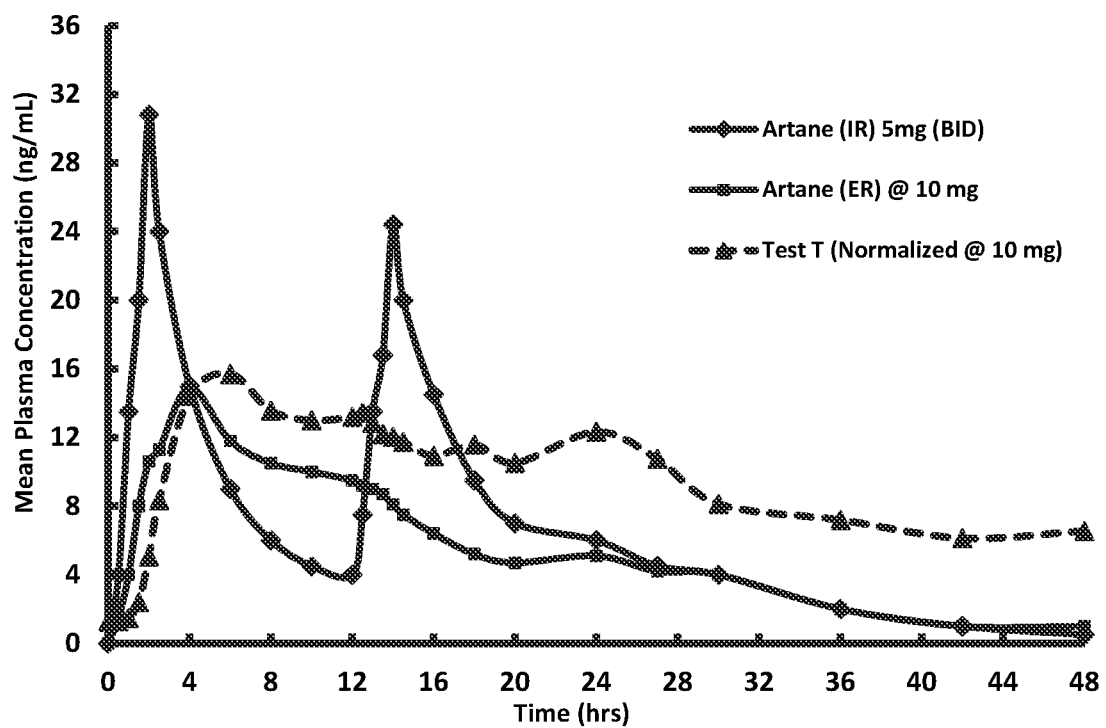

FIG. 8 compares pharmacokinetic data for Artane IR (5 mg BID), and Artane ER (10 mg QD) (see, Cheung et al. (1988), supra) with a 5 mg extended release composition of the disclosure (Test T) (normalized at 10 mg). FIG. 8 demonstrates that Test T provided sustained release of THP over an extended time period compared to Artane IR (5 mg BID) and Artane ER (10 mg QD).

Figure 9:
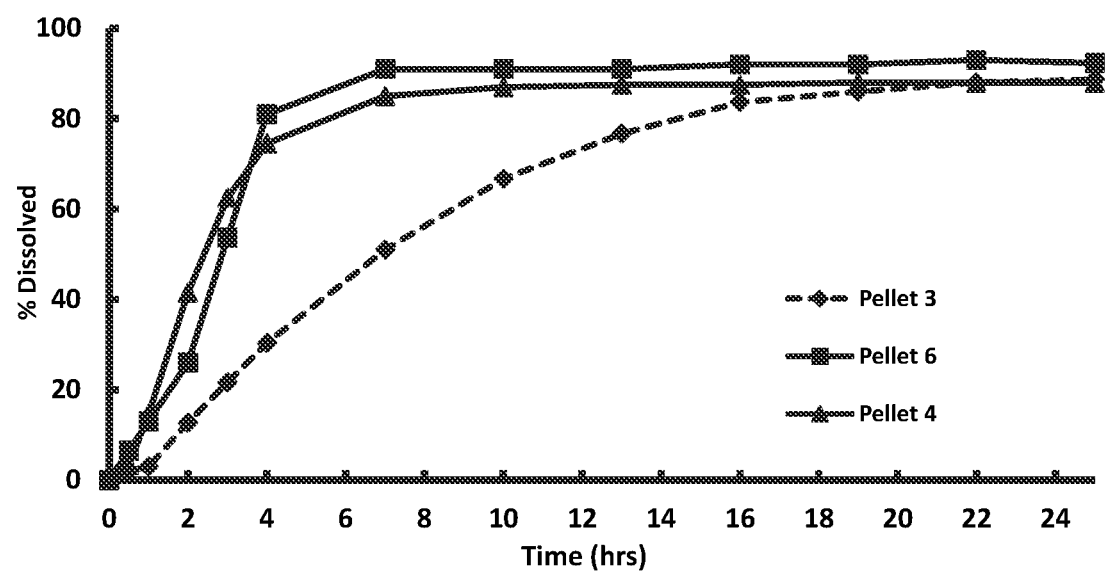

FIG. 9 compares a two-stage dissolution profile of Pellets 3, 4, and 6, performed using USP Apparatus I at 100 RPM and 37° C., in 900 ml of pH 1.2 HCl for 1 hour followed by dissolution in 900 ml of pH 6.8 phosphate buffer for 24 hours. FIG. 9 demonstrates that Pellet 3, containing ethyl cellulose and hypromellose phthalate (HP 55), provided better controlled release of the drug compared to Pellet 4, containing ethyl cellulose and hypromellose (Methocel E5

Prem LV), and Pellet 6 containing Eudragit S100 and hypromellose phthalate (HP 55) in the functional coat.

Figure 10:
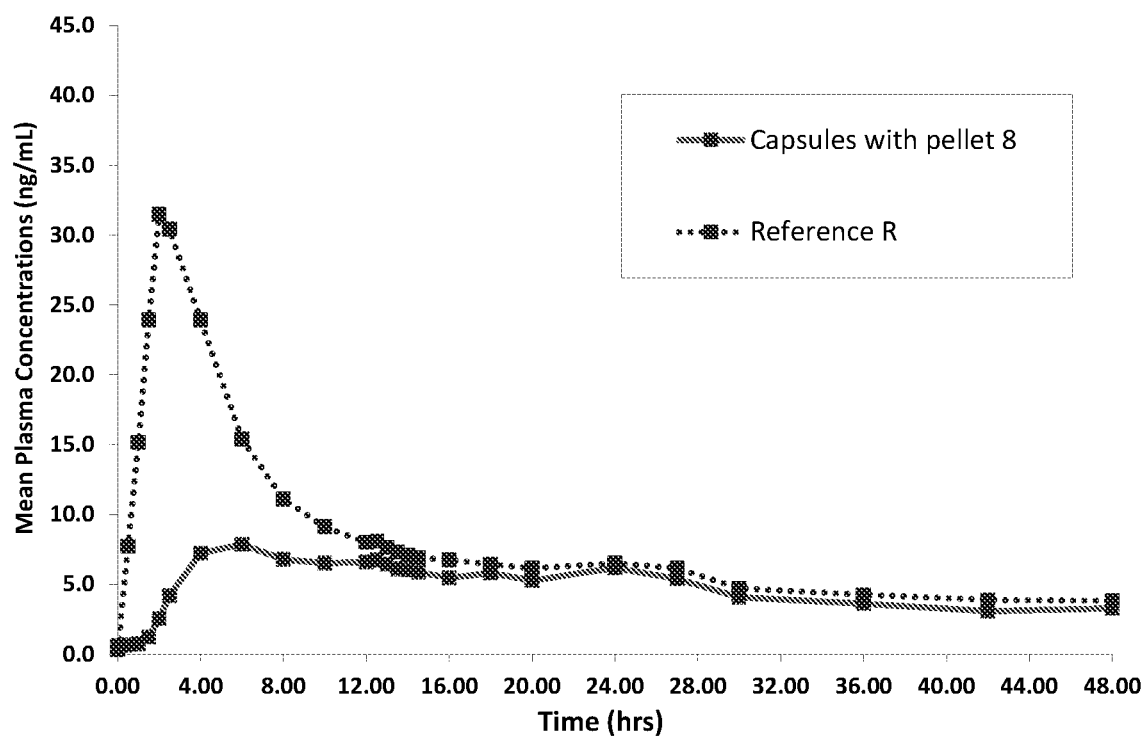

FIG. 10 compares PK performance of extended release THP HCl capsules containing Pellet 8 (5 mg, QD dosing) of the present disclosure with a marketed immediate release THP HCl product (5 mg, QD dosing). The figure demonstrates that the extended release THP capsules provided reduced initial burst release, while providing therapeutic concentrations of THP HCl over at least about 16 hours, compared to marketed immediate release THP tablets. $C_{max}$ of the extended release capsules containing Pellet 8 was about 25% of the marketed immediate release product.

Figure 11:
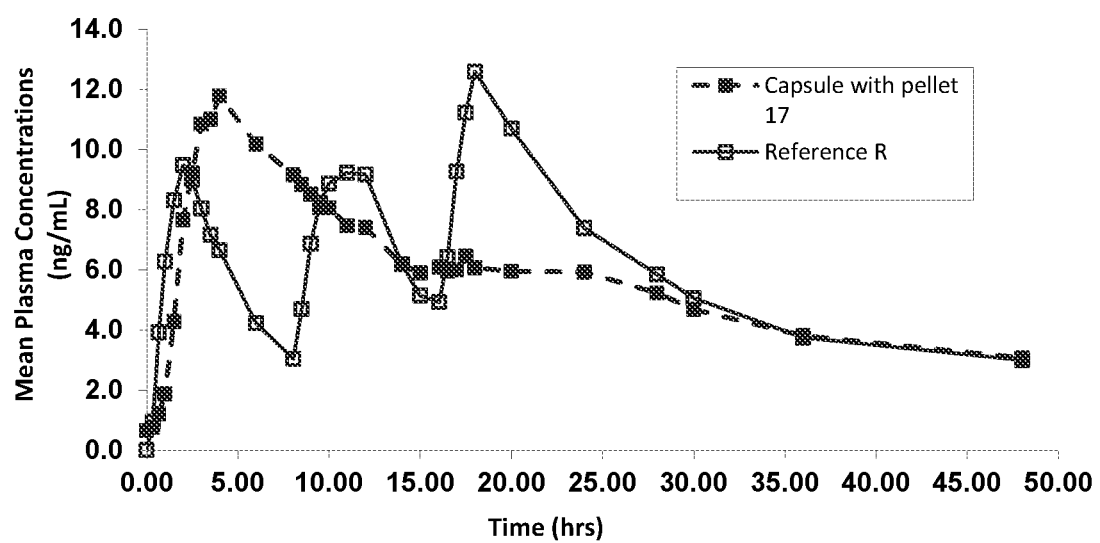

FIG. 11 compares PK performance of extended release THP HCl capsules containing Pellet 17 (pellet weight adjusted to 6 mg strength) of the present disclosure, administered once-a-day, with marketed immediate release THP HCl product (2 mg), administered 3 times-a-day. The figure demonstrates that the extended release THP capsules, administered once-a-day, provided substantially reduced $C_{max}$-to-$C_{min}$ fluctuations (e.g., $C_{min}:C_{max}$ ratio of $\geq 0.4$) compared to marketed immediate release 2 mg THP tablets administered three-times-a-day, while providing therapeutic concentrations of THP HCl over about 24 hours.

Figure 12:
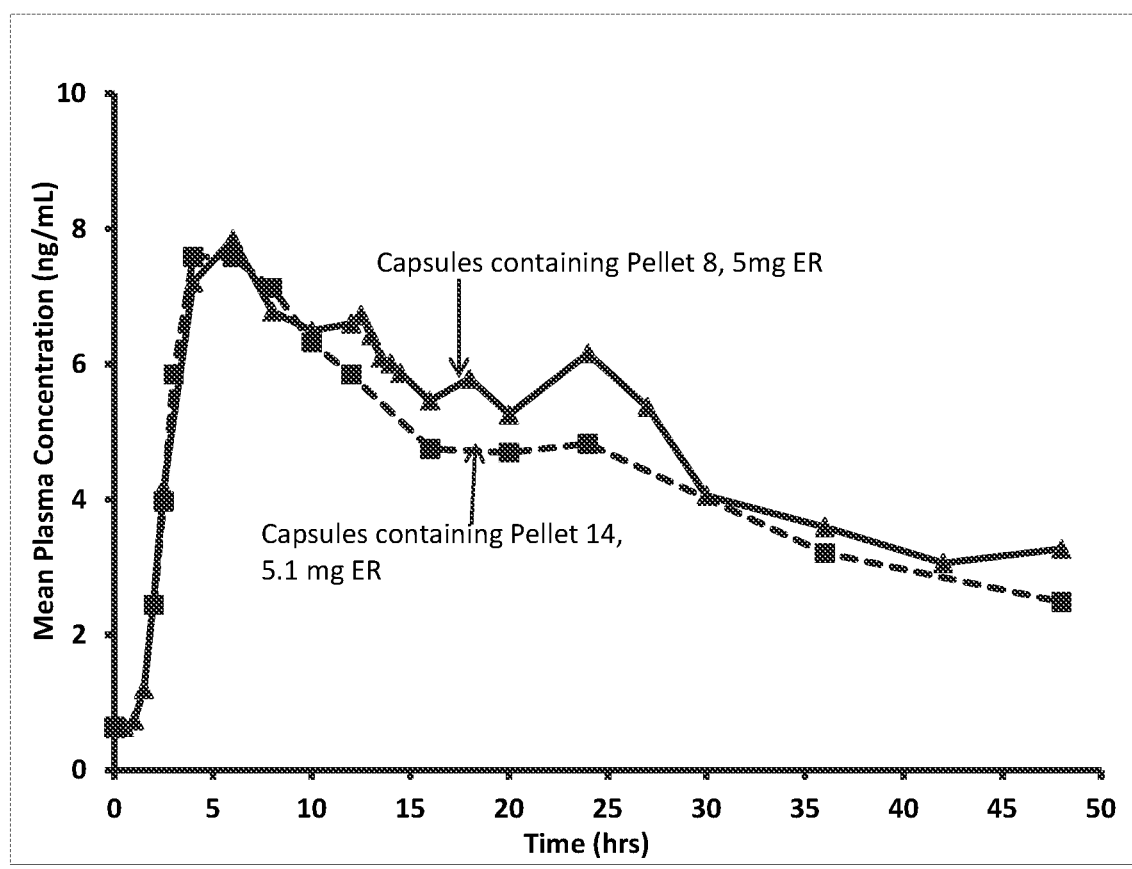

FIG. 12 compares pharmacokinetic data from a single dose PK study conducted in healthy volunteers, under fed conditions, for extended release THP HCl capsules containing functional coated Pellet 14 without IR drug layer (e.g., Pellet 14 without Seal Coat-2 and Drug Layer 2), and extended release THP HCl capsules containing Pellet 8. The extended release capsules used in the two PK studies contained THP HCl at a fill weight of ~5 mg, wherein the entire THP HCl was present in the extended release Drug Layer 1. FIG. 12 demonstrates that at a given strength, the compositions of the disclosure exhibit minimal inter-study variability in plasma concentration of THP over an extended time period, e.g., the PK profile of the composition is reproducible at a given strength.

Figure 13:
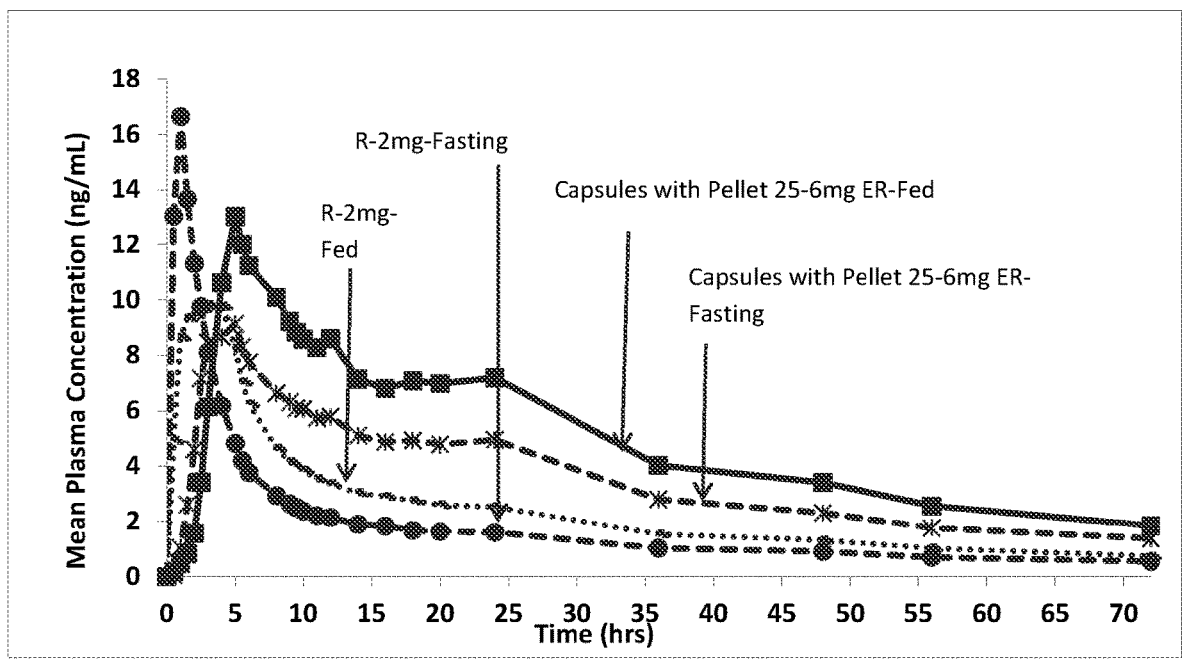

FIG. 13 compares pharmacokinetic data from a single dose pharmacokinetic (PK) study conducted in healthy volunteers, under fed and fasting conditions, for extended release THP capsules containing pellet 25 (6 mg THP HCl) of the present disclosure with a Reference Product (R)/marketed immediate release THP HCl tablet (2 mg THP). FIG. 13 demonstrates that the extended release THP capsules, QD dosing, in both fed and fasted conditions, provided substantially reduced $C_{max}$-to-$C_{min}$ fluctuations (e.g., $C_{min}:C_{max}$ ratio of $\geq 0.4$ and FI of $\leq 1$), while providing therapeutic concentrations of THP HCl over about 24 hours, compared to marketed immediate release 2 mg THP tablets, QD dosing.

Figure 14:
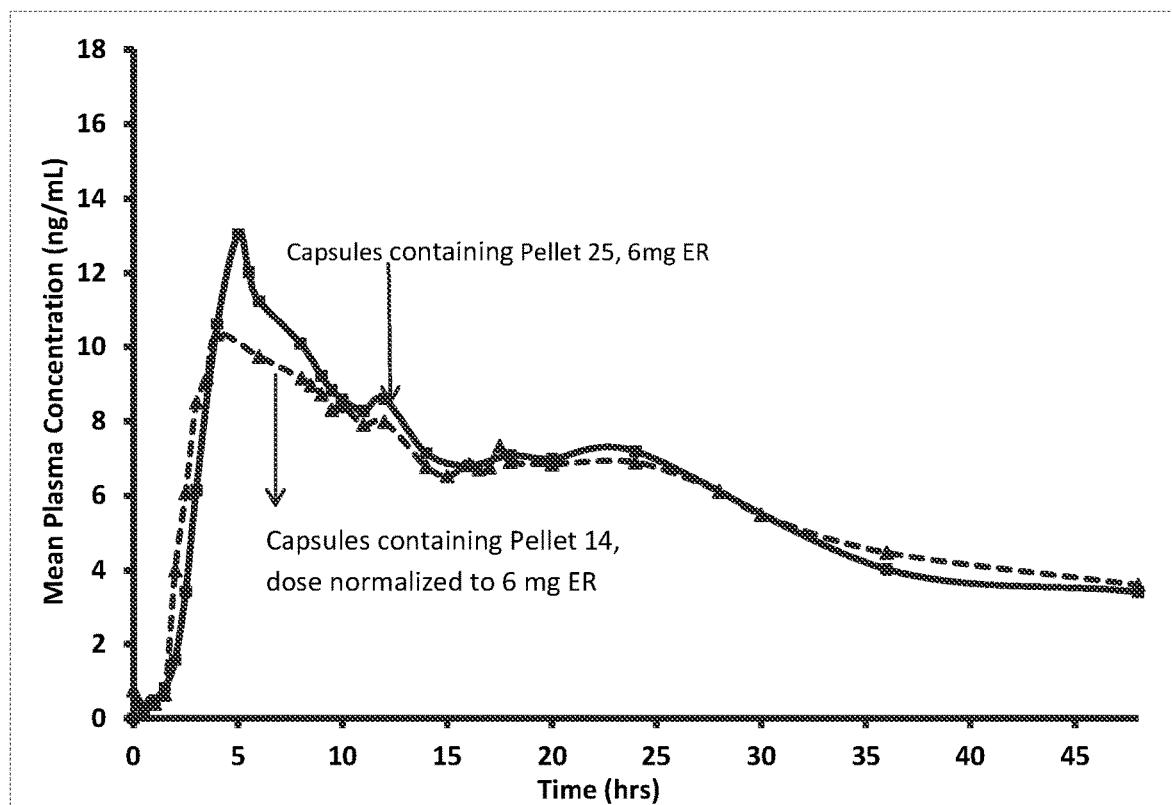

FIG. 14 compares pharmacokinetic data from a single dose pharmacokinetic (PK) study conducted in healthy volunteers, under fed conditions, for extended release THP HCl capsules containing Pellet 25 (6 mg THP HCl without Drug layer-2)), with capsules containing modified Pellet 14, (e.g., Pellet 14 without Seal Coat-2 and Drug Layer 2) and dose normalized to 6 mg. The extended release capsules used in the two PK studies contained THP HCl in the extended release Drug Layer 1. FIG. 14 demonstrates that at a given strength, the compositions of the disclosure exhibit minimal inter-study variability in plasma concentration of THP over an extended time period, e.g., the PK profile of the composition is reproducible at a given strength.

Figure 15:
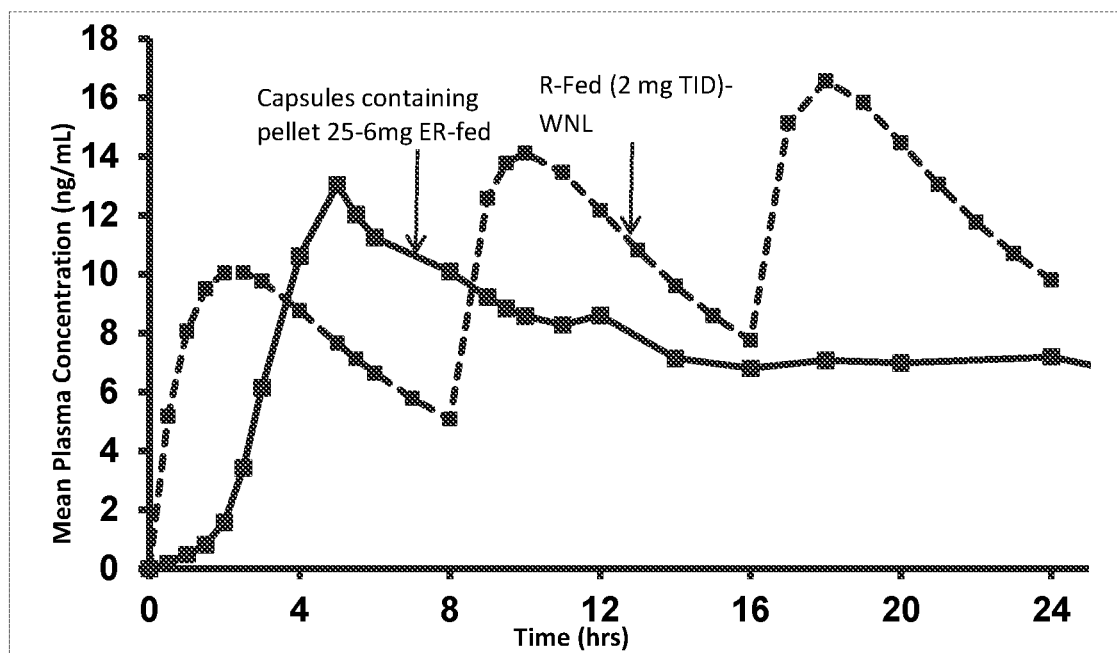

FIG. 15 compares PK data for extended release capsules containing Pellet 25 (6 mg THP HCl) and of reference product R (QD dose simulated for TID), in normal healthy adult human subjects under fed conditions. The data from FIG. 15 demonstrates that under fed conditions, the extended release THP capsules (6 mg), administered once-a-day, provided substantially reduced $C_{max}$-to-$C_{min}$ fluctuations(e.g., $C_{min}:C_{max}$ ratio of $\geq 0.4$ and FI of $\leq 1$), while providing therapeutic plasma concentrations of THP HCl over about 24 hours, compared to marketed immediate release 2 mg THP tablets administered three-times-a-day.

Figure 16:
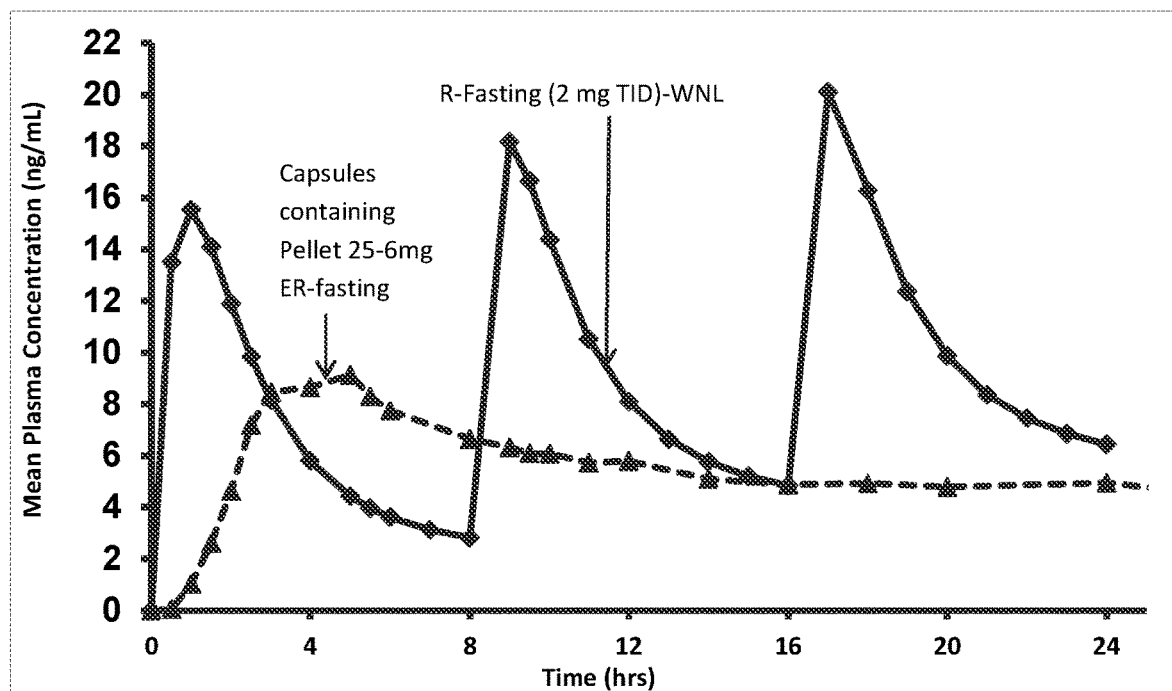

FIG. 16 compares PK data for extended release capsules containing Pellet 25 (6 mg THP) and of reference product R (QD dosed simulated for TID), in normal healthy adult human subjects under fasting conditions. The data from FIG. 16 demonstrates that under fasting conditions, the extended release THP capsules (6 mg), administered once-a-day, provided substantially reduced $C_{max}$-to-$C_{min}$ fluctuations (e.g., $C_{min}:C_{max}$ ratio of $\geq 0.4$ and FI of $\leq 1$), while providing therapeutic plasma concentrations of THP HCl over about 24 hours, compared to marketed immediate release 2 mg THP tablets administered three-times-a-day.

6. DETAILED DESCRIPTION

The presently disclosed subject matter provides ER trihexyphenidyl (e.g., THP HCl) compositions suitable for once- or twice-daily administration. The ER THP compositions of the disclosure reduce drug toxicity and drug-related side effects, compared to IR THP compositions, by reducing $C_{max}$, providing $C_{min}:C_{max}$ ratio of $\geq 0.4$ and FI of $\leq 1$, and providing consistent plasma levels of the drug by improving drug solubility at pH of greater than or equal to about 5.

The compositions of the disclosure provide membrane-controlled extended release of THP or a pharmaceutically acceptable salt thereof, wherein the membrane controls the drug release in the stomach and extends the release of the drug in lower regions of the gastrointestinal (GI) tract, wherein the pH is greater than or equal to about 5. The compositions of the disclosure provide an acid microenvironment within the dosage form to improve the solubility of THP or a pharmaceutically acceptable salt thereof, as the dosage form passes through the portions of the GI tract with a pH greater than or equal to about 5. The membrane-controlled extended release and the presence of an acid microenvironment within the dosage form to improve drug solubility, helps the dosage form to provide and maintain at least a minimum therapeutic plasma concentration of THP or a pharmaceutically acceptable salt thereof, while providing Cmin:Cmax ratio of $\geq 0.4$ and FI of $\leq 1$. The ER THP compositions of the disclosure include pellets suitable for dosing in capsules, sachets, sprinkling on food or liquid, and administration via feeding tube. In certain embodiments, the extended release compositions of the disclosure, with or without an immediate release drug layer (e.g., drug layer-2), are formulated to reduce fluctuations in plasma levels of trihexyphenidyl throughout the day (24-hour period), as compared to ARTANE® (2 mg TID) or ARTANE® (5 mg BID). In certain embodiments, the extended release dosage forms of the disclosure, with or without an immediate release drug layer, are formulated to reduce dose related peak-to-trough fluctuations (Fluctuation Index) in plasma levels of trihexyphenidyl. In certain embodiments, a decrease in Fluctuation Index indicates a decrease in drug plasma fluctuation between the peak-to-trough plasma levels (e.g., Cmax:Cmin ratio) of trihexyphenidyl; and an increase in Fluctuation Index indicates an increase in drug plasma fluctuation between the peak-to-trough plasma levels (e.g., Cmax:Cmin ratio) of trihexyphenidyl. A Fluctuation Index of zero indicates no fluctuations in drug plasma levels, e.g., as observed in intra venous infusion at steady state. In certain embodiments, the extended release trihexyphenidyl compositions of the disclosure, upon a single dose administration, provide a Fluctuation Index of ≤1, e.g., from about 0.1 to about 1. In certain embodiments, the extended release trihexyphenidyl compositions of the disclosure provide a Fluctuation Index (Cmax−Cmin/Cav) of about 0.1, about 0.2, about 0.3, about 0.4, about 0.5, about 0.6, about 0.7, about 0.8, about 0.9, about 1, or any intermediate values therein. In certain embodiments, the compositions of the disclosure provide extended release of THP, or a pharmaceutically acceptable salt thereof, for at least about 10 hours, e.g., from about 16 hours to about 24 hours, and exhibit a shelf life of at least about 2 years at controlled room temperature conditions.

In certain embodiments, the disclosure provides methods for making ER pellets of THP or a pharmaceutically acceptable salt thereof. In certain embodiments, the disclosure provides methods for making trihexyphenidyl capsules containing extended release THP pellets. In certain embodiments, the disclosure provides methods for improving patient compliance by administering to the patient an extended release THP composition that can provide extended release PK profile with reduced dose related peak-to-trough fluctuations, e.g., providing $C_{min}:C_{max}$ ratio of greater than or equal to 0.4 and/or Fluctuation Index of ≤1, for improved tolerability and reduced adverse effects associated with high plasma concentrations and high peak-to-trough fluctuations. In certain embodiments, the disclosure provides methods for improving patient compliance by administering to the patient an extended release THP composition that can be administered as pellets for dosing in capsules, sachets, administration with feeding tube, and as sprinkles on food. In certain embodiments, the disclosure provides methods of treating all forms of parkinsonism, e.g., postencephalitic, arteriosclerotic, and idiopathic parkinsonism, using extended release THP compositions of the disclosure. In certain embodiments, trihexyphenidyl hydrochloride compositions of the disclosure are used as adjuvant therapy with levodopa when treating the above-mentioned forms of parkinsonism. In certain embodiments, the disclosure provides methods for treating primary dystonia, dystonia associated with cerebral palsy (dyskinetic cerebral palsy), and/or sialorrhea, using extended release THP compositions of the disclosure. In certain embodiments, the THP compositions of the disclosure are used for controlling extrapyramidal disorders caused by central nervous system drugs such as dibenzoxazepines, phenothiazines, thioxanthenes, and butyrophenones.

For clarity and not by way of limitation, this detailed description is divided into the following subportions:

5.1. Definitions;
5.2. Formulations of Pellet Dosage Forms;
5.3. Compositions;
5.4. Methods of Making; and
5.5. Methods of Use.

6.1. Definitions

The terminology used in the present disclosure is for the purpose of describing particular embodiments only and is not intended to be limiting. Certain terms are discussed below, or elsewhere in the specification, to provide additional guidance in describing the compositions and methods of the disclosure and how to make and use them. Unless otherwise defined, all terms, including technical and scientific terms used in the description, have the same meaning as commonly understood by one of ordinary skill in the art to which this disclosure belongs.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing," and "comprising" are interchangeable, and one of skill in the art is cognizant that these terms are open-ended terms.

As used herein, "and/or" refers to and encompasses any and all possible combinations of one or more of the associated listed items.

The term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 15%, up to 10%, up to 5%, up to 1%, up to 0.5%, or even up to 0.1% of a given value.

As used herein, a "therapeutically effective," "therapeutic," or "therapeutically acceptable" amount refers to an amount that will elicit a therapeutically useful response in a subject and includes an additional amount or overage of active ingredient deemed necessary in the formulation to provide the desired amount upon administration. The therapeutically useful response can provide some alleviation, mitigation, and/or decrease in at least one clinical symptom in the subject. Those skilled in the art will appreciate that the therapeutically useful response need not be complete or curative, as long as some benefit is provided to the subject. In some embodiments, the subject is a human. In certain embodiments, a "therapeutically effective," "therapeutic," or "therapeutically acceptable" amount refers to a dose that produces a plasma level of THP, or a pharmaceutically acceptable salt thereof, from about 1 ng/ml to about 20 ng/ml, based on the strength of the THP composition.

As used herein, the term "drug recovery" refers to percentage of the total amount of drug present in the dosage form that is released in a dissolution medium. The term "complete drug recovery" refers to release of about 90% to about 105% of the drug present in the dosage form.

The term "burst release," as used herein, refers to release of THP or a salt thereof in an amount that is outside (i.e., above) the therapeutic range of THP, and providing the drug plasma concentration level that can result in various unwanted side effects. The term "therapeutic range" includes a range of the amount of drug that will elicit a therapeutically useful response in a subject and includes an additional amount or overage of active ingredient deemed necessary in the formulation to provide the desired amount upon administration.

As used herein, the terms "drug layer," "drug layer-1," and "first drug layer," as used interchangeably herein, refer to one or more layers/drug layers (e.g., at least one drug layer) comprising THP or a pharmaceutically acceptable salt thereof. In certain embodiments, the drug layer-1 is located between the acid core and the functional coating and provides extended release of THP or a pharmaceutically acceptable salt thereof. Likewise, the terms "drug layer-2" and "second drug layer," as used interchangeably herein, refer to one or more drug layers comprising THP or a pharmaceutically acceptable salt thereof. In certain embodiments, drug layer-2 is located above and covering at least a portion of the functional coat and provides an immediate release of THP or a pharmaceutically acceptable salt thereof. In certain embodiments in which only one drug layer is present, that drug layer will be drug layer-1.

The term "coating weight gain", as used herein, refers to coating weight gain with respect to the weight of the uncoated tablet. For example, a coating weight gain of 15% refers to a 15% w/w increase in tablet weight during coating with respect to the uncoated tablet weight.

As used herein, the terms "extended release" and "sustained release" are used interchangeably and refer to dosage forms or compositions that are formulated to maintain relatively consistent drug concentrations in plasma during a dosing interval comprising an extended period of time (i.e., post-administration), as compared to the drug administered as an immediate release dosage form. The extended release/sustained release dosage forms allow the drug to be available over an extended period of time after administration, thereby allowing a reduction in dosing frequency, as compared to a drug presented as an immediate release dosage form.

The term "release rate", as used herein, refers to the quantity of drug released per unit time, e.g., mg of drug released per hour (mg/hour), from a dosage form. In certain embodiments, drug release rates can be calculated under in vitro dosage form dissolution testing conditions known in the art.

The term "immediate release," as used herein, refers to release of at least 70% of a drug in about one hour or less, preferably within 30 minutes or less, post-administration.

The term "semipermeable," as used herein, refers to a membrane containing sparingly soluble polymers, or insoluble polymers, with or without a pore former(s) that will allow fluids to pass through membrane by diffusion. The permeability of the membranes increases with the dissolution of the pore former(s). As used herein, the terms functional coat and semipermeable membrane are used interchangeably.

The terms "pore former" and the like, as used herein, refer to pH-dependent or pH-independent water-soluble polymers and/or water-soluble small molecules that will form pores or channels (i.e., behave as a channeling agent) in a coating, e.g., functional coat/membrane, thereby creating a permeable functional coat/membrane. The term "pore former" includes molecules used to create a certain amount of diffusion through the semipermeable membrane/coating of a tablet, pellet, or particle to achieve a sustained release profile. In certain embodiments, the pore former includes nonionic water-soluble polymers. In certain embodiments, the pore former includes enteric polymers.

The terms "core," "acid core," "organic acid core," "core comprising an organic acid," or "core comprising at least one organic acid," as used interchangeably herein, refer to a core (e.g., pellet, bead/seed, or granule) comprising at least one organic acid; a core (e.g., pellet, bead/seed, or granule) coated with at least one coating comprising at least one organic acid; or a core that is an organic acid or a mixture of organic acids.

The term "acid coated core" refers to an inert substrate/non-pareil seed, which is layered/coated with at least one coating comprising at least one organic acid.

In certain embodiments, the terms "inert substrate," and "non-pareil seed," as used interchangeably herein, refers to inert material/particles, e.g., pellets, beads, seeds, or granules. In some embodiments, the non-pareil seeds are composed of inert substrates such as starch, sugar, lactose, and/or cellulose. In certain embodiments, the non-pareil seeds comprise sugar spheres or microcrystalline cellulose/cellets.

The terms "gastric fluid," and "GI fluid," as used interchangeably herein, refer to medium occurring in the stomach and lower gastrointestinal tract of an individual.

The terms "simulated gastric fluid," and "SGF," as used interchangeably herein, refers to a medium that is used to mimic the chemical environment of gastric fluid/medium in an in vitro setting.

As used herein, the term "dissolution medium" refers to a medium used to mimic pH of gastric fluid/medium in stomach or lower gastrointestinal tract of an individual. In certain embodiments, the medium used to mimic chemical environment of stomach of an individual includes a medium with pH of less than about 5.5, e.g., about 1, about 1.25, about 1.5, about 1.75, about 2, about 2.25, about 2.5, about 2.75, about 3, about 3.25, about 3.5, about 3.75, about 4.0, about 4.25, about 4.5, about 4.75, about 5.0, about 5.5, or any intermediate values therein. In certain embodiments, the medium used to mimic chemical environment of lower GI tract of an individual includes a medium with pH of from about 5.5 to about 8, e.g., about 5.5, about 5.75, about 6.0, about 6.25, pH 6.5, about 6.75, about 7, about 7.25, about 7.5, or any intermediate values therein.

The term "bioavailability" refers to the fraction of an administered dose of unchanged drug that reaches the systemic circulation.

The term "substantially free," as used herein, refers to an amount comprising less than 0.001 wt % of the material.

The term "microenvironment," as used herein, refers to immediate environment of the drug, e.g., THP or a pharmaceutically acceptable salt thereof, within the pellet.

The term "acid microenvironment" refers to immediate drug environment (e.g., microenvironment of THP or a pharmaceutically acceptable salt thereof) with a pH of less than about 5.

As used herein, the term "therapeutic concentration" refers to a plasma concentration of THP or a pharmaceutically acceptable salt thereof from about 1 ng/ml to about 20 ng/ml, based on the strength of the composition and the condition.

The terms "Fluctuation Index" and "FI," as used interchangeably herein with respect to the trihexyphenidyl compositions refer to fluctuations in plasma levels of trihexyphenidyl or a pharmaceutically acceptable salt thereof released from the composition during a 24-hour dosing period. Fluctuation Index provides a quantitative measurement of fluctuation in drug plasma concentration, measured as dose related peak-to-trough fluctuations. Fluctuation Index is calculated using the formula: $FI = (C_{max} - C_{min})/C_{av}$, wherein $C_{max}$ is the maximum plasma concentration of the drug, e.g., trihexyphenidyl or a pharmaceutically acceptable salt thereof; $C_{min}$ is the minimum plasma concentration of the drug; and $C_{av}$ is the average plasma concentration of the drug. The term "$C_{av}$," as used herein with respect to the trihexyphenidyl compositions, for example marketed IR trihexyphenidyl tablets, e.g., Artane IR (5 mg BID), and Artane IR (2 mg TID), and compositions of the disclosure, refers to average plasma concentration of trihexyphenidyl or a pharmaceutically acceptable salt thereof, during a 24-hour dosing period.

As used herein, the terms "treatment," "treat," and "treating" refer to reversing, alleviating, delaying the onset of, and/or inhibiting the progress of a disease or disorder as described herein. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example to prevent or delay their recurrence.

As used herein, the terms "trihexyphenidyl" and "trihexyphenidyl hydrochloride" are used interchangeably herein. The term "trihexyphenidyl" includes all pharmaceutically acceptable salts, esters, and functionally equivalent chemical compounds, including trihexyphenidyl hydrochloride.

As used herein, the terms "up," "down," "above," "below," "top," "bottom," etc. should be interpreted as nonlimiting upon the pellets, cores, layers, methods, and products of any methods of present disclosure, which can be spatially arranged in any orientation or manner.

6.2. Formulations of Pellet Dosage Forms

The present disclosure provides extended release oral trihexyphenidyl compositions that maintain solubility of the drug in different pH environments of the GI tract and maintain at least a minimum therapeutic plasma concentration of the drug for extended periods of time, without an initial spike or burst in release of the drug.

Trihexyphenidyl is commonly prescribed as trihexyphenidyl hydrochloride. However, use of other pharmaceutically acceptable salts of trihexyphenidyl is also contemplated in the present disclosure.

Pharmaceutically acceptable salts of trihexyphenidyl known in the art include, but are not limited to, hydrochloride, hydrobromide, hydroiodide, bromide, sulfite, sulfate, bisulfate, nitrate, salicylate, citrate, tartrate, bitartrate, lactate, phosphate, malate, maleate, fumarate, succinate, acetate, and pamoate salts.

In certain embodiments, the present disclosure provides for compositions that comprise THP and are able to maintain plasma concentrations of THP at about 80% of $C_{max}$ for an average time period of about 6 hours, at about 70% of $C_{max}$ for an average time period of about 8 hours, at about 60% of $C_{max}$ for an average time period of about 12 hours, and at about 50% of $C_{max}$ value for an average time period of about 24 hours post-administration of the extended release THP composition, compared with values of about 80% of $C_{max}$ at 3 hours, about 70% of $C_{max}$ at 4 hours, and about 30% $C_{max}$ at about 8 hours post-administration of an immediate release THP composition.

In certain embodiments, compositions of the present disclosure comprise THP extended release pellets. In certain embodiments, the compositions described herein comprise capsules containing extended release pellets. In certain embodiments, the extended release pellets comprise an acid core coated with a seal coat, a drug layer over the seal coat, and a functional coat/membrane over the drug-layered core. In certain embodiments, the presence of seal coat is optional. In certain embodiments, the acid core is a nonpareil seed (e.g., cellet/microcrystalline cellulose, sugar sphere) layered with at least one coating layer comprising at least one organic acid. In certain embodiments, the compositions of the disclosure comprise at least one immediate release drug layer (drug layer-2) over the functional coat. In certain embodiments, the compositions of the disclosure comprise a seal coat (seal coat-2) between the functional coat and drug layer-2. In certain embodiments, the compositions of the disclosure comprise an over coat over drug layer-2. In certain embodiments, the presence of seal coat-2 and/or over coat is optional. Each component of the compositions of the present disclosure is described in more detail below.

In certain embodiments, the present disclosure provides pellets comprising a core that comprises at least one organic acid. The organic acid in the core provides an acidic microenvironment around trihexyphenidyl to increase solubility of trihexyphenidyl, which is a weak base with poor solubility at a pH of greater than or equal to about 5. In certain embodiments, the core is spherical or irregular in shape. In certain embodiments, the core is a pellet, bead/seed, or a granule comprising at least one organic acid. In certain embodiments, the core is a pellet, bead/seed, or a granule coated with at least one coating comprising at least one organic acid. In certain embodiments, the core is an organic acid or a mixture of organic acids. In a specific embodiment, organic acid granules are used as the core. In certain embodiments, the core is an acid coated core comprising a nonpareil seed coated with at least one coating comprising at least one organic acid, e.g., a cellet/sugar sphere coated with an organic acid. In certain embodiments, the core is a microcrystalline cellulose sphere, or a sugar sphere coated with at least one coating comprising at least one organic acid. In certain embodiments, the organic acid coat over the nonpareil seed contains trihexyphenidyl or a pharmaceutically acceptable salt thereof. In certain embodiments, the organic acid core is coated with a coat containing trihexyphenidyl or a pharmaceutically acceptable salt thereof, and at least one additional organic acid. In certain embodiments, the additional organic acid in the coating can be same as the organic acid present in the core. In certain embodiments, the additional organic acid in the coating can be different from the organic acid present in the core.

In certain embodiments, the organic acid in the core provides acid microenvironment for protonating trihexyphenidyl in alkaline pH present in the lower GI tract, e.g., intestine. As protonated THP is more soluble than THP free base, therapeutic plasma concentrations of the THP are maintained as the dosage form travels through the intestine. In certain embodiments, the organic acid in the core improves in vivo solubility and plasma levels of the THP. In certain embodiments, the compositions of the present disclosure maintain a therapeutically effective plasma concentration of trihexyphenidyl for extended time periods.

Without being bound to any particular theory, the organic acid in the core is believed to enhance the dissolution and absorption of trihexyphenidyl throughout the GI tract, especially in the lower GI tract with pH of >5. The organic acid in the core lowers the microenvironmental pH within the pellet and solubilizes THP. As the microenvironmental pH within the pellet drops, the trihexyphenidyl is protonated and solubilized for absorption in the GI tract.

In certain embodiments, the core consists of one or more organic acids. In certain embodiments, the organic acid in the core is present in an amount of from about 5% to about 100%, from about 20% to about 80%, from about 30% to about 70% w/w, or any intermediate values thereof, based on the total weight of the core. In certain embodiments, the organic acid is present in amount of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or 100% w/w, based on the total weight of the core.

In certain embodiments, the core makes up from about 40% to about 99%, from about 50% to about 95%, from about 60% to about 90% w/w, or any intermediate values thereof, of the total weight of the composition of the present disclosure. In certain embodiments, the core makes up at least about 40%, at least about 42.5%, at least about 45%, at least about 47.5%, at least about 50%, at least about 52.5%, at least about 55%, at least about 57.5%, at least about 60%, at least about 62.5%, at least about 65%, at least about 67.5%, at least about 70%, at least about 72.5%, at least about 75%, at least about 77.5%, at least about 80%, at least about 82.5%, at least about 85%, at least about 87.5%, at least about 90% w/w, at least about 92.5%, at least about 95%, at least about 97.5%, or at least about 99% w/w, of the total weight of the composition of the present disclosure.

In certain embodiments, the organic acid is one or more of tartaric acid, citric acid, fumaric acid, succinic acid, malic acid, or any combinations thereof. In certain embodiments, the organic acid is crystalline tartaric acid.

In certain embodiments, the compositions of the present disclosure provide excellent stability and bioavailability of trihexyphenidyl hydrochloride for extended periods of time. The excellent stability and bioavailability of trihexyphenidyl hydrochloride is at least in part provided by the presence of an organic acid that ensures trihexyphenidyl remains solubilized for extended periods of time after oral administration, even in a weakly acidic, neutral, or basic environment.

6.2.2. Seal Coats and Over Coat

In certain embodiments, the core is coated with at least one seal coat. In certain embodiments, the seal coat is optional. In certain embodiments, the pellets can include two seal coats (seal coat-1 between the core and drug layer-1, and the seal coat-2 between the functional coat and drug layer-2). In certain embodiments, the pellets include at least one over coat. In certain embodiments, the presence of seal coat-2 and/or the overcoat is optional. In certain embodiments, pellets containing one drug layer (e.g., drug layer-1) do not contain seal coat-2 and over coat. In certain embodiments, the pellets containing drug layer-1 include various components and coats in the following order: a core; seal coat-1 over the core and covering at least a portion of the core; drug layer-1, containing THP for extended release, over seal coat-1 and covering at least a portion of seal coat-1; and a functional coat over drug layer-1 and covering at least a portion of drug layer-1. In certain embodiments, the pellets containing drug layer-1 further include seal coat-2 over the functional coat. In certain embodiments, the pellets containing drug layer-1 further include an over coat over seal coat-2. In certain embodiments, the pellets containing at drug layer-1 and drug layer-2 include various components and coats in the following order: a core; seal coat-1 over the core and covering at least a portion of the core; drug layer-1, containing THP for extended release, over seal coat-1 and covering at least a portion of seal coat-1; and a functional coat over drug layer-1 and covering at least a portion of drug layer-1, seal coat-2 over the functional coat and covering at least a portion of the functional coat; drug layer-2, containing THP for immediate release, over seal coat-2 and covering at least a portion of seal coat-2; and an overcoat over drug layer-2 and covering at least a portion of drug layer-2. In certain embodiments, the each of the seal coat-1, the seal coat-2, and/or the over coat are present at a coating weight gain of between 0% and about 10% w/w, based on the total weight of the corresponding pellet without the corresponding coats (e.g., pellets without seal coat-1, seal coat-2, and/or the over coat). In certain embodiments, each of the seal coat-1, the seal coat-2, and/or the over coat are present at a coating weight gain of about 0.5%, about 1%, about 2%, about 3%, about 4%, about 5%, about 6%, about 7%, about 8%, about 9%, about 10% w/w, or any intermediate values therein, based on the total weight of the corresponding pellet without seal coat-1, seal coat-2, and/or the over coat. In certain embodiments, coating solvents used for coating the seal coat and/or the over coat comprise, but are not limited to, an organic solvent, water, and/or any mixtures thereof. In certain embodiments, the coating solvent is a mixture of an organic solvent and water. In certain embodiments, organic solvent:water weight ratio is between 60:40 and 98:2. In certain embodiments, the organic solvent:water weight ratio is about 60:40, about 70:30, about 75:25, 80:20, about 85:15, about 90:10, about 95:5, about 98:2, or any intermediate values therein. In certain embodiments, the coating solvents comprise organic solvents selected from the group consisting of methylene chloride, carbon tetrachloride, acetone, methanol, ethanol 200 proof, and/or any mixtures thereof. In certain embodiments, coating solvents comprise, but are not limited to, methylene chloride, carbon tetrachloride, acetone, methanol, ethanol 200 proof, water, and/or any mixtures thereof. In certain embodiments, the coating solvent is a mixture of ethanol 200 proof and water. In certain embodiments, ethanol:water weight ratio is between 60:40 and 98:2. In certain embodiments, the ethanol:water weight ratio is about 60:40, about 70:30, about 75:25, 80:20, about 85:15, about 90:10, about 95:5, about 98:2, or any intermediate values therein.

In certain embodiments, the seal coat(s) and over coat comprise a nonionic water-soluble polymer. In certain embodiments, the nonionic water-soluble polymer is selected from a group comprising hydroxypropyl cellulose, methyl cellulose, hydroxypropyl methylcellulose, hydroxyethyl cellulose, polyethylene glycol, polyvinyl alcohol, poloxamer, polyvinyl pyrrolidone-vinyl acetate copolymer (e.g., copovidone), and mixtures thereof. In certain embodiments, the amount of the nonionic water-soluble polymer ranges from about 5% to about 100% w/w, based on the total weight of the seal coat/over coat composition. In certain embodiments, the amount of the nonionic water-soluble polymer ranges from about 10% to about 95%, from about 15% to about 90%, from about 20% to about 85%, from about 25% to about 80%, from about 30% to about 75%, from about 35% to about 70%, from about 40% to about 65%, from about 45% to about 60%, or from about 50% to about 55% w/w, based on the total weight of the seal coat/over coat composition. In certain embodiments, the nonionic water-soluble polymer is present in an amount of about 70%, about 71%, about 72%, about 73%, about 74%, about 75%, about 76%, about 77%, about 78%, about 79%, about 80% w/w, or any intermediate values therein, based on the total weight of the seal coat/over coat composition.

In certain embodiments, the composition of the seal coat/over coat further comprises additional excipients, such as anti-tacking agents and/or plasticizers. In certain embodiments, anti-tacking agents include, but are not limited to, silicon dioxide (SYLOID® 244FP), fumed silica (CAB-O-SIL®), talc, kaolin, magnesium trisilicate, powdered starch, tribasic calcium phosphate, and any combinations thereof. In certain embodiments, the anti-tacking agent can be present in an amount of from about 5% to about 35% w/w, based on the total weight of the nonionic water-soluble polymer present in the seal coat/over coat composition. In certain embodiments, the anti-tacking agent is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35% w/w, or any intermediate values therein, based on the total weight of the nonionic water-soluble polymer present in the seal coat/overcoat composition. In certain embodiments, the plasticizers include, but are not limited to, glycerin, polyethylene glycol monomethyl ether, triethyl citrate, triacetin, polyethylene glycol, propylene glycol, sorbitol sorbitan solution, dibutyl sebacate, or mixtures thereof. In certain embodiments, the plasticizer is triethyl citrate. In certain embodiments, the plasticizer is dibutyl sebacate. In certain embodiments, the plasticizer is present in an amount of about 0%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% w/w, or any intermediate values therein, based on the total weight of the nonionic water-soluble polymer present in the seal coat/over coat composition. In certain embodiments, the seal coat/over coat is substantially free of a plasticizer. In certain embodiments, the amount of the additional excipients, when present, can range from about 0.1% to about 40%, from about 1% to about 35%, from about 2% to about 30%, from about 3% to about 25%, or from about 4% to about 20% w/w, based on the total weight of the nonionic water-soluble polymer; and in some embodiments from about 0.5% to about 25% w/w, based on the total weight of the nonionic water-soluble polymer present in the seal coat/over coat composition. In certain embodiments, the additional excipients are present in amount of at least about 1%, at least about 5%, at least about 10%, at least about 15%, at least about 20%, at least about 25%, at least about 30% w/w, at least about 35%, or any intermediate values therein, based on the total weight of the nonionic water-soluble polymer present in the seal coat/over coat composition.

6.2.3. Drug Layer

In certain embodiments, the core or a core coated with at least one seal coat is further coated with at least one drug layer. In certain embodiments, the drug layer covers at least a portion of the core. In certain embodiments, the drug layer comprises trihexyphenidyl or a pharmaceutically acceptable salt thereof and a nonionic water-soluble polymer. In certain embodiments, the drug layer further comprises at least one organic acid. In certain embodiments, the organic acid includes, but is not limited to, tartaric acid, citric acid, fumaric acid, succinic acid, malic acid, and mixtures thereof. In certain embodiments, coating solvents used for coating the drug layer comprise, but are not limited to, an organic solvent, water, and/or any mixtures thereof. In certain embodiments, the coating solvent is a mixture of an organic solvent and water. In certain embodiments, organic solvent: water weight ratio is between 60:40 and 98:2. In certain embodiments, the organic solvent:water weight ratio is about 60:40, about 70:30, about 75:25, 80:20, about 85:15, about 90:10, about 95:5, about 98:2, or any intermediate values therein. In certain embodiments, the coating solvents comprise organic solvents selected from the group consisting of methylene chloride, carbon tetrachloride, acetone, methanol, ethanol 200 proof, and/or any mixtures thereof. In certain embodiments, coating solvents comprise, but are not limited to, methylene chloride, carbon tetrachloride, acetone, methanol, ethanol 200 proof, water, and/or any mixtures thereof. In certain embodiments, the coating solvent is a mixture of ethanol 200 proof and water. In certain embodiments, ethanol:water weight ratio is between 60:40 and 98:2. In certain embodiments, the ethanol:water weight ratio is about 60:40, about 70:30, about 75:25, 80:20, about 85:15, about 90:10, about 95:5, about 98:2, or any intermediate values therein.

In certain embodiments, the pellets comprise at least one first drug layer, which is an extended release drug layer (drug layer-1) and at least one second drug layer, which is an immediate release drug layer (drug layer-2). In certain embodiments, drug layer-1 can comprise one or more drug layers. In certain embodiments, drug layer-2 can comprise one or more drug layers. In certain embodiments, the weight ratio of trihexyphenidyl or a pharmaceutically acceptable salt thereof in the extended release drug layer-1 and the immediate release drug layer-2 is from about 70:30 to about 100:0. In certain embodiments, the weight ratio of trihexyphenidyl or a pharmaceutically acceptable salt thereof in the extended release drug layer-1 and the immediate release drug layer-2 is about 70:30, about 75:25, about 80:20, about 85:15, about 90:10, about 95:5, about 100:0, or any intermediate ratios therein. In certain embodiments, drug layer-1 is positioned between seal coat-1 and the functional coat. In certain embodiments, there is no seal coat between the core and drug layer-1. In certain embodiments, the functional coat controls the release of trihexyphenidyl or a pharmaceutically acceptable salt thereof from drug layer-1. In certain embodiments, drug layer-2 is positioned between seal coat-2 and the over coat. In certain embodiments, there is no seal coat-2 between the functional coat and drug layer-2.

In certain embodiments, drug layer-1 comprises from about 1 mg to about 20 mg of trihexyphenidyl or a pharmaceutically acceptable salt thereof. In certain embodiments, the drug layer-1 comprises about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, or any intermediate values therein, of trihexyphenidyl pr a pharmaceutically acceptable salt thereof. In certain embodiments, drug layer-2 comprises from about 0 mg to about 1.5 mg of trihexyphenidyl or a pharmaceutically acceptable salt thereof. In certain embodiments, drug layer-2 comprises about 0.1 mg, 0.2 mg, about 0.3 mg, about 0.4 mg, about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, or any intermediate values therein, of trihexyphenidyl or a pharmaceutically acceptable salt thereof. In certain embodiments, the trihexyphenidyl or a pharmaceutically acceptable salt thereof is present in a concentration of from about 10% to about 70%, from about 15% to about 65%, from about 20% to about 60%, from about 25% to about 55%, or from about 30% to about 50% w/w, based on the total weight of the drug layer (drug layer-1 and drug layer-2) composition. In certain embodiments trihexyphenidyl or a pharmaceutically acceptable salt thereof is present in a concentration of from about 10% to about 80% w/w, based on the total weight of drug layer-1. In certain embodiments trihexyphenidyl or a pharmaceutically acceptable salt thereof is present in a concentration of about 20%, about 25%, about 30%, about 35%, about 40%, about 45%, about 50%, about 51%, about 52%, about 53%, about 54%, about 55%, about 56%, about 57%, about 58%, about 59%, about 60%, about 65%, about 70%, about 75%, about 80% w/w, or any intermediate values therein, based on the total weight of the drug layer-1 (extended release drug layer) composition. In certain embodiments trihexyphenidyl or a pharmaceutically acceptable salt thereof is present in a concentration of from about 5% to about 50% w/w, based on the total weight of drug layer-2 composition. In certain embodiments trihexyphenidyl or a pharmaceutically acceptable salt thereof is present in a concentration of about 5%, about 10%, 15%, about 20%, about 25%, about 30%, about 35%, about 40%, about 45%, about 50% w/w, or any intermediate values therein, based on the total weight of the drug layer-2 (immediate release drug layer) composition. In certain embodiments, trihexyphenidyl or a pharmaceutically acceptable salt thereof is present in a concentration of from about 1% w/w to about 10% w/w, based on the total weight of the composition.

In certain embodiments, the weight ratio of trihexyphenidyl or a pharmaceutically acceptable salt thereof to the organic acid is from about 1:1 to about 1:100, from about 1:1 to about 1:90, from about 11 to about 1:80, from about 1:1 to about 1:70, from about 1:1 to about 1:60, from about 1:1 to about 1:50, from about 1:1 to about 1:40, from about 1:1 to about 1:30, from about 1:1 to about 1:20, from about 1:1 to about 1:10, or any intermediate values therein, by weight. In certain embodiments, the weight ratio of trihexyphenidyl or a pharmaceutically acceptable salt thereof to the organic acid is about 1:50, about 1:47.7, about 1:45, about 1:42.5, about 1:40, about 1:37.5, about 1:35, about 1:32.5, about 1:30, about 1:29, about 1:28, about 1:27, about 1:26, about 1:25, about 1:24, about 1:23, about 1:22, about 1:21, about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, or any intermediate ratios thereof.

In certain embodiments, the drug layer (drug layer-1 and/or drug layer-2) comprises a nonionic water-soluble polymer. In certain embodiments, the nonionic water-soluble polymer in the drug layer is selected from the group consisting of hydroxypropyl cellulose, methyl cellulose, hydroxypropyl methylcellulose, hydroxyethyl cellulose, polyethylene glycol, polyvinyl alcohol, poloxamer, polyvinyl pyrrolidone-vinyl acetate copolymer (e.g., copovidone), and mixtures thereof. In certain embodiments, the amount of the nonionic water-soluble polymer ranges from about 5% to about 95%, from about 10% to about 90%, from about 20% to about 80%, from about 30% to about 70%, from about 40% to about 60%, or from about 45% to about 55% w/w, based on the total weight of the drug layer composition. In certain embodiments, the concentration of the nonionic water-soluble polymer ranges from about 10% to about 40%, e.g., about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, and about 39% w/w, or intermediate values thereof, based on the total weight of the drug layer composition. In certain embodiments, the concentration of the nonionic water-soluble polymer in drug layer-1 ranges from about 10% to about 40% w/w, based on the total weight of the drug layer-1 composition. In certain embodiments, the concentration of the nonionic water-soluble polymer in drug layer-1 is about 10%, about 20%, about 30%, about 31%, about 32%, about 33%, about 34%, about 35% w/w, about 36%, about 37%, about 38%, about 39%, about 40% w/w, or any intermediate values therein, based on the total weight of the drug layer-1 composition. In certain embodiments, the concentration of the nonionic water-soluble polymer in drug layer-2 ranges from about 10% to about 40% w/w, based on the total weight of the drug layer-2 composition. In certain embodiments, the concentration of the nonionic water-soluble polymer in drug layer-2 is about 10%, about 11%, about 12%, about 13%, about 14%, about 15% w/w, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40% w/w, or any intermediate values therein, based on the total weight of the drug layer-2 composition.

In certain embodiments, the drug layer(s) further includes additional excipients comprising anti-tacking agents, and/or plasticizers. In certain embodiments, anti-tacking agents include, but are not limited to, silicon dioxide (SYLOID® 244FP), fumed silica (CAB-O-SIL®), talc, kaolin, magnesium trisilicate, powdered starch, and/or tribasic calcium phosphate. In certain embodiments, the anti-tacking agent can be present in an amount of about 5% to about 100% w/w, based on the total weight of the nonionic water-soluble polymer present in the drug layer composition. In certain embodiments, the anti-tacking agent is present in an amount of about 10% w/w, about 15%, about 20%, about 25%, about 30%, about 35, about 40%, about 45%, about 50%, about 55%, about 60%, about 65%, about 70%, about 75%, about 80%, about 85%, or about 90% w/w, based on the total weight of the nonionic water-soluble polymer present in the drug layer composition.

In certain embodiments, the plasticizers include, but are not limited to, glycerin, triethyl citrate, triacetin, polyethylene glycol, propylene glycol, sorbitol sorbitan solution, and/or dibutyl sebacate. In certain embodiments, the plasticizer is triethyl citrate. In certain embodiments, the plasticizer is dibutyl sebacate. In certain embodiments, the plasticizer is present in an amount of about 0%, about 0.1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% w/w, or any intermediate values therein, based on the total weight of nonionic water-soluble polymer present in the drug layer composition. In certain embodiments, the total amount of the additional excipients is present in a range from about 0.1% to about 100%, from about 1% to about 50%, from about 2% to about 40%, from about 3% to about 35%, from about 4% to about 30%, from about 5% to about 25%, or from about 6% to about 20% w/w, based on the total weight of the nonionic water-soluble polymer present in the drug layer composition.

In certain embodiments, the drug layer (e.g., drug layer-1 and/or drug layer-2) comprise at least one organic acid to solubilize trihexyphenidyl. In certain embodiments, the immediate release drug layer, e.g., drug layer-2, comprises at least one organic acid. In certain embodiments, drug layer-1 (extended release drug layer) does not require any organic acid as the drug layer is in close proximity to the core comprising organic acid. In certain embodiments, drug layer-1 does not comprise an organic acid, and drug layer-2 comprises an organic acid. In certain embodiments, the organic acid comprises tartaric acid, citric acid, fumaric acid, succinic acid, malic acid, or any combinations thereof. In certain embodiments, the organic acid in drug layer-2 is different from the organic acid in the core. In certain embodiments, the organic acid in the core is tartaric acid and the organic acid in drug layer-2 is succinic acid. In certain embodiments, the organic acid in the core and drug layer-2 is tartaric acid and/or succinic acid.

6.2.4. Functional Coat/Extended Release Layer/Membrane

In certain embodiments, the drug-layered pellet is further coated with a functional coat comprising a water-insoluble polymer, a plasticizer, and a pore former. In certain embodiment, the functional coat can comprise at least one functional coat. In certain embodiments, there is a seal coat between the drug layer (drug layer-1) and the functional coat. In certain embodiments, the functional coat covers at least a portion of the drug layer (e.g., drug layer-1). In certain embodiments, the pellets comprising drug layer-1 (extended release drug layer) and drug layer-2 (immediate release drug layer) contain seal coat-1 between the core and dug layer-1; functional coat over drug layer-1; and seal coat-2 between functional coat and drug layer-2. In certain embodiments, coating solvents used for coating the functional coat comprise, but are not limited to, an organic solvent, water, and/or any mixtures thereof. In certain embodiments, the coating solvent is a mixture of an organic solvent and water. In certain embodiments, organic solvent: water weight ratio is between 60:40 and 98:2. In certain embodiments, the organic solvent:water weight ratio is about 60:40, about 70:30, about 75:25, 80:20, about 85:15, about 90:10, about 95:5, about 98:2, or any intermediate values therein. In certain embodiments, the coating solvents comprise organic solvents selected from the group consisting of methylene chloride, carbon tetrachloride, acetone, methanol, ethanol 200 proof, and/or any mixtures thereof. In certain embodiments, coating solvents comprise, but are not limited to, methylene chloride, carbon tetrachloride, acetone, methanol, ethanol 200 proof, water, and/or any mixtures thereof. In certain embodiments, the coating solvent is a mixture of ethanol 200 proof and water. In certain embodiments, ethanol:water weight ratio is between 60:40 and 98:2. In certain embodiments, the ethanol:water weight ratio is about 60:40, about 70:30, about 75:25, 80:20, about 85:15, about 90:10, about 95:5, about 98:2, or any intermediate values therein.

In certain embodiments, the functional coat has a coating weight gain of from about 5% to about 50% w/w, based on the total weight of the pellet without functional coat. In certain embodiments, the functional coat has a coating weight gain of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50% w/w, or any intermediate values therein, based on the total weight of the pellet without functional coat.

In certain embodiments, the functional coat comprises a water-insoluble polymer, a plasticizer, a pore former, and an anti-tacking agent. In certain embodiments, the functional coat includes a water-soluble polymer as a pore former. In certain embodiments, the water-soluble polymer is an enteric polymer. In certain embodiments, the enteric polymer used as a pore former comprises, but is not limited to, cellulose acetate phthalate, cellulose acetate succinate, methylcellulose phthalate, hydroxyethyl cellulose phthalate, polyvinyl acetate phthalate, polyvinyl butyrate acetate, vinyl acetate-maleic anhydride copolymer, hydroxypropyl methylcellulose phthalate, polyvinyl acetate phthalate, cellulose acetyl phthalate, methacrylic acid and methyl methacrylate (1:2) copolymer (EUDRAGIT® S 100), methacrylic acid and methyl methacrylate (1:1) copolymer (EUDRAGIT L®100), methacrylic acid and methyl methacrylate (1:2) copolymer solution (EUDRAGIT® S 12.5), methacrylic acid and methyl methacrylate (1:1) copolymer solution (EUDRAGIT® L 12.5), and combinations thereof. In certain embodiments, the pore former is a nonionic pH-independent water-soluble polymer comprising, but not limited to, methyl cellulose, hydroxypropyl cellulose, hydroxypropyl methylcellulose, hydroxyethyl cellulose, polyethylene glycol, polyvinyl alcohol, poloxamer, and mixtures thereof.

In certain embodiments, the water-insoluble polymer in the functional coat comprises, but is not limited to, ethyl cellulose (ETHOCEL™), cellulose acetate, cellulose diacetate, cellulose triacetate, cellulose propionate, a polyvinyl acetate dispersion (KOLLICOAT® SR), or mixtures thereof.

In certain embodiments, the water-insoluble polymer is present in an amount of from about 20% to about 99%, from about 40% to about 80%, from about 50% to about 70%, from about 55% to about 65%, w/w, or any intermediate value therein, based on the total weight of the functional coat. In certain embodiments, the water-insoluble polymer is present in an amount of about 20%, about 25%, about 30%, about 35%, about 40%, about 45%, about 50%, about 55%, about 56%, about 57%, about 58%, about 59%, about 60%, about 61%, about 62%, about 63%, about 64%, about 65%, about 66%, about 67%, about 68%, about 69%, about 70% w/w, or any intermediate values therein, based on the total weight of the functional coat. In certain embodiments, a pore former is present in an amount of from about 1% to about 50%, from about 10% to about 25%, from about 15% to about 20% w/w, or any intermediate values therein, based on the total weight of the functional coat. In certain embodiments, a pore former is present in an amount of about 1%, about 2%, about 3%, about 4%, 5%, about 6%, about 7%, about 8%, about 9%, about 10%, about 11%, about 12%, about 13%, about 14%, about 15% w/w, or any intermediate values therein, based on the total weight of the functional coat. In certain embodiments, the water-insoluble polymer and the pore former are present in a weight ratio of from about 50:50 to about 98:2. In certain embodiments, the water-insoluble polymer and the pore former are present in a weight ration of about 50:50, about 55:45, about 60:40, about 65:35, about 70:30, about 75:25, about 80:20, about 85:15, about 90:10, about 95:5, about 98:2, or any intermediate values therein.

In certain embodiments, the anti-tacking agents include, but are not limited to, silicon dioxide (SYLOID® 244FP), fumed silica (CAB-O-SIL®), talc, kaolin, talc, magnesium trisilicate, powdered starch, and/or tribasic calcium phosphate. In certain embodiments, the anti-tacking agent can be present in an amount of from about 5% to about 30% w/w, based on the combined weight of the water-insoluble polymer and the pore former. In certain embodiments, the anti-tacking agent is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30% w/w, or any intermediate values therein, based on the combined weight of the water-insoluble polymer and the pore former.

In certain embodiments, plasticizers include, but are not limited to, glycerin, polyethylene glycol monomethyl ether, triethyl citrate, triacetin, polyethylene glycol, propylene glycol, sorbitol sorbitan solution, dibutyl sebacate, or mixtures thereof. In certain embodiments, the plasticizer is triethyl citrate. In certain embodiments, the plasticizer is dibutyl sebacate. In certain embodiments, the plasticizer can be present in an amount of from about 0.1% to about 20% w/w, based on the combined weight of the water-insoluble polymer and the pore former. In certain embodiments, the plasticizer is present in an amount of about 0.1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% w/w, or any intermediate values therein, based on the combined weight of the water-insoluble polymer and the pore former.

In certain embodiments, the plasticizer acts as a pore former. In certain embodiments, the weight ratio of water-insoluble polymer and plasticizer determines the release rate of trihexyphenidyl hydrochloride. In certain embodiments, the enteric polymer functions as a pore former to release the trihexyphenidyl hydrochloride flux generated due to the presence of an acid microenvironment in the dosage form. In certain embodiments, the presence of (1) an acid microenvironment in the core; and (2) at least one water-insoluble polymer and at least one enteric polymer in the functional coat, maintains and controls the release rate of trihexyphenidyl hydrochloride throughout the GI tract, including the high pH regions of the GI tract with pH of greater than or equal to about 5.

6.2.5. Pellets

In certain embodiments, the present disclosure provides extended release oral trihexyphenidyl hydrochloride pellet compositions that maintain solubility of the drug in different pH environments of the GI tract, and maintain at least a minimum therapeutic plasma concentration of the drug for extended periods of time, without any initial spike or burst in release of the drug.

In certain embodiments, the pellets comprise a core comprising at least one organic acid and coated with a seal coat, a drug layer over the seal coat, and a functional coat/membrane over the drug-layered core. In certain embodiments, the pellets comprise a core coated with seal coat-1, drug layer-1 over seal coat-1, functional coat over drug layer-1, seal coat-2 over functional coat, drug layer-2 over seal coat-2, and an over coat over drug layer-2. In certain embodiments, the pellets comprise a core coated with seal coat-1, drug layer-1 over seal coat-1, and functional coat over drug layer-1.

In certain embodiments, the core comprises from about 10 mg to about 200 mg, from about 20 mg to about 100 mg, from about 30 mg to about 80 mg, from about 40 mg to about 60 mg, or about 50 mg of an organic acid. In certain embodiments, the core comprises tartaric acid in an amount of from about 45% w/w to about 80% w/w, from about 50% w/w to about 75% w/w, from about 55% w/w to about 70% w/w, or from about 60% w/w to about 65% w/w, based on the total weight of the composition.

In certain embodiments, the seal coat(s) (i.e., seal coat-1 and seal coat-2) and/or the over coat comprise from about 0.1 mg to about 10 mg, from about 0.2 mg to about 9.0 mg, from about 0.3 mg to about 8.0 mg, from about 0.4 mg to about 7.5 mg, from about 0.5 mg to about 7.0 mg, from about 1.0 mg to about 6.0 mg, from about 1.5 mg to about 5.0 mg, from about 2.0 mg to about 4.0 mg, from about 2.5 mg to about 3.5 mg, or about 3.0 mg of hypromellose (METHOCEL® E5 Prem LV). In certain embodiments, the seal coat(s) and/or over coat further comprise from about 0.01 mg to about 0.5 mg, from about 0.02 mg to about 0.4 mg, from about 0.03 mg to about 0.35 mg, from about 0.05 mg to about 0.25 mg, from about 0.06 mg to about 0.20 mg, from about 0.07 mg to about 0.15 mg, or from about 0.08 mg to about 0.10 mg of triethyl citrate. In certain embodiments, the seal coat(s) and/or over coat also comprise from about 0.05 mg to about 2.0 mg, from about 0.1 mg to about 1.5 mg, from about 0.15 mg to about 1.0 mg, from about 0.2 mg to about 0.9 mg, from about 0.25 mg to about 0.8 mg, from about 0.3 mg to about 0.7 mg, from about 0.35 mg to about 0.6 mg, or from about 0.4 mg to about 0.5 mg of talc. In certain embodiments, the seal coat(s) and/or the over coat comprise hypromellose (METHOCEL® E5 Prem LV) in an amount of from about 2.0% w/w to about 5.0% w/w, from about 2.25% w/w to about 4.5% w/w, from about 2.5% w/w to about 4.0% w/w, from about 2.75% w/w to about 3.5% w/w, or from about 3.0% w/w to about 3.25% w/w, based on the total weight of the composition. In certain embodiments, the seal coat(s) and/or over coat further comprise triethyl citrate in an amount of from about 0.05% w/w to about 0.30% w/w, from about 0.06% w/w to about 0.25% w/w, from about 0.07% w/w to about 0.24% w/w, from about 0.08% w/w to about 0.23% w/w, from about 0.09% w/w to about 0.22% w/w, from about 0.10% w/w to about 0.21% w/w, from about 0.11% w/w to about 0.20% w/w, from about 0.12% w/w to about 0.19% w/w, from about 0.13% w/w to about 0.18% w/w, from about 0.14% w/w to about 0.17% w/w, or from about 0.15% w/w to about 0.16% w/w, based on the total weight of the composition. In certain embodiments, the seal coat(s) and/or over coat also comprise talc in an amount of from about 0.5% w/w to about 1.25% w/w, from about 0.55% w/w to about 1.20% w/w, from about 0.60% w/w to about 1.15% w/w, from about 0.65% w/w to about 1.10% w/w, from about 0.70% w/w to about 1.05% w/w, from about 0.75% w/w to about 1.0% w/w, from about 0.80% w/w to about 0.95% w/w, or from about 0.85% w/w to about 0.90% w/w, based on the total weight of the dosage form.

In certain embodiments, drug layer-1 and drug layer-2 comprise trihexyphenidyl hydrochloride, hypromellose, triethyl citrate, and talc. In certain embodiments, drug layer-1 and/or drug layer-2 contain from about 0.5 mg to about 10 mg, from about 1.0 mg to about 9.0 mg, from about 1.5 mg to about 8.5 mg, from about 2.0 mg to about 8.0 mg, from about 2.5 mg to about 7.5 mg, from about 3.0 mg, to about 7.0 mg, from about 3.5 mg to about 6.5 mg, from about 4.0 mg to about 6.0 mg, from about 4.5 mg to about 5.5 mg, or about 5.0 mg of trihexyphenidyl hydrochloride. In certain embodiments, drug layer-1 and/or drug layer-2 comprise from about 0.01 mg to about 6.0 mg, from about 0.5 mg to about 5.0 mg, from about 1.0 mg to about 4.5 mg, from about 1.5 mg to about 4.0 mg, from about 2.0 mg to about 3.5 mg, or from about 2.5 mg to about 3.0 mg of hypromellose. In certain embodiments, drug layer-1 and/or drug layer-2 comprise from about 0.001 mg to about 0.3 mg, from about 0.01 mg to about 0.25 mg, from about 0.05 mg to about 0.2 mg, or from about 0.1 mg to about 0.15 mg of triethyl citrate. In certain embodiments, drug layer-1 and drug layer-2 comprise from about 0.05 mg to about 2.0 mg, from about 0.1 mg to about 1.5 mg, from about 0.2 mg to about 1.45 mg, from about 0.3 mg to about 1.40 mg, from about 0.4 mg to about 1.35 mg, from about 0.5 mg to about 1.30 mg, from about 0.6 mg to about 1.25 mg, from about 0.7 mg to about 1.20 mg, from about 0.8 mg to about 1.15 mg, from about 0.9 mg to about 1.10 mg, or about 1.0 mg of talc. In certain embodiments, total amount of trihexyphenidyl hydrochloride present in drug layer-1 and drug layer-2 is from about 0.5% w/w to about 10% w/w, from about 1.0% w/w to about 9% w/w, from about 1.5% w/w to about 8.0% w/w, from about 2.0% w/w to about 7.0% w/w, from about 2.5% w/w to about 6.5% w/w, from about 3.0% w/w to about 6.0% w/w, from about 3.5% w/w to about 5.5% w/w, from about 4.0% w/w to about 5.0% w/w, or from about 4.5% w/w to about 4.75% w/w, based on the total weight of the composition. In certain embodiments, total amount of hypromellose (METHOCEL® E5 Prem LV) present in drug layer-1 and drug layer-2 is from about 0.05% w/w to about 5.0% w/w, from about 0.10% w/w to about 4.5% w/w, from about 0.15% w/w to about 4.0% w/w, from about 1.0% w/w to about 3.5% w/w, from about 1.25% w/w to about 3.4% w/w, from about 1.5% w/w to about 3.3% w/w, from about 1.75% w/w to about 3.2% w/w, from about 2.0% w/w to about 3.1% w/w, from about 2.25% w/w to about 3.0% w/w, from about 2.5% w/w to about 2.9% w/w, or from about 2.75% w/w to about 2.8% w/w, based on the total weight of the dosage form. In certain embodiments, drug layer-1 and drug layer-2 comprise from about 0.01% w/w to about 0.3% w/w, from about 0.05% w/w to about 0.25% w/w, from about 0.10% w/w to about 0.2% w/w, from about 0.11% w/w to about 0.19% w/w, from about 0.12% w/w to about 0.18% w/w, from about 0.13% w/w to about 0.17% w/w, or from about 0.14% w/w to about 0.16% w/w of triethyl citrate, based on the total weight of the composition. In certain embodiments, drug layer-1 and drug layer-2 comprise from about 0.5% w/w to about 10% w/w, from about 1.0% w/w to about 9% w/w, from about 1.5% w/w to about 8.0% w/w, from about 2.0% w/w to about 7.0% w/w, from about 2.5% w/w to about 6.5% w/w, from about 3.0% w/w to about 6.0% w/w, from about 3.5% w/w to about 5.5% w/w, from about 4.0% w/w to about 5.0% w/w, or from about 4.5% w/w to about 4.75% w/w of talc.

In certain embodiments, the functional coat comprises ethyl cellulose (or Eudragit S 100), hypromellose phthalate (HP 55), triethyl citrate, and talc. In certain embodiments, the functional coat comprises from about 1.0 mg to about 20 mg, from about 2.0 mg to about 19 mg, from about 3.0 mg to about 18 mg, from about 4.0 mg to about 17 mg, from about 5.0 mg to about 16 mg, from about 6.0 mg to about 15 mg, from about 7.0 mg to about 14 mg, from about 8.0 mg to about 13 mg, from about 9.0 mg to about 12, or from about 10 mg to about 11 mg of ethyl cellulose. In certain embodiments, the functional coat comprises from about 0.1 mg to about 5.5 mg, from about 0.5 mg to about 5.0 mg, from about 1.0 mg to about 4.5 mg, from about 1.5 mg to about 4.0 mg, from about 2.0 mg to about 3.5 mg, or from about 2.5 mg to about 3.0 mg of hypromellose phthalate (HP 55). In certain embodiments, the functional coat comprises from about 0.1 mg to about 3.0 mg, from about 0.5 mg to about 2.5 mg, from about 1.0 mg to about 2.0 mg, or from about 1.25 mg to about 1.75 mg of triethyl citrate. In certain embodiments, the functional coat comprises from about 0.1 mg to about 5.5 mg, from about 0.5 mg to about 5.0 mg, from about 1.0 mg to about 4.5 mg, from about 1.5 mg to about 4.0 mg, from about 2.0 mg to about 3.5 mg, or from about 2.5 mg to about 3.0 mg of talc. In certain embodiments, the functional coat comprises ethyl cellulose (or Eudragit S 100), hypromellose phthalate (or Hypromellose/Methocel E5 Prem LV), triethyl citrate, and talc. In certain embodiments, the functional coat comprises from about 8.0% w/w to about 25% w/w, from about 9.0% w/w to about 24% w/w, from about 10% w/w to about 23% w/w, from about 11% w/w to about 22% w/w, from about 12% w/w to about 21% w/w, from about 13% w/w to about 20% w/w, from about 14% w/w to about 19% w/w, from about 15% w/w to about 18% w/w, or from about 16% w/w to about 17% w/w of ethyl cellulose (or Eudragit S 100), based on the total weight of the composition. In certain embodiments, the functional coat comprises from about 1% w/w to about 4% w/w, from about 1.5% w/w to about 3.5% w/w, from about 2% w/w to about 3% w/w, from about 2.25% w/w to about 2.75% w/w, or about 2.5% w/w of hypromellose phthalate (or Hypromellose/Methocel E5 Prem LV), based on the total weight of the dosage form. In certain embodiments, the functional coat comprises from about 0.5% w/w to about 3% w/w, from about 1% w/w to about 2.5% w/w, from about 1.1% w/w to about 2.25% w/w, from about 1.2% w/w to about 2% w/w, from about 1.3% w/w to about 1.9% w/w, from about 1.4% w/w to about 1.8% w/w, from about 1.5% w/w to about 1.7% w/w, or about 1.6% w/w of triethyl citrate, based on the total weight of the dosage form. In certain embodiments, the functional coat comprises from about 1.5% w/w to about 5% w/w, from about 2% w/w to about 4.5% w/w, from about 2.5% w/w to about 4% w/w, from about 2.75% w/w to about 3.5% w/w, from about 3% w/w to about 3.4% w/w, from about 3.1% w/w to about 3.3% w/w, or about 3.3% w/w of talc, based on the total weight of the dosage form.

In certain embodiments, the pellets of the present disclosure comprise a core, a seal coat, a drug layer, and a functional coat. In certain embodiments, the present disclosure provides for pellets that comprise a core comprising tartaric acid; a seal coat comprising hypromellose, triethyl citrate, and talc; a drug layer comprising trihexyphenidyl hydrochloride, hypromellose, triethyl citrate and talc; a functional coat comprising ethyl cellulose, Eudragit S 100 (anionic copolymers based on methacrylic acid and methyl methacrylate), hypromellose phthalate, hypromellose, triethyl citrate and talc.

In certain embodiments, the pellets of the present disclosure comprise from about 10.00 mg to about 250.00 mg of tartaric acid in the core; from about 1.50 mg to about 8.50 mg of hypromellose, from about 0.05 mg to about 0.45 mg of triethyl citrate and from about 0.40 mg to about 2.00 mg of talc in the seal coat; from about 3.00 mg to about 7.00 mg of trihexyphenidyl hydrochloride, from about 1.00 mg to about 5.00 mg of hypromellose, from about 0.10 mg to about 0.20 mg of triethyl citrate, and from about 0.30 mg to about 1.00 mg of talc in the drug layer; optionally from about 5.00 mg to about 25.00 mg of ethyl cellulose, optionally from about 5.00 mg to about 15.00 mg of Eudragit S 100 (anionic copolymers based on methacrylic acid and methyl methacrylate), optionally from about 1.00 mg to about 7.00 mg of hypromellose phthalate, optionally from about 1.50 mg to about 2.50 mg of hypromellose, from about 0.50 mg to about 3.00 mg of triethyl citrate, and from about 1.00 to about 5.50 mg of talc in the functional coat. In certain embodiments, the pellets of the present disclosure comprise from about 50% w/w to about 75% w/w of tartaric acid in the core; from about 2.0% w/w to about 3.0% w/w of hypromellose, from about 0.10% w/w to about 0.20% w/w of triethyl citrate and from about 0.50% w/w to about 1.00% w/w of talc in the seal coat; from about 1.90% w/w to about 7.00% w/w of trihexyphenidyl hydrochloride, from about 1.00% w/w to about 5.00% w/w of hypromellose, from about 0.10% w/w to about 0.25% w/w of triethyl citrate, and from about 0.50% w/w to about 1.00% w/w of talc in the drug layer; optionally from about 8.00% w/w to about 15.00% w/w of ethyl cellulose, optionally from about 10.00% w/w to about 15.00% w/w of Eudragit S 100 (anionic copolymers based on methacrylic acid and methyl methacrylate), optionally from about 2.0% w/w to about 3.5% w/w of hypromellose phthalate, optionally from about 2.00% w/w to about 3.00% w/w of hypromellose, from about 1.00% w/w to about 2.00% w/w of triethyl citrate, and from about 2.00% w/w to about 4.00% w/w of talc in the functional coat, based on the total weight of the composition.

In a particular embodiment, a pellet of the present disclosure comprises about 70.98% w/w of tartaric acid in the core; about 2.73% w/w of hypromellose, about 0.14% w/w of triethyl citrate, and about 0.68% w/w talc in the seal coat; about 7.10% w/w of trihexyphenidyl hydrochloride, about 4.26% w/w of Hypromellose, about 0.21% w/w of triethyl citrate, and about 0.85% w/w of talc in the drug layer; about 8.04% w/w of ethyl cellulose, about 2.00% w/w of hypromellose phthalate, about 1.01% w/w of triethyl citrate, and about 2.00% w/w of talc in the functional coat, all amounts based on the total weight of the composition.

In another particular embodiment, a pellet of the present disclosure comprises about 79.50% w/w of tartaric acid in the core; about 3.06% w/w of hypromellose, about 0.15% w/w of triethyl citrate, and about 0.76% w/w talc in the seal coat; about 1.99% w/w of trihexyphenidyl hydrochloride, about 1.19% w/w of hypromellose, about 0.06% w/w of triethyl citrate, and about 0.24% w/w of talc in the drug layer; about 8.03% w/w of ethyl cellulose, about 2.01% w/w of hypromellose phthalate, about 1.00% w/w of triethyl citrate, and about 2.01% w/w of talc in the functional coat, all amounts based on the total weight of the composition.

In another particular embodiment, a pellet of the present disclosure comprises about 65.30% w/w of tartaric acid in the core; about 2.51% w/w of hypromellose, about 0.13% w/w of triethyl citrate, and about 0.63% w/w talc in the seal coat; about 6.53% w/w of trihexyphenidyl hydrochloride, about 3.92% w/w of hypromellose, about 0.20% w/w of triethyl citrate, and about 0.78% w/w of talc in the drug layer; about 13.07% w/w of ethyl cellulose, about 2.31% w/w of hypromellose phthalate, about 1.54% w/w of triethyl citrate, and about 3.08% w/w of talc in the functional coat, all amounts based on the total weight of the composition.

In another particular embodiment, a pellet of the present disclosure comprises about 60.47% w/w of tartaric acid in the core; about 2.51% w/w of hypromellose, about 0.13% w/w of triethyl citrate, and about 0.63% w/w talc in the seal coat; about 6.53% w/w of trihexyphenidyl hydrochloride, about 3.92% w/w of hypromellose, about 0.20% w/w of triethyl citrate, and about 0.78% w/w of talc in the drug layer; about 13.07% w/w of ethyl cellulose, about 2.31% w/w of hypromellose, about 1.54% w/w of triethyl citrate, and about 3.08% w/w of talc in the functional coat, all amounts based on the total weight of the composition.

In another particular embodiment, a pellet of the present disclosure comprises about 60.47% w/w of tartaric acid in the core; about 2.32% w/w of hypromellose, about 0.12% w/w of triethyl citrate, and about 0.58% w/w talc in the seal coat; about 6.05% w/w of trihexyphenidyl hydrochloride, about 3.63% w/w of hypromellose, about 0.18% w/w of triethyl citrate, and about 0.73% w/w of talc in the drug layer; about 16.95% w/w of ethyl cellulose, about 2.99% w/w of hypromellose phthalate, about 2.00% w/w of triethyl citrate, and about 3.99% w/w of talc in the functional coat, all amounts based on the total weight of the composition.

In another particular embodiment, a pellet of the present disclosure comprises about 65.31% w/w of tartaric acid in the core; about 2.51% w/w of hypromellose, about 0.13% w/w of triethyl citrate, and about 0.63% w/w talc in the seal coat; about 6.53% w/w of trihexyphenidyl hydrochloride, about 3.92% w/w of hypromellose, about 0.20% w/w of triethyl citrate, and about 0.78% w/w of talc in the drug layer; about 12.3% w/w of Eudragit S 100 (anionic copolymers based on methacrylic acid and methyl methacrylate), about 3.08% w/w of hypromellose phthalate, about 1.54% w/w of triethyl citrate, and about 3.07% w/w of talc in the functional coat, all amounts based on the total weight of the composition.

In another particular embodiment, a pellet of the present disclosure comprises about 68.03% w/w of tartaric acid in the core; about 2.61% w/w of hypromellose, about 0.14% w/w of triethyl citrate, and about 0.65% w/w talc in the seal coat; about 6.80% w/w of trihexyphenidyl hydrochloride, about 4.08% w/w of hypromellose, about 0.20% w/w of triethyl citrate, and about 0.82% w/w of talc in the drug layer; about 10.20% w/w of ethyl cellulose, about 2.56% w/w of hypromellose phthalate, about 1.29% w/w of triethyl citrate, and about 2.56% w/w of talc in the functional coat, all amounts based on the total weight of the composition.

In another particular embodiment, a pellet of the present disclosure comprises about 65.36% w/w of tartaric acid in the core; about 2.51% w/w of hypromellose, about 0.13% w/w of triethyl citrate, and about 0.63% w/w talc in the seal coat; about 6.54% w/w of trihexyphenidyl hydrochloride, about 3.92% w/w of hypromellose, about 0.20% w/w of triethyl citrate, and about 0.78% w/w of talc in the drug layer; about 13.0% w/w of ethyl cellulose, about 2.30% w/w of hypromellose phthalate, about 1.53% w/w of triethyl citrate, and about 3.07% w/w of talc in the functional coat, all amounts based on the total weight of the composition.

In certain embodiments, the pellets of the present disclosure comprise a core, a seal coat-1, a drug layer-1, a functional coat, a seal coat-2, a drug layer-2, and an over coat. In certain embodiments, the pellets of the present disclosure comprise from about 25.00% w/w to about 75.00% w/w or tartaric acid in the core; from about 1.50% w/w to about 3.00% w/w of hypromellose, from about 0.05% w/w to about 0.20% w/w of triethyl citrate, and from about 0.40% w/w to about 0.75% w/w of talc in the seal coat-1; from about 4.00% w/w to about 6.50% w/w of trihexyphenidyl hydrochloride, from about 2.50% w/w to about 4.00% w/w of hypromellose, from about 0.10% w/w to about 0.25% w/w of triethyl citrate, and from about 0.50% w/w to about 1.00% w/w of talc in the drug layer-1; from about 5.00% w/w to about 20.00% w/w of ethyl cellulose, from about 1.00 to about 3.50% w/w of hypromellose phthalate, from about 0.50% w/w to about 2.50% w/w of triethyl citrate, and from about 1.25% w/w to about 4.75% w/w of talc in the functional coat; optionally from about 2.75% w/w to about 4.50% w/w of hypromellose, optionally from about 0.70% w/w to about 1.10% w/w of talc, and optionally from about 0.05% w/w to about 0.25% w/w of triethyl citrate in the seal coat-2; optionally from about 0.50% w/w to about 1.50% w/w of trihexyphenidyl hydrochloride, optionally from about 0.50% w/w to about 1.00% w/w of succinic acid, optionally from about 1.00% w/w to about 2.50% w/w of tartaric acid, optionally from about 0.40% w/w to about 0.50% w/w of hypromellose, optionally from about 1.00% w/w to about 2.00% w/w of Copovidone, optionally from about 0.01% w/w to about 0.05% w/w talc, and optionally about 0.01% w/w of colloidal silicon dioxide in the drug layer-2; optionally from about 3.00% w/w to about 5.00% w/w of hypromellose, optionally from about 0.05% w/w to about 0.30% w/w of triethyl citrate, and from about 0.050% w/w to about 1.50% w/w of talc in the over coat, all amounts based on the total weight of the composition.

In a particular embodiment, a pellet of the present disclosure comprises about 58.65% w/w of tartaric acid in the core; about 2.25% w/w of hypromellose, about 0.12% w/w of triethyl citrate, about 0.56% w/w of talc in the seal coat-1; about 4.99% w/w of trihexyphenidyl hydrochloride, about 2.99% w/w of hypromellose, about 0.18% w/w of triethyl citrate, and about 0.65% w/w of talc in the drug layer-1; about 11.50% w/w of ethyl cellulose, about 2.05% w/w of hypromellose phthalate, about 1.35% w/w of triethyl citrate, and about 2.70% w/w of talc in the functional coat; about 3.45% w/w of hypromellose, about 0.88% w/w of talc, and about 0.09% w/w of triethyl citrate in the seal coat-2; about 0.88% w/w of trihexyphenidyl hydrochloride, about 0.88% w/w of succinic acid, about 0.53% w/w of hypromellose, about 0.02% w/w of triethyl citrate, about 0.53% w/w of talc, and about 0.01% w/w of colloidal silicon dioxide in the drug layer-2; about 3.73% w/w of hypromellose, about 0.08% w/w of triethyl citrate, and 0.94% w/w of talc in the over coat, all amounts based on the total weight of the composition.

In another particular embodiment, a pellet of the present disclosure comprises about 71.04% w/w of tartaric acid in the core; about 2.73% w/w of hypromellose, about 0.14% w/w of triethyl citrate, about 0.68% w/w of talc in the seal coat-1; about 7.10% w/w of trihexyphenidyl hydrochloride, about 4.26% w/w of hypromellose, about 0.21% w/w of triethyl citrate, and about 0.85% w/w of talc in the drug layer-1; about 8.50% w/w of ethyl cellulose, about 1.49% w/w of hypromellose phthalate, about 0.99% w/w of triethyl citrate, and about 1.99% w/w of talc in the functional coat, all amounts based on the total weight of the composition.

In another particular embodiment, a pellet of the present disclosure comprises about 63.79% w/w of tartaric acid in the core; about 2.45% w/w of hypromellose, about 0.13% w/w of triethyl citrate, about 0.61% w/w of talc in the seal coat-1; about 6.38% w/w of trihexyphenidyl hydrochloride, about 3.83% w/w of hypromellose, about 0.19% w/w of triethyl citrate, and about 0.77% w/w of talc in the drug layer-1; about 14.30% w/w of ethyl cellulose, about 2.51% w/w of hypromellose phthalate, about 1.68% w/w of triethyl citrate, and about 3.36% w/w of talc in the functional coat, all amounts based on the total weight of the composition.

In another particular embodiment, a pellet of the present disclosure comprises about 57.4% w/w of tartaric acid in the core; about 2.21% w/w of hypromellose, about 0.11% w/w of triethyl citrate, about 0.55% w/w of talc in the seal coat-1; about 5.75% w/w of trihexyphenidyl hydrochloride, about 3.45% w/w of hypromellose, about 0.17% w/w of triethyl citrate, and about 0.69% w/w of talc in the drug layer-1; about 19.34% w/w of ethyl cellulose, about 3.40% w/w of hypromellose phthalate, about 2.28% w/w of triethyl citrate, and about 4.55% w/w of talc in the functional coat, all amounts based on the total weight of the composition.

In another particular embodiment, a pellet of the present disclosure comprises about 54.79% w/w of tartaric acid in the core; about 2.10% w/w of hypromellose, about 0.11% w/w of triethyl citrate, about 0.53% w/w of talc in the seal coat-1; about 5.48% w/w of trihexyphenidyl hydrochloride, about 3.29% w/w of hypromellose, about 0.16% w/w of triethyl citrate, and about 0.66% w/w of talc in the drug layer-1; about 21.50% w/w of ethyl cellulose, about 3.78% w/w of hypromellose phthalate, about 2.53% w/w of triethyl citrate, and about 5.06% w/w of talc in the functional coat, all amounts based on the total weight of the composition.

In another particular embodiment, a pellet of the present disclosure comprises about 57.30% w/w of tartaric acid in the core; about 2.20% w/w of hypromellose, about 0.11% w/w of triethyl citrate, about 0.55% w/w of talc in the seal coat-1; about 4.87% w/w of trihexyphenidyl hydrochloride, about 2.92% w/w of hypromellose, about 0.17% w/w of triethyl citrate, and about 0.63% w/w of talc in the drug layer-1; about 11.20% w/w of ethyl cellulose, about 2.01% w/w of hypromellose phthalate, about 1.32% w/w of triethyl citrate, and about 2.64% w/w of talc in the functional coat; about 3.30% w/w of hypromellose, about 0.83% w/w of talc, and about 0.17% w/w of triethyl citrate in the seal coat-2; about 0.86% w/w of trihexyphenidyl hydrochloride, about 1.72% w/w of tartaric acid, about 1.24% w/w of Copovidone, and about 1.15% w/w of talc, in the drug layer-2; about 3.61% w/w of hypromellose, about 0.18% w/w of triethyl citrate, and about 0.91% w/w of talc in the over coat, all amounts based on the total weight of the composition.

In another particular embodiment, a pellet of the present disclosure comprises about 52.85% w/w of tartaric acid in the core; about 2.43% w/w of hypromellose, about 0.13% w/w of triethyl citrate, about 0.60% w/w of talc in the seal coat-1; about 5.39% w/w of trihexyphenidyl hydrochloride, about 3.23% w/w of hypromellose, about 0.19% w/w of triethyl citrate, and about 0.70% w/w of talc in the drug layer-1; about 12.43% w/w of ethyl cellulose, about 2.22% w/w of hypromellose phthalate, about 1.46% w/w of triethyl citrate, and about 2.92% w/w of talc in the functional coat; about 3.65% w/w of hypromellose, about 0.91% w/w of talc, and about 0.19% w/w of triethyl citrate in the seal coat-2; about 0.95% w/w of trihexyphenidyl hydrochloride, about 1.90% w/w of tartaric acid, about 1.37% w/w of Copovidone, and about 1.27% w/w of talc, in the drug layer-2; about 4.00% w/w of hypromellose, about 0.20% w/w of triethyl citrate, and about 1.00% w/w of talc in the over coat, all amounts based on the total weight of the composition.

In another particular embodiment, a pellet of the present disclosure comprises about 47.29% w/w of tartaric acid in the core; about 2.72% w/w of hypromellose, about 0.14% w/w of triethyl citrate, about 0.68% w/w of talc in the seal coat-1; about 6.03% w/w of trihexyphenidyl hydrochloride, about 3.59% w/w of hypromellose, about 0.21% w/w of triethyl citrate, and about 0.78% w/w of talc in the drug layer-1; about 13.90% w/w of ethyl cellulose, about 2.46% w/w of hypromellose phthalate, about 1.63% w/w of triethyl citrate, and about 3.26% w/w of talc in the functional coat; about 4.09% w/w of hypromellose, about 1.02% w/w of talc, and about 0.21% w/w of triethyl citrate in the seal coat-2; about 1.06% w/w of trihexyphenidyl hydrochloride, about 2.13% w/w of tartaric acid, about 1.53% w/w of Copovidone, and about 1.42% w/w of talc, in the drug layer-2; about 4.46% w/w of hypromellose, about 0.23% w/w of triethyl citrate, and about 1.14% w/w of talc in the over coat, all amounts based on the total weight of the composition.

In another particular embodiment, a pellet of the present disclosure comprises about 58.53% w/w of tartaric acid in the core; about 2.25% w/w of hypromellose, about 0.12% w/w of triethyl citrate, about 0.56% w/w of talc in the seal coat-1; about 5.41% w/w of trihexyphenidyl hydrochloride, about 3.25% w/w of hypromellose, about 0.19% w/w of triethyl citrate, and about 0.70% w/w of talc in the drug layer-1; about 11.60% w/w of ethyl cellulose, about 2.07% w/w of hypromellose phthalate, about 1.36% w/w of triethyl citrate, and about 2.72% w/w of talc in the functional coat; about 3.46% w/w of hypromellose, about 0.88% w/w of talc, and about 0.09% w/w of triethyl citrate in the seal coat-2; about 0.44% w/w of trihexyphenidyl hydrochloride, about 0.44% w/w of succinic acid, about 0.14% w/w of hypromellose, about 0.02% w/w of triethyl citrate, about 0.53% w/w of talc, and about 0.01% w/w of colloidal silicon dioxide in the drug layer-2; about 3.73% w/w of hypromellose, about 0.08% w/w of triethyl citrate, and about 0.94% w/w of talc in the over coat, all amounts based on the total weight of the composition.

In another particular embodiment, a pellet of the present disclosure comprises about 10.00 mg of tartaric acid in the core; about 0.384 mg of hypromellose, about 0.02 mg of triethyl citrate, about 0.096 mg of talc in the seal coat-1; about 0.925 mg of trihexyphenidyl hydrochloride, about 0.555 mg of hypromellose, about 0.333 mg of triethyl citrate, and about 0.120 mg of talc in the drug layer-1; about 1.982 mg of ethyl cellulose, about 0.354 mg of hypromellose phthalate, about 0.233 mg of triethyl citrate, and about 0.465 mg of talc in the functional coat; about 0.591 mg of hypromellose, about 0.151 mg of talc, and about 0.016 mg of triethyl citrate in the seal coat-2; about 0.075 mg of trihexyphenidyl hydrochloride, about 0.075 mg of succinic acid, about 0.023 mg of hypromellose, about 0.004 mg of triethyl citrate, about 0.90 mg of talc, and about 0.002 mg of colloidal silicon dioxide in the drug layer-2; about 0.636 mg of hypromellose, about 0.014 mg of triethyl citrate, and about 0.160 mg of talc in the over coat.

In another particular embodiment, a pellet of the present disclosure comprises about 20.00 mg of tartaric acid in the core; about 0.77 mg of hypromellose, about 0.04 mg of triethyl citrate, about 0.192 mg of talc in the seal coat-1; about 1.850 mg of trihexyphenidyl hydrochloride, about 1.110 mg of hypromellose, about 0.065 mg of triethyl citrate, and about 0.239 mg of talc in the drug layer-1; about 3.963 mg of ethyl cellulose, about 0.708 mg of hypromellose phthalate, about 0.465 mg of triethyl citrate, and about 0.930 mg of talc in the functional coat; about 1.183 mg of hypromellose, about 0.302 mg of talc, and about 0.032 mg of triethyl citrate in the seal coat-2; about 0.15 mg of trihexyphenidyl hydrochloride, about 0.15 mg of succinic acid, about 0.05 mg of hypromellose, about 0.01 mg of triethyl citrate, and about 0.18 mg of talc in the drug layer-2; about 1.27 mg of hypromellose, about 0.03 mg of triethyl citrate, and about 0.32 mg of talc in the over coat.

In another particular embodiment, a pellet of the present disclosure comprises about 60.00 mg of tartaric acid in the core; about 2.304 mg of hypromellose, about 0.120 mg of triethyl citrate, about 0.576 mg of talc in the seal coat-1; about 5.550 mg of trihexyphenidyl hydrochloride, about 3.330 mg of hypromellose, about 0.196 mg of triethyl citrate, and about 0.718 mg of talc in the drug layer-1; about 11.890 mg of ethyl cellulose, about 2.123 mg of hypromellose phthalate, about 1.395 mg of triethyl citrate, and about 2.790 mg of talc in the functional coat; about 3.548 mg of hypromellose, about 0.905 mg of talc, and about 0.097 mg of triethyl citrate in the seal coat-2; about 0.45 mg of trihexyphenidyl hydrochloride, about 0.45 mg of succinic acid, about 0.14 mg of hypromellose, about 0.02 mg of triethyl citrate, about 0.54 mg of talc, and about 0.01 mg of colloidal silicon dioxide in the drug layer-2; about 3.82 mg of hypromellose, about 0.08 mg of triethyl citrate, and about 0.96 mg of talc in the over coat.

In another particular embodiment, a pellet of the present disclosure comprises about 80.00 mg of tartaric acid in the core; about 3.072 mg of hypromellose, about 0.16 mg of triethyl citrate, about 0.768 mg of talc in the seal coat-1; about 7.400 mg of trihexyphenidyl hydrochloride, about 4.440 mg of hypromellose, about 0.261 mg of triethyl citrate, and about 0.958 mg of talc in the drug layer-1; about 15.853 mg of ethyl cellulose, about 2.831 mg of hypromellose phthalate, about 1.860 mg of triethyl citrate, and about 3.721 mg of talc in the functional coat; about 4.731 mg of hypromellose, about 1.207 mg of talc, and about 0.129 mg of triethyl citrate in the seal coat-2; about 0.60 mg of trihexyphenidyl hydrochloride, about 0.60 mg of succinic acid, about 0.18 mg of hypromellose, about 0.03 mg of triethyl citrate, about 0.72 mg of talc, and about 0.02 mg of colloidal silicon dioxide in the drug layer-2; about 5.09 mg of hypromellose, about 0.11 mg of triethyl citrate, and about 1.28 mg of talc in the over coat.

In another particular embodiment, a pellet of the present disclosure comprises about 100.00 mg of tartaric acid in the core; about 3.84 mg of hypromellose, about 0.20 mg of triethyl citrate, about 0.96 mg of talc in the seal coat-1; about 9.250 mg of trihexyphenidyl hydrochloride, about 5.550 mg of hypromellose, about 0.326 mg of triethyl citrate, and about 1.197 mg of talc in the drug layer-1; about 19.816 mg of ethyl cellulose, about 3.539 mg of hypromellose phthalate, about 2.325 mg of triethyl citrate, and about 4.651 mg of talc in the functional coat; about 5.913 mg of hypromellose, about 1.508 mg of talc, and about 0.161 mg of triethyl citrate in the seal coat-2; about 0.75 mg of trihexyphenidyl hydrochloride, about 0.75 mg of succinic acid, about 0.23 mg of hypromellose, about 0.04 mg of triethyl citrate, about 0.90 mg of talc, and about 0.02 mg of colloidal silicon dioxide in the drug layer-2; about 6.36 mg of hypromellose, about 0.14 mg of triethyl citrate, and about 1.60 mg of talc in the over coat.

6.3. Compositions

In certain embodiments, the present disclosure provides compositions comprising capsules containing a final blend comprising extended release trihexyphenidyl hydrochloride pellets, colloidal silicon dioxide, and talc.

In certain embodiments, the final blend comprises from about 30 mg to about 200 mg, from about 35 mg to about 175 mg, from about 40 mg to about 150 mg, from about 45 mg to about 125 mg, or from about 50 mg to about 100 mg of extended release THP pellets. In certain embodiments, the final blend comprises from about 0.01 mg to about 0.5 mg, from about 0.05 mg to about 0.4 mg, from about 0.1 mg to about 0.3 mg, or from about 0.2 mg to about 0.25 mg of colloidal silicon dioxide. In certain embodiments, the final blend comprises from about 0.05 mg to about 0.6 mg, from about 0.1 mg to about 0.5 mg, from about 0.15 mg to about 0.4 mg, from about 0.2 mg to about 0.3 mg, or about 0.25 mg of talc.

In certain embodiments, the final blend comprises from about 30 mg to about 200 mg, from about 35 mg to about 175 mg, from about 40 mg to about 150 mg, from about 45 mg to about 125 mg, or from about 50 mg to about 100 mg of extended release THP pellets; from about 0.01 mg to about 0.5 mg, from about 0.05 mg to about 0.4 mg, from about 0.1 mg to about 0.3 mg, or from about 0.2 mg to about 0.25 mg of colloidal silicon dioxide; and from about 0.05 mg to about 0.6 mg, from about 0.1 mg to about 0.5 mg, from about 0.15 mg to about 0.4 mg, from about 0.2 mg to about 0.3 mg, or about 0.25 mg of talc. In certain embodiments, the final blend comprises from about 97% w/w to about 99.7%/w/w of extended release THP pellets; from about 0.2% w/w to about 0.3% w/w of colloidal silicon dioxide; and from about 0.2% w/w to about 0.3% w/w of talc.

In a particular embodiment, the final blend of the present disclosure comprises about 102.01 mg of THP pellets, about 0.25 mg of colloidal silicon dioxide, and about 0.25 mg of talc. In another particular embodiment, the final blend of the present disclosure comprises about 17.002 mg of THP pellets, about 0.042 mg of colloidal silicon dioxide, and about 0.042 mg of talc. In another particular embodiment, the final blend of the present disclosure comprises about 34.004 mg of THP pellets, about 0.08 mg of colloidal silicon dioxide, and about 0.08 mg of talc. In another particular embodiment, the final blend of the present disclosure comprises about 102.013 mg of THP pellets, about 0.25 mg of colloidal silicon dioxide, and about 0.25 mg of talc. In another particular embodiment, the final blend of the present disclosure comprises about 136.018 mg of THP pellets, about 0.33 mg of colloidal silicon dioxide, and about 0.33 mg of talc. In another particular embodiment, the final blend of the present disclosure comprises about 170.022 mg of THP pellets, about 0.42 mg of colloidal silicon dioxide, and about 0.42 mg of talc. In another particular embodiment, the final blend of the present disclosure comprises about 15.30 mg of THP pellets, about 0.10 mg of colloidal silicon dioxide, and about 0.10 mg of talc. In another particular embodiment, the final blend of the present disclosure comprises about 30.60 mg of THP pellets, about 0.20 mg of colloidal silicon dioxide, and about 0.20 mg of talc. In another particular embodiment, the final blend of the present disclosure comprises about 91.80 mg of THP pellets, about 0.60 mg of colloidal silicon dioxide, and about 0.60 mg of talc. In another particular embodiment, the final blend of the present disclosure comprises about 122.40 mg of THP pellets, about 0.80 mg of colloidal silicon dioxide, and about 080 mg of talc. In another particular embodiment, the final blend of the present disclosure comprises about 153.0 mg of THP pellets, about 1.0 mg of colloidal silicon dioxide, and about 1.0 mg of talc.

6.4. Methods of Making

In certain embodiments, the present disclosure provides extended release trihexyphenidyl compositions providing and maintaining therapeutically effective stable plasma concentrations of THP or a pharmaceutically acceptable salt thereof, without any initial burst release/dose dumping. In certain embodiments, the compositions of the disclosure provide extended release of THP or a pharmaceutically acceptable salt thereof for at least about 10 hours, e.g., from about 16 hours to about 24 hours, under physiologically relevant conditions.

The extended release trihexyphenidyl compositions of the disclosure include extended release pellets suitable for dosing in capsules, sachets, administration through feeding tubes, and as sprinkles on food, and liquids. In certain embodiments, the extended release pellets comprise a core comprising an organic acid; a seal coat comprising a water-soluble, nonionic polymer over the core comprising organic acid; a drug layer comprising trihexyphenidyl hydrochloride over the seal coat; and a functional coat/rate controlling membrane, comprising a water soluble polymer or an enteric polymer, a water-insoluble polymer, and a plasticizer, over the drug layer. In certain embodiments, the presence of seal coat is optional. In certain embodiments, the core is spherical or irregular in shape. In certain embodiments, the core is a pellet, bead/seed, or a granule comprising at least one organic acid. In certain embodiments, the core is a pellet, bead/seed, or a granule coated with at least one coating comprising at least one organic acid. In certain embodiments, the core is an organic acid or a mixture of organic acids. In a specific embodiment, organic acid granules are used as the core. In certain embodiments, the core is an acid coated core comprising a nonpareil seed coated with at least one coating comprising at least one organic acid, e.g., a cellet/sugar sphere coated with an organic acid. In certain embodiments, the core is a microcrystalline cellulose sphere, or a sugar sphere coated with at least one coating comprising at least one organic acid. In certain embodiments, the organic acid coat over the nonpareil seed contains trihexyphenidyl or a pharmaceutically acceptable salt thereof. In certain embodiments, the organic acid core is coated with a coat containing trihexyphenidyl or a pharmaceutically acceptable salt thereof, and at least one additional organic acid. In certain embodiments, the additional organic acid in the coating can be same as the organic acid present in the core. In certain embodiments, the additional organic acid in the coating can be different from the organic acid present in the core.

In certain embodiments, the extended release pellets are made by coating the core comprising an organic acid with a seal coat (seal coat-1) comprising a nonionic water-soluble polymer, coating the seal-coated core with a drug layer comprising trihexyphenidyl hydrochloride and a nonionic water-soluble polymer, and coating the drug-layered core with a functional coat/membrane comprising a water-insoluble polymer, e.g., ethyl cellulose and an enteric polymer, e.g., HP 55 (hypromellose phthalate). In certain embodiments, the functional coat is further coated with an immediate release drug layer (drug layer-2) containing trihexyphenidyl hydrochloride for immediate release. In certain embodiments, there is a seal coat (seal coat-2) between the functional coat and drug layer-2. In certain embodiments, the presence of the seal coat-2 and/or drug layer-2 is optional. In certain embodiments, the drug layer-2 contains trihexyphenidyl hydrochloride and an organic acid. In certain embodiments, the organic acid in the core and the drug layer-2 are different.

6.5. Methods of Use

In certain embodiments, the disclosure provides methods for treating symptoms of Parkinson's disease, cerebral palsy, dystonia, sialorrhea, dyskinesia, dystonia associated with cerebral palsy (dyskinetic cerebral palsy), tremors, strokes, movement disorders, and any other disease or disorder for which trihexyphenidyl is an appropriate treatment. In certain embodiments, the disclosure provides methods for treating parkinsonism, including primary or idiopathic Parkinson's disease, secondary symptomatic parkinsonism (postencephalitic, arteriosclerotic, infection-induced, tumor-induced, trauma-induced, and drug-induced), and involuntary movements due to side effects of certain psychiatric drugs. The methods comprise administering to a patient in need thereof, an extended release trihexyphenidyl composition of the disclosure suitable for once- or twice-daily administration. In certain embodiments, the disclosure provides methods for using extended release trihexyphenidyl compositions of the disclosure for use as an adjunct in the treatment of all forms of parkinsonism and for the control of extrapyramidal disorders caused by central nervous system drugs such as dibenzoxazepines, phenothiazines, thioxanthenes, and butyrophenones. The methods comprise administering to a patient in need thereof, an extended release trihexyphenidyl composition of the disclosure suitable for once- or twice-daily administration.

In certain embodiments, the disclosure provides methods for improving patient compliance by reducing symptoms, generally associated with high peak serum concentrations ($C_{max}$) and high peak-to-trough fluctuations provided by immediate release trihexyphenidyl products. In certain embodiments, improving patient compliance comprises reducing symptoms of drowsiness, dizziness or blurred vision, dry mouth, stomach upset, vomiting, diarrhea, constipation, and difficulty in urinating and or/retention, confusion, agitation, and hallucinations, particularly during the night. The methods comprise administering the extended release trihexyphenidyl compositions of the disclosure, wherein the composition provides a reduced $C_{max}$, and reduced dose related peak-to-trough fluctuations, e.g., $C_{min}$:$C_{max}$ ratio of greater than or equal to 0.4 and FI of less than or equal to las compared to marketed IR trihexyphenidyl tablets. FIG. 8 compares pharmacokinetic data for Artane IR (5 mg BID), and Artane ER (10 mg QD) (see, Cheung et al. (1988), supra) with a 5 mg extended release Pellet 9 (Test T) (normalized to 10 mg). FIG. 8 demonstrates that Pellet 9 exhibits reduced variability (e.g., $C_{min}$:$C_{max}$ ratio of greater than or equal to 0.4) in the plasma concentration of THP over an extended time period compared to Artane ER (10 mg) and Artane IR (5 mg BID).

In certain embodiments, the disclosure provides methods for reducing side effects associated with currently marketed immediate release trihexyphenidyl compositions. In certain embodiments, the methods comprise administering extended release trihexyphenidyl compositions of the disclosure that (1) reduce initial burst release/dose dumping and (2) maintain therapeutic plasma concentrations of the drug for extended periods of time. In certain embodiments, the therapeutic plasma concentrations depend on the severity of the patient's condition, and on the strength of the THP composition administered to the patient. In certain embodiments, the compositions of the disclosure contain from about 1% to about 20% w/w, based on the total weight of the composition, of trihexyphenidyl or a pharmaceutically acceptable salt thereof. In certain embodiments, the compositions of the disclosure contain from about 1 mg to about 20 mg of trihexyphenidyl or a pharmaceutically acceptable salt thereof.

In certain embodiments, the disclosure provides methods for improving patient compliance by administering extended release trihexyphenidyl compositions of the disclosure, wherein the extended release compositions will allow for reduced frequency of administration of the composition, administration as sprinkle on solid food or liquids, administration via feeding tubes, and reduce side effects associated with high $C_{max}$ levels and low $C_{min}$:$C_{max}$ ratios (i.e., <0.4 and FI of ≥1). In certain embodiments, the compositions of the disclosure reduce or avoid initial burst release ($C_{max}$ above the therapeutic range), while providing therapeutically effective amounts of trihexyphenidyl hydrochloride for periods of at least about 10 hours, e.g., from about 16 hours to about 24 hours.

The following Examples illustrate the disclosure in a nonlimiting manner. Unless indicated to the contrary, the numerical parameters set forth herein can vary depending upon the desired properties sought to be obtained by the present disclosure.

7. EXAMPLES

Example 1: Preparation of Extended Release Trihexyphenidyl Hydrochloride Pellets (5 mg)

The present Example provides a summary of the preparation of twenty-seven different extended release pellets as shown in Tables 1-4. Pellets 18-22 are dose proportional to Pellet 17 and Pellets 24-27 are dose proportional to Pellet 23.

TABLE 1

| Composition | Pellet 1 % w/w (mg) | Pellet 2 % w/w (mg) | Pellet 3 % w/w (mg) | Pellet 4 % w/w (mg) | Pellet 5 % w/w (mg) | Pellet 6 % w/w (mg) | Pellet 7 % w/w (mg) | Pellet 8 % w/w (mg) |
|---|---|---|---|---|---|---|---|---|
| Core | | | | | | | | |
| Tartaric acid | 70.98 (50.0) | 79.50 (200.0) | 65.30 (50.0) | 65.30 (50.0) | 60.47 (50.0) | 65.31 (50.0) | 68.03 (50.0) | 65.36 (50.0) |
| Seal Coat | | | | | | | | |
| Hypromellose (Methocel E5 Premium LV) | 2.73 (1.92) | 3.06 (7.70) | 2.51 (1.92) | 2.51 (1.92) | 2.32 (1.92) | 2.51 (1.92) | 2.61 (1.92) | 2.51 (1.92) |
| Triethyl citrate | 0.14 (0.1) | 0.15 (0.38) | 0.13 (0.1) | 0.13 (0.1) | 0.12 (0.1) | 0.13 (0.1) | 0.14 (0.1) | 0.13 (0.1) |
| Talc | 0.68 (0.47) | 0.76 (0.53) | 0.63 (0.44) | 0.63 (0.44) | 0.58 (0.40) | 0.63 (0.44) | 0.65 (0.46) | 0.63 (0.44) |
| Coating Solvent* | Ethanol: Water (70:30) q.s. | | | | | | | |
| Drug Layer | | | | | | | | |
| Trihexyphenidyl hydrochloride | 7.10 (5.0) | 1.99 (5.0) | 6.53 (5.0) | 6.53 (5.0) | 6.05 (5.0) | 6.53 (5.0) | 6.80 (5.0) | 6.54 (5.0) |
| Hypromellose (Methocel E5 Premium LV) | 4.26 (3.0) | 1.19 (3.0) | 3.92 (3.0) | 3.92 (3.0) | 3.63 (3.0) | 3.92 (3.0) | 4.08 (3.0) | 3.92 (3.0) |
| Triethyl citrate | 0.21 (0.15) | 0.06 (0.15) | 0.20 (0.15) | 0.20 (0.15) | 0.18 (0.15) | 0.20 (0.15) | 0.20 (0.15) | 0.20 (0.15) |
| Talc | 0.85 (0.60) | 0.24 (0.60) | 0.78 (0.60) | 0.78 (0.60) | 0.73 (0.60) | 0.78 (0.60) | 0.82 (0.60) | 0.78 (0.60) |
| Coating Solvent* | Ethanol: Water (80:20) q.s. | | | | | | | |
| Functional Coat | | | | | | | | |
| Ethyl cellulose 20 cps | 8.04 (95.66) | 8.03 (20.19) | 13.07 (10.01) | 13.07 (10.01) | 16.95 (14.02) | NA | 10.26 (7.94) | 13.03 (9.97) |

TABLE 1-continued

| Composition | Pellet 1 % w/w (mg) | Pellet 2 % w/w (mg) | Pellet 3 % w/w (mg) | Pellet 4 % w/w (mg) | Pellet 5 % w/w (mg) | Pellet 6 % w/w (mg) | Pellet 7 % w/w (mg) | Pellet 8 % w/w (mg) |
|---|---|---|---|---|---|---|---|---|
| Eudragit S 100 | NA | NA | NA | NA | NA | 12.30 (9.42) | NA | NA |
| Hypromellose phthalate (HP 55) | 2.00 (1.41) | 2.01 (5.05) | 2.31 (1.77) | NA | 2.99 (2.47) | 3.08 (2.36) | 2.56 (1.88) | 2.30 (1.76) |
| Hypromellose (Methocel E5 Premium LV) | NA | NA | NA | 2.31 (1.77) | NA | NA | NA | NA |
| Triethyl citrate | 1.01 (0.71) | 1.00 (2.52) | 1.54 (1.18) | 1.54 (1.18) | 2.00 (1.65) | 1.54 (1.18) | 1.29 (0.95) | 1.53 1.17 |
| Talc | 2.00 (1.41) | 2.01 (5.05) | 3.08 (2.36) | 3.08 (2.36) | 3.99 (3.30) | 3.07 (2.35) | 2.56 (1.88) | 3.07 (2.35) |
| Coating Solvent* | Ethanol: Water (70:30) q.s. | | | | | | | |
| Total Weight | 100.00 (70.44) | 100.00 (251.56) | 100.00 (76.57) | 100.00 (76.57) | 100.00 (82.69) | 100.00 (76.56) | 100.00 (73.50) | 100.00 (73.56) |

*Removed during process

TABLE 2

| Composition | Pellet 9 % w/w (mg) | Pellet 10 % w/w (mg) | Pellet 11 % w/w (mg) | Pellet 12 % w/w (mg) | Pellet 13 % w/w (mg) | Pellet 14 % w/w (mg) | Pellet 15 % w/w (mg) | Pellet 16 % w/w (mg) |
|---|---|---|---|---|---|---|---|---|
| Core | | | | | | | | |
| Tartaric acid | 58.65 (50.0) | 71.04 (50.0) | 63.79 (50.0) | 57.49 (50.0) | 54.79 (50.0) | 57.35 (50.0) | 52.8 (50.0) | 47.29 (50.0) |
| Seal Coat-1 | | | | | | | | |
| Hypromellose (Methocel E5 Premium LV) | 2.25 (1.92) | 2.73 (1.92) | 2.45 (1.92) | 2.21 (1.92) | 2.10 (1.92) | 2.20 (1.92) | 2.43 (2.30) | 2.72 (2.88) |
| Triethyl citrate | 0.12 (0.10) | 0.14 (0.10) | 0.13 (0.10) | 0.11 (0.10) | 0.11 (0.10) | 0.11 (0.10) | 0.13 (0.12) | 0.14 (0.15) |
| Talc | 0.56 (0.48) | 0.68 (0.48) | 0.61 (0.48) | 0.55 (0.48) | 0.53 (0.48) | 0.55 (0.48) | 0.60 (0.57) | 0.68 (0.72) |
| Coating Solvent* | Ethanol: Water (70:30) q.s. | | | | | | | |
| Drug Layer-1 | | | | | | | | |
| Trihexyphenidyl hydrochloride | 4.99 (4.25) | 7.10 (5.0) | 6.38 (5.0) | 5.75 (5.0) | 5.48 (5.0) | 4.87 (4.25) | 5.39 (5.1) | 6.03 (6.37) |
| Hypromellose (Methocel E5 Premium LV) | 2.99 (2.55) | 4.26 (3.0) | 3.83 (3.0) | 3.45 (3.0) | 3.29 (3.0) | 2.92 (2.55) | 3.23 (3.06) | 3.59 (3.8) |
| Triethyl citrate | 0.18 (0.15) | 0.21 (0.15) | 0.19 (0.15) | 0.17 (0.15) | 0.16 (0.15) | 0.17 (0.15) | 0.19 (0.18) | 0.21 (0.225) |
| Talc | 0.65 (0.55) | 0.85 (0.60) | 0.77 (0.60) | 0.69 (0.60) | 0.66 (0.60) | 0.63 (0.55) | 0.70 (0.66) | 0.78 (0.825) |
| Coating Solvent* | Ethanol: Water (80:20) q.s. | | | | | | | |
| Functional Coat | | | | | | | | |
| Ethyl cellulose 20 cps | 11.50 (9.80) | 8.50 (5.98) | 14.30 (11.21) | 19.34 (16.82) | 21.50 (19.62) | 11.24 (9.8) | 12.43 (11.6) | 13.90 (14.7) |
| Hypromellose phthalate (HP 55) | 2.05 (1.75) | 1.49 (1.05) | 2.51 (1.97) | 3.40 (2.96) | 3.78 (3.45) | 2.01 (1.75) | 2.22 (2.1) | 2.46 (2.6) |
| Triethyl citrate | 1.35 (1.15) | 0.99 (0.70) | 1.68 (1.32) | 2.28 (1.98) | 2.53 (2.31) | 1.32 (1.15) | 1.46 (1.38) | 1.63 (1.72) |
| Talc | 2.70 (2.30) | 1.99 (1.40) | 3.36 (2.63) | 4.55 (3.96) | 5.06 (4.62) | 2.64 (2.30) | 2.92 (2.76) | 3.26 (3.45) |
| Coating Solvent* | Ethanol: Water (70:30) q.s. | | | | | | | |
| Seal Coat-2 | | | | | | | | |
| Hypromellose (Methocel E5 Premium LV) | 3.45 (2.94) | NA | NA | NA | NA | 3.30 (2.88) | 3.65 (3.45) | 4.09 (4.32) |
| Talc | 0.88 (0.75) | NA | NA | NA | NA | 0.83 (0.72) | 0.91 (0.86) | 1.02 (1.08) |

TABLE 2-continued

| Composition | Pellet 9 % w/w (mg) | Pellet 10 % w/w (mg) | Pellet 11 % w/w (mg) | Pellet 12 % w/w (mg) | Pellet 13 % w/w (mg) | Pellet 14 % w/w (mg) | Pellet 15 % w/w (mg) | Pellet 16 % w/w (mg) |
|---|---|---|---|---|---|---|---|---|
| Triethyl citrate | 0.09 (0.08) | NA | NA | NA | NA | 0.17 (0.15) | 0.19 (0.18) | 0.21 (0.225) |
| Coating Solvent* | Ethanol: Water (70:30) q.s. | | | | | | | |
| Drug Layer-2 | | | | | | | | |
| Trihexyphenidyl hydrochloride | 0.88 (0.75) | NA | NA | NA | NA | 0.86 (0.75) | 0.95 (0.9) | 1.06 (1.12) |
| Succinic acid | 0.88 (0.75) | NA | NA | NA | NA | NA | NA | NA |
| Tartaric acid | NA | NA | NA | NA | NA | 1.72 (1.50) | 1.90 (1.80) | 2.13 (2.25) |
| Hypromellose (Methocel E5 Premium LV) | 0.53 (0.45) | NA | NA | NA | NA | NA | NA | NA |
| Copovidone | NA | NA | NA | NA | NA | 1.24 (1.08) | 1.37 (1.30) | 1.53 (1.62) |
| Triethyl citrate | 0.02 (0.02) | NA | NA | NA | NA | NA | NA | NA |
| Talc | 0.53 (0.45) | NA | NA | NA | NA | 1.15 (1.0) | 1.27 (1.2) | 1.42 (1.5) |
| Colloidal silicon dioxide | 0.01 (0.01) | NA | NA | NA | NA | NA | NA | NA |
| Coating Solvent* | Ethanol: Water (80:20) q.s. | | | | | | | |
| Over Coat | | | | | | | | |
| Hypromellose (Methocel E5 Premium LV) | 3.73 (3.18) | NA | NA | NA | NA | 3.61 (3.15) | 4.00 3.78 | 4.46 (4.72) |
| Triethyl citrate | 0.08 (0.07) | NA | NA | NA | NA | 0.18 (0.16) | 0.20 (0.19) | 0.23 (0.24) |
| Talc | 0.94 (0.80) | NA | NA | NA | NA | 0.91 (0.79) | 1.00 (0.95) | 1.14 (1.2) |
| Coating Solvent* | Ethanol: Water (70:30) q.s. | | | | | | | |
| Total Weight | 100.00 (84.53) | 100.00 (70.38) | 100.00 (78.38) | 100.00 (86.97) | 100.00 (91.25) | 100.00 (87.18) | 100.00 (94.6) | 100.00 (105.71) |

*Removed during process

TABLE 3

| Composition | Pellet 17 % w/w (mg) | Pellet 18 (mg) | Pellet 19 (mg) | Pellet 20 (mg) | Pellet 21 (mg) | Pellet 22 (mg) |
|---|---|---|---|---|---|---|
| Core | | | | | | |
| Tartaric acid | 58.53 (50) | 10.0 | 20.0 | 60.0 | 80.0 | 100.0 |
| Seal Coat-1 | | | | | | |
| Hypromellose (Methocel E5 Premium LV) | 2.25 (1.92) | 0.384 | 0.77 | 2.304 | 3.072 | 3.84 |
| Triethyl citrate | 0.12 (0.10) | 0.02 | 0.04 | 0.120 | 0.16 | 0.2 |
| Talc | 0.56 (0.48) | 0.096 | 0.192 | 0.576 | 0.768 | 0.96 |
| Coating Solvent* | Ethanol: Water (70:30) q.s. | | | | | |
| Drug Layer-1 | | | | | | |
| Trihexyphenidyl hydrochloride | 5.41 (4.625) | 0.925 | 1.850 | 5.550 | 7.400 | 9.250 |
| Hypromellose (Methocel E5 Premium LV) | 3.25 (2.775) | 0.555 | 1.110 | 3.330 | 4.440 | 5.550 |
| Triethyl citrate | 0.19 (0.163) | 0.333 | 0.065 | 0.196 | 0.261 | 0.326 |
| Talc | 0.70 (0.599) | 0.120 | 0.239 | 0.718 | 0.958 | 1.197 |
| Coating Solvent* | Ethanol: Water (80:20) q.s. | | | | | |
| Functional Coat | | | | | | |
| Ethyl cellulose 20 cps | 11.60 (9.91) | 1.982 | 3.963 | 11.890 | 15.853 | 19.816 |

TABLE 3-continued

| Composition | Pellet 17 % w/w (mg) | Pellet 18 (mg) | Pellet 19 (mg) | Pellet 20 (mg) | Pellet 21 (mg) | Pellet 22 (mg) |
|---|---|---|---|---|---|---|
| Hypromellose phthalate (HP 55) | 2.07 (1.77) | 0.354 | 0.708 | 2.123 | 2.831 | 3.539 |
| Triethyl citrate | 1.36 (1.16) | 0.233 | 0.465 | 1.395 | 1.860 | 2.325 |
| Talc | 2.72 (2.33) | 0.465 | 0.930 | 2.790 | 3.721 | 4.651 |
| Coating Solvent* | Ethanol: Water (70:30) q.s. | | | | | |
| Seal Coat-2 | | | | | | |
| Hypromellose (Methocel E5 Premium LV) | 3.46 (2.96) | 0.591 | 1.183 | 3.548 | 4.731 | 5.913 |
| Talc | 0.88 (0.75) | 0.151 | 0.302 | 0.905 | 1.207 | 1.508 |
| Triethyl citrate | 0.09 (0.08) | 0.016 | 0.032 | 0.097 | 0.129 | 0.161 |
| Coating Solvent* | Ethanol: Water (70:30) q.s. | | | | | |
| Drug layer-2 | | | | | | |
| Trihexyphenidyl hydrochloride | 0.44 (0.375) | 0.075 | 0.15 | 0.45 | 0.60 | 0.75 |
| Succinic acid | 0.44 (0.375) | 0.075 | 0.15 | 0.45 | 0.60 | 0.75 |
| Hypromellose (Methocel E5 Premium LV) | 0.14 (0.113) | 0.023 | 0.05 | 0.14 | 0.18 | 0.23 |
| Triethyl citrate | 0.02 (0.02) | 0.004 | 0.01 | 0.02 | 0.03 | 0.04 |
| Talc | 0.53 (0.450) | 0.090 | 0.18 | 0.54 | 0.72 | 0.90 |
| Colloidal silicon dioxide | 0.01 (0.010) | 0.002 | 0.00 | 0.01 | 0.02 | 0.02 |
| Coating Solvent* | Ethanol: Water (80:20) q.s. | | | | | |
| Over Coat (5% of IR layered pellets) | | | | | | |
| Hypromellose (Methocel E5 Premium LV) | 3.73 (3.18) | 0.636 | 1.27 | 3.82 | 5.09 | 6.36 |
| Triethyl citrate | 0.08 (0.07) | 0.014 | 0.03 | 0.08 | 0.11 | 0.14 |
| Talc | 0.94 (0.80) | 0.160 | 0.32 | 0.96 | 1.28 | 1.60 |
| Total weight | 99.52 (85.01) | 17.004 | 34.009 | 102.012 | 135.969 | 170.026 |
| Coating Solvent* | Ethanol: Water (70:30) q.s. | | | | | |
| Final Blend | | | | | | |
| THP over coated pellets | 99.52 (102.01) | 17.002 | 34.004 | 102.013 | 136.018 | 170.022 |
| Colloidal silicon dioxide | 0.24 (0.25) | 0.042 | 0.08 | 0.25 | 0.33 | 0.42 |
| Talc | 0.24 (0.25) | 0.042 | 0.08 | 0.25 | 0.33 | 0.42 |
| Total fill weight in capsule | 100.00 (102.51) | 17.086 | 34.171 | 102.513 | 136.684 | 170.855 |

*Removed during process

TABLE 4

| Composition | Pellet 23 (mg) | Pellet 24 (mg) | Pellet 25 (mg) | Pellet 26 (mg) | Pellet 27 (mg) |
|---|---|---|---|---|---|
| Tartaric acid | 10.0 | 20.0 | 60.0 | 80.0 | 100.0 |
| Seal Coat | | | | | |
| Hypromellose (Methocel E5 Premium LV) | 0.384 | 0.768 | 2.304 | 3.072 | 3.840 |
| Triethyl citrate | 0.020 | 0.040 | 0.120 | 0.160 | 0.200 |
| Talc | 0.096 | 0.192 | 0.576 | 0.768 | 0.960 |
| Coating Solvent* | Ethanol:Water (70:30) | | | | |
| Drug Layer | | | | | |
| Trihexy-phenidyl hydrochloride | 1.00 | 2.00 | 6.00 | 8.00 | 10.00 |
| Hypromellose (Methocel E5 Premium LV) | 0.600 | 1.20 | 3.60 | 4.80 | 6.00 |
| Triethyl citrate | 0.03 | 0.06 | 0.18 | 0.24 | 0.30 |
| Talc | 0.12 | 0.24 | 0.72 | 0.96 | 1.20 |
| Coating Solvent* | Ethanol:Water (80:20) | | | | |
| Functional Coat | | | | | |
| Ethyl cellulose (ETHOCEL 20 Premium) | 2.00 | 4.00 | 12.00 | 16.00 | 20.00 |
| Hypromellose phthalate (HP 55) | 0.350 | 0.70 | 2.10 | 2.80 | 3.50 |

TABLE 4-continued

| Composition | Pellet 23 (mg) | Pellet 24 (mg) | Pellet 25 (mg) | Pellet 26 (mg) | Pellet 27 (mg) |
|---|---|---|---|---|---|
| Triethyl citrate | 0.23 | 0.46 | 1.38 | 1.84 | 2.30 |
| Talc | 0.47 | 0.94 | 2.80 | 3.76 | 4.70 |
| Coating Solvent* | | | Ethanol:Water (70:30) | | |
| Total Weight Final Blend | 15.30 | 30.60 | 91.80 | 122.40 | 153.00 |
| THP HCl Functional coated pellets | 15.30 | 30.60 | 91.80 | 122.40 | 153.00 |
| Colloidal silicon dioxide (CAB-O-SIL) | 0.10 | 0.20 | 0.60 | 0.80 | 1.00 |
| Talc | 0.10 | 0.20 | 0.60 | 0.80 | 1.00 |
| Total Weight | 15.50 | 31.00 | 93.00 | 124.00 | 155.00 |

*Removed during process

The pellets were made according to the following manufacturing procedure.

Manufacturing Procedure:

A. Seal Coat-1:
A-1: Hypromellose was added to a mixture of ethanol (200 proof) and water (70:30 w/w ratio) in a stainless-steel container and mixed until a clear solution was obtained.
A-2: To the clear solution from step #A-1, triethyl citrate was added and mixed for not less than 15 minutes to obtain a clear solution.
A-3: To the clear solution from step #A-2, talc was added and mixed until a uniform dispersion was obtained.
A-4: Cores comprising tartaric acid were taken in a Wurster chamber and seal coated with the dispersion from step #A-3 until target coating weight gain was achieved.

B. Drug Layer-1:
B-1: Trihexyphenidyl hydrochloride was added to a mixture of ethanol (200 proof) and water (80:20 w/w ratio) in a stainless-steel container and mixed until a clear solution was obtained.
B-2: To the clear solution from step #B-1, hypromellose was added with constant stirring and mixed until a clear solution was obtained.
B-3: To the clear solution from step #B-2, triethyl citrate was added and mixed for not less than 15 minutes to obtain a clear solution.
B-4: To the clear solution from step #B-3, talc was added and mixed until a uniform dispersion was obtained.
B-5: Seal coated pellets from procedure A were taken in a Wurster chamber and coated with the dispersion from step #B-4.

C. Functional Coat:
C-1: Ethyl cellulose or Eudragit S100 was added to ethanol (200 proof) in a stainless-steel container and mixed until a clear solution was obtained.
C-2: To the clear solution from step #C-1, water was added and mixed for not less than 30 minutes to obtain a clear solution.
C-3: To the clear solution from step #C-2, hypromellose phthalate or hypromellose was added and mixed until a clear or light hazy solution was obtained.
C-4: To the solution from step #C-3, triethyl citrate was added and mixed for not less than 15 minutes to obtain a clear solution.
C-5: To the clear solution from step #C-4, talc was added and mixed to obtain a uniform dispersion.
C-6: Drug layered pellets from procedure B were taken in a Wurster chamber and coated with the dispersion from step #C-5 until target coating weight gain was achieved.
C-7: Functional coated pellets from step #C-6 were dried between about 25° C. and about 30° C.

D. Seal Coat-2:
D-1: Hypromellose was added to a mixture of ethanol 200 proof and water (70:30 w/w ratio) in a stainless-steel container and mixed until a clear solution was obtained.
D-2: To the solution from step #D-1, triethyl citrate was added and mixed for not less than 15 minutes to obtain a clear solution.
D-3: To the solution from step #D-2, talc was added and mixed until a uniform dispersion was obtained.
D-4: Functional coated pellets (pellets 9, and 14-22) from Step C were taken in a Wurster chamber and seal coated with the dispersion from step #D-3 until target coating weight gain was achieved.

E. Drug Layer-2:
E-1: Trihexyphenidyl hydrochloride and succinic acid were added to a mixture of ethanol (200 proof) and water (80:20 w/w ratio) in a stainless-steel container and mixed to form a clear solution.
E-2: To the solution from step #E-1, hypromellose was added with constant stirring and mixed until a clear solution was obtained.
E-3: To the solution from step #E-2, triethyl citrate was added and mixed for not less than 15 minutes to obtain a clear solution.
E-4: To the clear solution from step #E-3, colloidal silicon dioxide and talc were added and mixed until a uniform dispersion was obtained.
E-5: Pellets with seal coat-2 (Pellets 9 and 14-22) from Step D were taken in a Wurster chamber and coated with the dispersion from step #E-4.

F. Over Coat:
F-1: Hypromellose was added to a mixture of ethanol 200 proof and water (70:30 w/w ratio) in a stainless-steel container and mixed until a clear solution was obtained.
F-2: To the solution from step #F-1, triethyl citrate was added and mixed for not less than 15 minutes to obtain a clear solution.
F-3: To the clear solution from step #F-2, talc was added and mixed until a uniform dispersion was obtained.
F-4: Pellets with drug layer-2 (Pellets 9 and 14-22) from Step E were taken in a Wurster chamber and coated with the dispersion from step #F-3 until target coating weight gain was achieved.

G. Trihexyphenidyl Hydrochloride Capsules:
G-1: A final blend of functional coated pellets (from Step C or Step F) along with talc and/or colloidal silicon dioxide was prepared using a V-Blender and then filled into hard gelatin capsules based on the required fill weight.

Example 2: Additional Compositions

Pellets 28-33 are made according to the manufacturing procedure described in Example 1. Pellets 28 and 29 contain drug:acid weight ratio of 1:50 and 1:100, respectively. Both pellets include a functional coating weight gain of about 25% w/w, based on the total weight of the pellet without functional coat; and a water-insoluble polymer:pore former weight ratio of 85:15. Pellet 30 and 31 include water-insoluble polymer:pore former weight ratio of 50:50 and 98:2, respectively. Both pellets contain a drug:acid weight ratio of 1:10, and a functional coating weight gain of about 25% w/w, based on the total weight of the pellet without functional coat. Pellet 32 and 33 contain a functional coating weight gain of about 5% w/w and about 40% w/w, respectively, based on the total weight of the pellet without the functional coat. Both pellets contain a drug:acid weight ratio of 1:10, and a water-insoluble polymer:pore former weight ratio of 85:15.

TABLE 5

| Composition | Pellet 28 (mg) | Pellet 29 (mg) | Pellet 30 (mg) | Pellet 31 (mg) | Pellet 32 (mg) | Pellet 33 (mg) |
|---|---|---|---|---|---|---|
| Tartaric acid | 50 mg | 100 mg | 10 mg | 10 mg | 10 mg | 10 mg |
| Seal Coat | | | | | | |
| Hypromellose (Methocel E5 Premium LV) | 1.92 | 3.840 | 0.3840 | 0.3840 | 0.3840 | 0.3840 |
| Triethyl citrate | 0.1 | 0.2 | 0.02 | 0.02 | 0.02 | 0.02 |
| Talc | 0.48 | 0.96 | 0.096 | 0.096 | 0.096 | 0.096 |
| Drug Layer | | | | | | |
| Trihexyphenidyl hydrochloride | 1.00 | 1.00 | 1.00 | 1.00 | 1.00 | 1.00 |
| Hypromellose (Methocel E5 Premium LV | 0.6 | 0.6 | 0.6 | 0.6 | 0.6 | 0.6 |
| Triethyl citrate | 0.03 | 0.03 | 0.03 | 0.03 | 0.03 | 0.03 |
| Talc | 0.12 | 0.12 | 0.12 | 0.12 | 0.12 | 0.12 |
| Total Weight | 54.25 | 106.8 | 12.25 | 12.25 | 12.25 | 12.25 |
| Functional Coat | | | | | | |
| Ethyl cellulose (ETHOCEL 20 Premium) | 8.87 | 17.46 | 1.175 | 2.30 | 0.40 | 4.00 |
| Hypromellose phthalate (HP 55) | 1.56 | 3.08 | 1.175 | 0.05 | 0.07 | 0.71 |
| Triethyl citrate | 1.04 | 2.05 | 0.23 | 0.23 | 0.05 | 0.47 |
| Talc | 2.08 | 4.11 | 0.47 | 0.47 | 0.09 | 0.94 |
| Total Weight | 67.80 | 133.5 | 15.3 | 15.3 | 12.86 | 18.37 |
| Final Blend | | | | | | |
| THP HCl Functional coated pellets | 67.82 | 133.5 | 15.3 | 15.30 | 12.86 | 18.37 |
| Talc | 0.44 | 0.87 | 0.1 | 0.1 | 0.08 | 0.12 |
| Colloidal silicon dioxide (CAB-O-SIL) | 0.44 | 0.87 | 0.1 | 0.1 | 0.08 | 0.12 |
| Total Weight | 68.70 | 135.24 | 15.5 | 15.5 | 13.03 | 18.6 |

*Removed during process

Example 3: Comparison of Dissolution Profiles of Trihexyphenidyl Hydrochloride (API (Control)) and Trihexyphenidyl Hydrochloride Drug-Layered Pellets, without Functional Coat Dissolution tests were performed for trihexyphenidyl hydrochloride (API (control)) and for trihexyphenidyl hydrochloride drug-layered pellets (Pellets 1A-1D). Pellet 1A is drug layered Pellet 1 without functional coat and containing about 25% drug layer weight gain, based on the total weight of the seal coated pellet without the drug layer. Pellet 1B is drug layered Pellet 1 without functional coat and containing about 50% drug layer weight gain, based on the total weight of the seal coated pellet without the drug layer. Pellet 1C is drug layered Pellet 1 without functional coat and containing about 75% drug layer weight gain, based on the total weight of the seal coated pellet without the drug layer. Pellet 1D is drug layered Pellet 1 without functional coat and containing about 100% drug layer weight gain, based on the total weight of the seal coated pellet without the drug layer. The dissolutions were performed in an incubator orbital shaker, in 20 ml of pH 6.8 phosphate buffer at 37° C. Drug release was measured using high performance liquid chromatography (HPLC) for API (control) and tartaric acid pellets 1A-1D at 5, 10, 20, 30, and 60 minutes.

FIG. 1 shows the effects of tartaric acid on solubility of trihexyphenidyl hydrochloride at pH 6.8. FIG. 1 demonstrates that tartaric acid provides an acidic microenvironmental pH for improving dissolution of trihexyphenidyl hydrochloride at pH 6.8. API (control) without any tartaric acid, released about 0.66 mg/ml of trihexyphenidyl hydrochloride at 5 minutes, whereas the drug-layered pellets with 25% drug layer weight gain released about 1.9 mg/ml of trihexyphenidyl hydrochloride at 5 minutes, and the drug-layered pellets with 50, 75, and 100% drug layer weight gain released about 1.7 mg/ml of trihexyphenidyl hydrochloride at 5 minutes. FIG. 1 demonstrates that presence of tartaric acid-containing cores increased the amount of THP released at a pH of about 5 or above. The figure further demonstrates that increasing the amount of drug layer reduced the amount of THP released at a pH of about 5 or above.

TABLE 6

| Composition | Pellet 1A (mg) | Pellet 1B (mg) | Pellet 1C (mg) | Pellet 1D (mg) |
|---|---|---|---|---|
| Tartaric acid | 50.00 | 50.00 | 50.00 | 50.00 |
| Seal Coat | | | | |
| Hypromellose (Methocel E5 Premium LV) | 1.92 | 1.92 | 1.92 | 1.92 |
| Triethyl citrate | 0.10 | 0.10 | 0.10 | 0.10 |
| Talc | 0.60 | 0.60 | 0.60 | 0.60 |
| Total weight | 52.62 | 52.62 | 52.62 | 52.62 |
| Drug Layer | | | | |
| Trihexyphenidyl hydrochloride | 8.30 | 16.60 | 24.90 | 33.20 |
| Hypromellose (Methocel E5 Premium LV) | 5.00 | 10.00 | 15.00 | 20.00 |
| Triethyl citrate | 0.25 | 0.50 | 0.75 | 1.00 |
| Talc | 1.00 | 2.00 | 3.00 | 4.00 |
| Total drug layer weight (mg) | 14.55 | 29.10 | 43.65 | 58.20 |

Example 4: Effect of Functional Coat on Release Rate of Trihexyphenidyl Hydrochloride Two-stage dissolution tests for trihexyphenidyl hydrochloride capsules containing THP pellets of the disclosure without any functional coat, and capsules containing THP pellets of the disclosure with 13% wt gain of the functional coat, were performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. Samples were collected at regular intervals of time, and drug release was measured using HPLC. The results are shown in FIG. 2. As illustrated by FIG. 2, the functional coat helped to reduce and/or prevent the initial burst release of trihexyphenidyl hydrochloride and provided a more even release of the THP HCl— Pellet 1 without a functional coat provided faster dissolution/higher dissolution rate compared to the Pellet 1 with a functional coat.

Example 5: Effect of Trihexyphenidyl Hydrochloride and Tartaric Acid Weight Ratio on the Release Rate of Trihexyphenidyl Hydrochloride Two-stage dissolution tests for THP HCl capsules containing the formulation of Pellet 1, and THP HCl capsules containing the formulation of Pellet 2, were performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. Pellets 1 and 2 contained about 13% coating wt gain of functional coat. Pellet 1 contained a tartaric acid: THP HCl weight ratio of about 10:1, and Pellet 2 contained a tartaric acid:THP HCl weight ratio of about 40:1. Samples were collected at regular intervals of time and drug release was measured using HPLC. FIG. 3 demonstrates that Pellet 2 formulation, with a tartaric acid to THP HCl weight ratio of 40:1, provided a much higher dissolution rate compared to Pellet 1 formulation, with a tartaric acid to THP HCl weight ratio of 10:1, indicating that the amount of acid in the core was directly proportional to the dissolution rate of the drug at pH 6.8.

Example 6: Comparison of Trihexyphenidyl Hydrochloride Release Profile from Pellet 1 Formulation and Marketed IR Trihexyphenidyl Hydrochloride Tablets, 5 Mg, in pH 6.8 Phosphate Buffer Dissolution tests for THP HCl capsules containing Pellet 1 formulation and marketed IR THP HCl tablets, 5 mg, were performed using USP Apparatus I at 100 RPM and 37° C., in 900 ml of pH 6.8 phosphate buffer for 24 hours. Samples were collected at regular intervals of time and drug release was measured using HPLC. FIG. 4 compares dissolution profiles of Pellet 1 formulation and marketed IR THP HCl tablets (5 mg). FIG. 4 demonstrates that the marketed IR THP HCl tablet provided faster dissolution of THP HCl compared to Pellet 1 formulation. FIG. 4 demonstrates that the marketed THP HCl tablet provided initial burst release of THP, whereas the Pellet 1 formulation provided controlled release, no initial burst release, of THP. The slow release of trihexyphenidyl from the Pellet 1 formulation was attributed to the presence of controlled release membrane comprising ethyl cellulose and hypromellose phthalate (HP 55). Further, tartaric acid provided an acidic microenvironmental pH for improving solubility and recovery (by the end of 24 hours) of THP HCl, even at pH 6.8.

Example 7: Effect of Ethyl Cellulose and Hypromellose Phthalate Weight Ratio on Trihexyphenidyl Hydrochloride Dissolution Profile Two-stage dissolution tests for capsules containing Pellet 7 [ethyl cellulose:hypromellose phthalate (80:20)] formulation, and for capsules containing Pellet 8 [ethyl cellulose:hypromellose phthalate (85:15)] formulation were performed using USP Apparatus I at 100 RPM and 37° C., in 900 ml of 0.01 N HCl for one hour followed by dissolution in 900 ml of pH 6.8 phosphate buffer for 24 hours, to simulate physiological conditions. Pellet 7 contained functional coat containing ethyl cellulose:hypromellose phthalate weight ratio of about 80:20 at about 20% functional coating weight gain, based on the total weight of the pellet without the functional coat, Pellet 8 contained a functional coat containing ethyl cellulose:hypromellose phthalate weight ratio of about 85:15 at about 25% functional coating weight gain, based on the total weight of the pellet without functional coat. Samples were collected at regular intervals of time and drug release was measured using HPLC. FIG. 5 compares the dissolution profiles of capsules containing Pellets 7 and 8 respectively. FIG. 5 demonstrates that Pellet 8 containing ethyl cellulose:hypromellose phthalate weight ratio of 85:15 at 25% functional coating weight gain provided a reduced drug release rate and more controlled release compared to pellet 7 containing ethyl cellulose:hypromellose phthalate weight ratio of about 80:20 at 20% functional coating weight gain. FIG. 5 demonstrates that release of THP HCl is reduced with increase in functional coating weight gain.

Example 8: Effect of Functional Coat Weight Gain on Release Rate of Trihexyphenidyl Hydrochloride Two-stage dissolution tests for trihexyphenidyl hydrochloride capsules containing pellets 5, 11, 12, and 13 with about 25%, about 20%, about 30%, and about 35% coating weight gain of functional coat, respectively, based on the total weight of the corresponding pellets without the functional coat, were performed using USP Apparatus I at 100

RPM and 37° C., in 900 ml of pH 1.2 medium for 1 hour followed by dissolution in 900 ml of pH 6.8 phosphate buffer for 24 hours, to simulate physiological conditions. Samples were collected at regular intervals of time, and drug release was measured using HPLC. The ratio of nonionic water-insoluble polymer:pore former in all pellets was about 85:15. The results of the Experiment are illustrated in FIG. 6. FIG. 6 demonstrates that the drug release rate increased with decreasing functional coat weight gain. Pellets with 20% wt gain of the functional coat provided maximum release rate and recovery of THP HCl, and pellets with 35% wt gain of the functional coat provided lowest release rate and recovery of THP HCl.

Example 9: Comparison of Trihexyphenidyl Hydrochloride Release Profile from Pellets with and without an Immediate Release Drug Layer Two-stage dissolution tests for trihexyphenidyl hydrochloride capsules containing Pellets 5, 15, and 16 were performed using USP Apparatus I at 100 RPM and 37° C., in 900 ml of pH 1.2 HCl for one hour followed by dissolution in 900 ml of pH 6.8 phosphate buffer for 24 hours, to simulate physiological conditions. Samples were collected at regular intervals of time, and drug release was measured using HPLC. Pellet 5 contained 5 mg of trihexyphenidyl hydrochloride in drug layer-1 (ER layer) and contained no drug layer-2 (IR layer); Pellet 15 contained 5.1 mg of trihexyphenidyl hydrochloride in drug layer-1 and 0.9 mg of trihexyphenidyl hydrochloride in drug layer-2; and Pellet 16 contained 6.37 mg of trihexyphenidyl hydrochloride in drug layer-1 and 1.125 mg of trihexyphenidyl hydrochloride in drug layer-2. FIG. 7 demonstrates that Pellet 5 (without drug layer-2) provided a lag time to therapeutic drug concentration of about 2 hours, and Pellets 15 and 16 (containing drug layer-2) provided a lag time to therapeutic drug concentration of about 30 minutes.

Example 10: Comparison of Dissolution Profile of Pellets Containing a Combination of pH Independent Water-Insoluble Polymer and an Enteric Polymer; a Combination of a pH Independent Water-Insoluble and a pH Independent Water-Soluble Polymer; and Pellets Containing a Combination of Two Enteric Polymers Two-stage dissolution tests for trihexyphenidyl hydrochloride capsules containing Pellet 3 [ethyl cellulose:hypromellose phthalate (85:15)] formulation, trihexyphenidyl hydrochloride capsules containing Pellet 4 [ethyl cellulose: hypromellose (85:15)] formulation, and trihexyphenidyl hydrochloride capsules containing Pellet 6 [Eudragit® S 100:Hypromellose phthalate (85:15)] formulation were performed using USP Apparatus I at 100 RPM and 37° C., in 900 ml of pH 1.2 medium for one hour followed by dissolution in 900 ml of pH 6.8 phosphate buffer for 24 hours, to simulate physiological conditions. Samples were collected at regular intervals of time and drug release was measured using HPLC. FIG. 9 compares the two-stage dissolution profiles of Pellets 3, 4, and 6. FIG. 9 demonstrates that the type of water-insoluble polymer and the type of pore former in the functional coat plays a critical role in controlling the release rate of trihexyphenidyl hydrochloride. FIG. 9 demonstrates that Pellet 3 containing ethocel and hypromellose phthalate (HP 55) provided more controlled release of the drug compared to Pellet 4 containing ethocel and hypromellose (Methocel E5 Prem LV), and Pellet 6 containing Eudragit S100 and hypromellose phthalate (HP 55) in the functional coat.

Example 11: Oral Bioavailability of THP HCl from Extended Release Compositions of the Disclosure A single dose pharmacokinetic (PK) study was conducted in healthy volunteers under fed conditions to evaluate and compare the PK performance of extended release THP HCl capsules containing Pellet 8 (5 mg) of the present disclosure with a marketed immediate release THP HCl reference product R (5 mg). An open label, balanced, randomized, two-treatment, two-period, two-sequence, single oral dose, two-way crossover bioequivalence study of reference product R (IR THP HCl tablets, 5 mg) with capsules containing Pellet 8 was conducted in 14 normal healthy adult human subjects under high fat-high calorie conditions after 10 hour overnight fasting.

Pharmacokinetic results from the study are summarized below.

TABLE 7

| Pharmacokinetic | Geometric Mean | |
|---|---|---|
| Parameters | Capsules with Pellet 8 | Reference Product R |
| Cmax (ng/ml) | 7.808 | 31.879 |
| Cmin (ng/ml) | 6.162 | 6.50 |
| Cav (ng/ml) | 5.17 | 12.56 |
| FI | 0.326 | 1.99 |
| $AUC_{0-t}$ (hr · ng/ml) | 171.521 | 318.511 |
| $AUC_{0-\infty}$ (hr · ng/ml) | 281.227 | 454.522 |
| Tmax (h)* | 6.00 | 2.00 |

*median (min-max)

The data from Table 7/FIG. 10 demonstrates that the extended release THP capsules containing Pellet 8 provided a Cmin:Cmax ratio of >0.4 and FI of <1 and provided therapeutic concentrations of THP HCl over at least about 16 hours, and the immediate release reference product R provided a Cmin:Cmax ratio of <0.4 and FI>1. $C_{max}$ of the extended release capsules containing Pellet 8 was about 25% of the immediate release reference product R.

Example 12: Oral Bioavailability of THP HCl from Extended Release Compositions of the Disclosure A single dose pharmacokinetic (PK) study was conducted in healthy volunteers under fed conditions to evaluate and compare the PK performance of extended release THP HCl composition (6 mg) of the present disclosure, administered once-a-day, with marketed immediate release THP HCl product (2 mg)/reference product R, administered 3 times-a-day. An open label, balanced, non-randomized, two-treatment, two-period, single-sequence, crossover oral bioavailability study of reference product R, administered three time-a-day (IR THP HCl tablets, 2 mg×3), with extended release capsules containing Pellet 17, at pellet weight adjusted to 6 mg strength and a fill weight of about 102.5 mg, administered once-a-day, was conducted in 20 normal healthy adult human subjects under high fat-high calorie conditions after 10 hour overnight fasting.

Pharmacokinetic results from the study are summarized below.

TABLE 8

| Pharmacokinetic Parameters | Geometric Mean | |
|---|---|---|
| | Capsules with Pellet 17 | Reference Product (R) |
| Cmax (ng/ml) | 12.050 | 13.190 |
| $AUC_{0-t}$ (hr · ng/ml) | 229.787 | 252.89 |
| $AUC_{0-\infty}$ (hr · ng/ml) | 294.863 | 345.228 |
| Tmax (h)* | 4.00 | 17.75 |

*median (min-max)

PK data from Table 8/FIG. 11 demonstrates that the extended release THP capsules (6 mg), administered once-a-day, provided substantially reduced $C_{max}$-to-$C_{min}$ fluctuations (e.g., $C_{min}:C_{max}$ ratio of ≥0.4), while providing therapeutic concentrations of THP HCl over about 24 hours, compared to marketed immediate release 2 mg THP tablets/reference product R, administered three-times-a-day ($C_{min}:C_{max}$ ratio of <0.4). The PK data further suggests that under fed conditions, the test product (extended release THP HCl composition (6 mg) of the present disclosure, administered once-a-day) and the reference product R(immediate release THP HCl product (2 mg), administered 3 times-a-day), provided similar bioavailability (Test $AUC_{0-\infty}$/Reference $AUC_{0-\infty}$ is ~92%).

Example 13: Oral Bioavailability of THP HCl from Extended Release Compositions of the Disclosure Under Fed and Fasted Conditions A single dose pharmacokinetic (PK) study was conducted in healthy volunteers, under fed and fasting conditions, to evaluate and compare the PK performance, under fed and fasted conditions, of extended release THP HCl composition (6 mg) of the present disclosure, with marketed immediate release THP HCl product/reference product R (2 mg). An open label, balanced, randomized, two-treatment, two-period, two groups, single oral dose, two-sequence, two-way crossover oral bioavailability study of extended release capsules containing Pellet 25 (6 mg THP) and of reference product R, was conducted in normal healthy adult human subjects under fed and fasting conditions.

Pharmacokinetic results from the study are summarized below.

TABLE 9

| Pharmacokinetic Parameters | Geometric Mean | | | |
|---|---|---|---|---|
| | Test product | | Reference Product (R) | |
| Pharmacokinetic Parameters | Fed Condition | Fasting Condition | Fed Condition | Fasting Condition |
| Cmax (ng/ml) | 13.8 | 9.4 | 12.3 | 17.9 |
| $AUC_{0-\infty}$ (hr · ng/ml) | 431.8 | 335.6 | 214.4 | 166 |

PK data from Table 9, suggest that the test product and reference product R have similar food effect on bioavailability (Fasting $AUC_{0-\infty}$/Fed $AUC_{0-\infty}$ is ~78%).

Table 10/FIG. 15 provides PK data for extended release capsules containing Pellet 25 (6 mg THP HCl, QD dosing) and of reference product R (QD dosing simulated for TID, 2 mg×3), in normal healthy adult human subjects under fed conditions.

TABLE 10

| | FED CONDITION | | | | | |
|---|---|---|---|---|---|---|
| | $C_{max}$ | $C_{min}$ | $C_{min}/C_{max}$ | Cav | FI | $AUC_{0-24}$ |
| Reference (R)- N = 18 | 16.57 | 5.08 | 0.306 | 10.13 | 1.13 | 254.4 |
| Capsules with Pellet 25 (T) N = 18 | 13.08 | 6.98 | 0.533 | 6.74 | 0.90 | 179.8 |

Table 11/FIG. 16 provides PK data for extended release capsules containing Pellet 25 (6 mg THP HCl) and of reference product R (QD dosing simulated for TID, 2 mg×3), in normal healthy adult human subjects under fasting conditions.

TABLE 11

| | FASTING CONDITION | | | | | |
|---|---|---|---|---|---|---|
| | $C_{max}$ | $C_{min}$ | $C_{min}/C_{max}$ | Cav | FI | $AUC_{0-24}$ |
| Reference (R)- N = 18 | 20.12 | 2.83 | 0.14 | 9.16 | 1.89 | 216.6 |
| Capsules with Pellet 25 (T) N = 18 | 9.4 | 4.78 | 0.508 | 5.41 | 0.81 | 134.2 |

The data from 10/FIG. 15 and Table 11/FIG. 16 demonstrates that the extended release THP capsules (6 mg), administered once-a-day, provided substantially reduced $C_{max}$-to-$C_{min}$ fluctuations (e.g., $C_{min}:C_{max}$ ratio of ≥0.4 and FI of ≤1), while providing therapeutic concentrations of THP HCl over about 24 hours, compared to marketed immediate release 2 mg THP tablets/reference product R, administered three-times-a-day.

The present disclosure is well adapted to attain the ends and advantages mentioned, as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified, and all such variations, including but not limited to substitution of different trihexyphenidyl salts, are considered within the scope and spirit of the present disclosure. Various publications, patents, and patent application are cited herein, the contents of which are hereby incorporated-by-reference herein in their entireties.

The invention claimed is:

1. A pharmaceutical pellet composition comprising:
   a) a core comprising at least one organic acid;
   b) a drug layer covering at least a portion of the core; and
   c) a functional coat covering at least a portion of the drug layer,
   wherein the drug layer comprises trihexyphenidyl or a pharmaceutically acceptable salt thereof, and a nonionic water-soluble polymer,
   wherein the functional coat comprises a nonionic water-insoluble polymer, and a pore former, wherein the water-insoluble polymer and the pore former are present in a weight ratio of from about 60:40 to about 98:2, and wherein the composition provides extended release with a $C_{min}$:$C_{max}$ ratio of ≥0.4.

2. The composition of claim 1, wherein the composition provides and maintains at least a minimum therapeutic plasma concentration of the trihexyphenidyl or the pharmaceutically acceptable salt thereof during the extended release.

3. The composition of claim 1, wherein the minimum therapeutic plasma concentration is a minimum concentration of the trihexyphenidyl or the pharmaceutically acceptable salt thereof that can provide a therapeutically useful response in a subject.

4. The composition of claim 1, wherein the composition provides a Fluctuation Index of ≤1.

5. The composition of claim 1, wherein the core is a pellet, bead, seed, or a granule comprising at least one organic acid.

6. The composition of claim 1, wherein the core is a pellet, bead, seed, or a granule coated with at least one coating comprising at least one organic acid.

7. The composition of claim 1, wherein the core is an organic acid or a mixture of organic acids.

8. The composition of claim 1, wherein the first drug layer comprises trihexyphenidyl hydrochloride.

9. The composition of claim 1, wherein the composition is suitable for once-a-day administration.

10. The composition of claim 1, wherein the organic acid is selected from the group consisting of tartaric acid, citric acid, fumaric acid, succinic acid, malic acid, and mixtures thereof.

11. The composition of claim 1, wherein the nonionic water-soluble polymer in the drug layer is selected from the group consisting of hydroxypropyl cellulose, methyl cellulose, hydroxypropyl methylcellulose, hydroxyethyl cellulose, polyethylene glycol, polyvinyl alcohol, poloxamer, polyvinyl pyrrolidone-vinyl acetate copolymer, and mixtures thereof.

12. The composition of claim 1, wherein the nonionic water-insoluble polymer in the functional coat is selected from the group consisting of ethyl cellulose, cellulose acetate, cellulose diacetate, cellulose triacetate, cellulose propionate, a polyvinyl acetate dispersion, and mixtures thereof.

13. The composition of claim 1, wherein the pore former is an enteric polymer selected from the group consisting of cellulose acetate phthalate, cellulose acetate succinate, methylcellulose phthalate, hydroxyethyl cellulose phthalate, polyvinyl acetate phthalate, polyvinyl butyrate acetate, vinyl acetate-maleic anhydride copolymer, methacrylic acid copolymer, hydroxypropyl methylcellulose phthalate, polyvinyl acetate phthalate, cellulose acetyl phthalate, and mixtures thereof.

14. The composition of claim 1, wherein the pore former is a nonionic, pH-independent water-soluble polymer selected from the group consisting of methyl cellulose, hydroxypropyl cellulose, hydroxypropyl methylcellulose, hydroxyethyl cellulose, polyethylene glycol, polyvinyl alcohol, poloxamer, polyvinyl pyrrolidone-vinyl acetate copolyme, and mixtures thereof.

15. The composition of claim 1, wherein the drug layer further comprises at least one organic acid selected from the group consisting of tartaric acid, citric acid, fumaric acid, succinic acid, malic acid, and mixtures thereof.

16. A pharmaceutical composition comprising:
a) a core comprising at least one organic acid;
b) a drug layer covering at least a portion of the core; and
c) a functional coat covering at least a portion of the drug layer,
wherein the drug layer comprises trihexyphenidyl or a pharmaceutically acceptable salt thereof, and a nonionic water-soluble polymer,
wherein the functional coat comprises a nonionic water-insoluble polymer, and a pore former, wherein the water-insoluble polymer and the pore former are present in a weight ratio of from about 60:40 to about 98:2, and
wherein the composition provides a Fluctuation Index of ≤1.

17. The composition of claim 16, wherein the core is an organic acid or a mixture of organic acids.

18. The composition of claim 16, wherein the core comprises at least one organic acid.

19. The composition of claim 16, wherein the core is a pellet, bead, seed, or a granule coated with at least one coating comprising at least one organic acid.

20. A method for making a pharmaceutical pellet composition comprising trihexyphenidyl or a pharmaceutically acceptable salt thereof, the method comprising:
a) coating a core comprising at least one organic acid, with a drug layer comprising trihexyphenidyl or a pharmaceutically acceptable salt thereof, and a nonionic water-soluble polymer, to obtain a drug layered core,
b) coating the drug layered core with a functional coat comprising a nonionic water-insoluble polymer, and a pore former;
wherein the water-insoluble polymer and the pore former are present in a weight ratio of from about 60:40 to about 98:2, and
wherein the composition provides extended release with a $C_{min}$:$C_{max}$ ratio of ≥0.4.

21. The method of claim 20, wherein the core is an organic acid or a mixture of organic acids; comprises at least one organic acid; or is a pellet, bead, seed, or a granule coated with at least one coating comprising at least one organic acid.

22. A method for treating symptoms of Parkinson's disease, the method comprising orally administering to a subject in need thereof, a pharmaceutical pellet composition comprising:
a) a core comprising at least one organic acid;
b a drug layer covering at least a portion of the core; and
c) a functional coat covering at least a portion of the drug layer,
wherein the drug layer comprises trihexyphenidyl or a pharmaceutically acceptable salt thereof, and a nonionic water-soluble polymer,
wherein the functional coat comprises a nonionic water-insoluble polymer, and a pore former, wherein the water-insoluble polymer and the pore former are present in a weight ratio of from about 60:40 to about 98:2, and
wherein the composition provides a $C_{min}$:$C_{max}$ ratio of ≥0.4.

* * * * *